(12) United States Patent
Jakob et al.

(10) Patent No.: US 12,331,034 B2
(45) Date of Patent: Jun. 17, 2025

(54) SUBSTITUTED PYRROLIDINE AMIDES V

(71) Applicant: GRUENENTHAL GMBH, Aachen (DE)

(72) Inventors: Florian Jakob, Aachen (DE); Jo Alen, Averbode (BE); Sebastian Krueger, Aachen (DE); Philipp Barbie, Berlin (DE); Daniela Friebe, Duesseldorf (DE)

(73) Assignee: Gruenenthal GmbH, Aachen (DE)

( * ) Notice: Subject to any disclaimer, the term of this patent is extended or adjusted under 35 U.S.C. 154(b) by 765 days.

(21) Appl. No.: 17/554,729

(22) Filed: Dec. 17, 2021

(65) Prior Publication Data

US 2022/0106294 A1   Apr. 7, 2022

Related U.S. Application Data

(63) Continuation of application No. PCT/EP2020/067063, filed on Jun. 19, 2020.

(30) Foreign Application Priority Data

Jun. 19, 2019   (EP) .................................... 19181198

(51) Int. Cl.
| | | |
|---|---|---|
| *C07D 401/14* | (2006.01) | |
| *C07D 401/04* | (2006.01) | |
| *C07D 403/04* | (2006.01) | |
| *C07D 403/14* | (2006.01) | |
| *C07D 405/04* | (2006.01) | |
| *C07D 405/14* | (2006.01) | |

(52) U.S. Cl.
CPC ......... *C07D 401/14* (2013.01); *C07D 401/04* (2013.01); *C07D 403/04* (2013.01); *C07D 403/14* (2013.01); *C07D 405/04* (2013.01); *C07D 405/14* (2013.01)

(58) Field of Classification Search
CPC .................................................. C07D 401/14
See application file for complete search history.

(56) References Cited

U.S. PATENT DOCUMENTS

| | | |
|---|---|---|
| 5,604,252 A | 2/1997 | O'Neill |
| 7,935,719 B2 | 5/2011 | Solvibile et al. |
| 7,947,727 B2 | 5/2011 | Biggadike et al. |
| 8,143,290 B2 | 3/2012 | Berger et al. |
| 8,178,573 B2 | 5/2012 | Biggadike et al. |
| 9,738,632 B2 | 8/2017 | Berger et al. |
| 10,196,374 B2 | 2/2019 | Ripa et al. |
| 10,435,379 B2 | 10/2019 | Kawashima |
| 10,626,106 B2 * | 4/2020 | Jakob ............... A61P 19/02 |
| 2020/0102314 A1 | 4/2020 | Foley et al. |

FOREIGN PATENT DOCUMENTS

| | | |
|---|---|---|
| WO | 93/00330 A2 | 1/1993 |
| WO | 2007/122165 A1 | 11/2007 |
| WO | 2008/043789 A1 | 4/2008 |
| WO | 2008/045371 A2 | 4/2008 |
| WO | 2008/076048 A1 | 6/2008 |
| WO | 2009/035067 A1 | 3/2009 |
| WO | 2009/142571 A1 | 11/2009 |
| WO | 2016/034134 A1 | 3/2016 |
| WO | 2016/040504 A1 | 3/2016 |
| WO | 2016/046260 A1 | 3/2016 |
| WO | 2017/034006 A1 | 3/2017 |

* cited by examiner

*Primary Examiner* — Golam M Shameem
(74) *Attorney, Agent, or Firm* — Norris McLaughlin, P.A.

(57) ABSTRACT

The invention relates to compounds according to general formula (I),

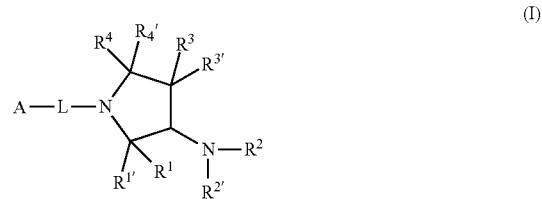

which act as modulators of the glucocorticoid receptor and can be used in the treatment and/or prophylaxis of disorders which are at least partially mediated by the glucocorticoid receptor.

12 Claims, No Drawings

SUBSTITUTED PYRROLIDINE AMIDES V

This application is a continuation of International Patent Application No. PCT/EP2020/067063, filed Jun. 19, 2020, which, in turn, claims priority of European Patent Application No. 19181198.3, filed Jun. 19, 2019, the entire contents of which patent applications are hereby incorporated herein by reference.

The invention relates to compounds according to general formula (I)

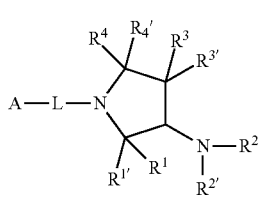

(I)

which act as modulators of the glucocorticoid receptor and can be used in the treatment and/or prophylaxis of disorders which are at least partially mediated by the glucocorticoid receptor.

Glucocorticoids (GC) exert strong anti-inflammatory, immunosuppressive and disease-modifying therapeutic effects mediated by the glucocorticoid receptor (GR). They have been widely used to treat inflammatory and immune diseases for decades and still represent the most effective therapy in those conditions. However, chronic GC treatment of inflammatory diseases such as asthma, rheumatoid arthritis, inflammatory bowel disease, chronic obstructive pulmonary disease, acute respiratory distress syndrome, cystic fibrosis, osteoarthritis, polymyalgia rheumatica and giant cell arteritis is hampered by GC-associated adverse effects. These undesired side effects include insulin resistance, diabetes, hypertension, glaucoma, depression, osteoporosis, adrenal suppression and muscle wasting with osteoporosis and diabetes being the most severe ones from the physician's point of view (Hapgood J P. et al., Pharmacol Ther. 2016 September; 165: 93-113; Buttgereit F. el al, Clin Exp Rheumatol. 2015 July-August; 33(4 Suppl 92): S29-33; Hartmann K et al, Physiol Rev. 2016 April; 96(2):409-47).

One example of an oral glucocorticoid is prednisone which is frequently prescribed for the treatment of several inflammatory disorders (De Bosscher K et al., Trends Pharmacol Sci. 2016 January; 37(1):4-16; Buttgereit F. et al., JAMA. 2016; 315(22):2442-2458). As GC cause adrenal suppression, prednisolone withdrawal symptoms can be severe if the drug is discontinued abruptly when all the signs of the disease have disappeared. Thus gradual GC tapering to physiological doses is frequently part of treatment protocols to reduce the risk of relapse and other withdrawal symptoms (Liu D. et al., Allergy Asthma Clin Immunol. 2013 Aug. 15; 9(1):30). Therefore, there is high medical need for novel potent anti-inflammatory drugs with less adverse effects.

Recent research has focused on the development of partial agonists or selective glucocorticoid receptor modulators which activate the pathways for the inhibition of inflammation but avoid targeting the pathways that lead to the GC-associated adverse effects. Most of these effects have been demonstrated to be mediated by different GR-dependent genomic mechanisms termed transactivation and transrepression. The anti-inflammatory actions of GC are mainly attributable to the transrepression of inflammatory genes while certain side effects are predominantly mediated via transactivation of several genes. According to the nature of a ligand the GR can be selectively modulated in a specific conformation which favors transrepression over transactivation resulting in an improved therapeutic benefit (De Bosscher K et al., Trends Pharmacol Sci. 2016 January; 37(1):4-16). The concept of such dissociating ligands was already defined about two decades ago and several compounds have been identified and were evaluated in preclinical and clinical testing but none of them has as yet been approved for clinical use.

Compounds which are active as modulators of the glucocorticoid receptor are also known e.g. from WO 2007/122165, WO 2008/076048 and WO 2008/043789, WO 2009/035067, WO 2009/142571, WO 2016/046260, and WO 2017/034006.

It was an object of the invention to provide novel compounds which are modulators of the glucocorticoid receptor and which preferably have advantages over the compounds of the prior art. The novel compounds should in particular be suitable for use in the treatment and/or prophylaxis of disorders or diseases which are at least partially mediated by the glucocorticoid receptor.

This object has been achieved by the subject-matter of the patent claims

It was surprisingly found that the compounds according to the invention are highly potent modulators of the glucocorticoid receptor.

The invention relates to a compound according to general formula (I),

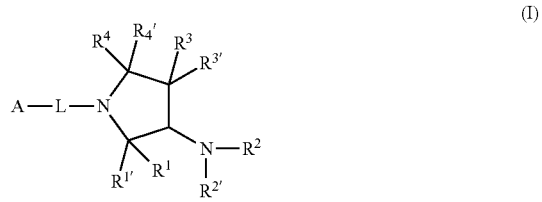

(I)

wherein
$R^1$ represents $—C_{1-10}$-alkyl; $—C_{3-10}$-cycloalkyl; $—C_{1-6}$-alkylene-$C_{3-10}$-cycloalkyl; 3 to 7 membered heterocycloalkyl; $—C_{1-6}$-alkylene-(3 to 7 membered heterocycloalkyl); aryl; $—C_{1-6}$-alkylene-aryl; 5 or 6-membered heteroaryl; or $—C_{1-6}$-alkylene-(5 or 6-membered heteroaryl);
$R^{1'}$ represents H; $—C_{1-10}$-alkyl; or $—C_{3-10}$-cycloalkyl;
or $R^1$ and $R^{1'}$ together with the carbon atom to which they are bound form a $C_{3-10}$-cycloalkyl; or 3 to 7 membered heterocycloalkyl;
$R^2$ represents aryl; 5 or 6-membered heteroaryl; $—C(=O)—C_{1-10}$-alkyl; $—C(=O)—O—C_{1-10}$-alkyl; $—C(=O)—C_{3-10}$-cycloalkyl; $—C(=O)—C_{1-6}$-alkylene-$C_{3-10}$-cycloalkyl; $—C(=O)—O—C_{3-10}$-cycloalkyl; $—C(=O)$-(3 to 7 membered heterocycloalkyl); $—C(=O)—C_{1-6}$-alkylene-(3 to 7 membered heterocycloalkyl); $—C(=O)—O$-(3 to 7 membered heterocycloalkyl); $—C(=O)$-aryl; $—C(=O)—C_{1-6}$-alkylene-aryl; $—C(=O)—O$-aryl; $—C(=O)$-(5 or 6-membered heteroaryl); $—C(=O)—C_{1-6}$-alkylene-(5 or 6-membered heteroaryl); $—C(=O)—O$-(5 or 6-membered heteroaryl); $—S(=O)_{1-2}—C_{1-10}$-alkyl; $—S(=O)_{1-2}—C_{3-10}$-cycloalkyl; $—S(=O)_{1-2}—C_{1-6}$- alkylene-$C_{3-10}$-cycloalkyl; —S(=O)$_{1-2}$-(3 to 7 membered heterocycloalkyl); —S(=O)$_{1-2}$—$C_{1-6}$-alkylene-(3 to 7 membered heterocycloalkyl); —S(=O)$_{1-2}$-aryl; —S(=O)$_{1-2}$—$C_{1-6}$-alkylene-aryl; —S(=O)$_{1-2}$-(5 or 6-membered heteroaryl); or —S(=O)$_{1-2}$—$C_{1-6}$-alkylene-(5 or 6-membered heteroaryl);

$R^{2'}$ represents H;

or $R^2$ and $R^{2'}$ together with the carbon atom to which they are bound form a $C_{3-10}$-cycloalkyl; or 3 to 7 membered heterocycloalkyl;

$R^3$ and $R^{3'}$ independently from one another represent H; F; Cl; —$C_{1-10}$-alkyl; —$C_{3-6}$-cycloalkyl; —$C_{1-6}$-alkylene-$C_{3-6}$-cycloalkyl; 3 to 7 membered heterocycloalkyl; —$C_{1-6}$-alkylene-(3 to 7 membered heterocycloalkyl); —$C_{1-6}$-alkylene-aryl; or —$C_{1-6}$-alkylene-(5 or 6-membered heteroaryl);

or $R^3$ and $R^{3'}$ together with the carbon atom to which they are bound form a $C_{3-10}$-cycloalkyl; or 3 to 7 membered heterocycloalkyl;

$R^4$ and $R^{4'}$ independently from one another represent H; F; Cl; —$C_{1-10}$-alkyl; —$C_{3-6}$-cycloalkyl; —$C_{1-6}$-alkylene-$C_{3-6}$-cycloalkyl; 3 to 7 membered heterocycloalkyl; —$C_{1-6}$-alkylene-(3 to 7 membered heterocycloalkyl); —$C_{1-6}$-alkylene-aryl; or —$C_{1-6}$-alkylene-(5 or 6-membered heteroaryl);

L represents bond or —$C_{1-6}$-alkylene-;

A represents —$C_{1-10}$-alkyl; —$C_{3-6}$-cycloalkyl; —$C_{1-6}$-alkylene-$C_{3-6}$-cycloalkyl; 3 to 7 membered heterocycloalkyl; or —$C_{1-6}$-alkylene-(3 to 7 membered heterocycloalkyl);

or A represents substructure (S1)

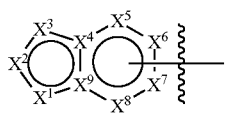

(S1)

wherein $X^1$, $X^2$ and $X^3$ independently from one another represent CH; $CR^5$; N; NH; $NR^5$; O; or S; wherein at least one of $X^1$, $X^2$ and $X^3$ represents N; NH; $NR^5$; O; or S;

$X^4$ and $X^9$ independently from one another represent C or N;

$X^5$, $X^6$, $X^7$ and $X^8$ in each case independently from one another represent CH; $CR^5$; N; or C which is connected to L; wherein one of $X^5$, $X^6$, $X^7$ and $X^8$ represents C which is connected to L;

or A represents substructure (S2)

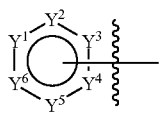

(S2)

wherein $Y^1$, $Y^2$, $Y^3$, $Y^4$, $Y^5$, and $Y^6$ in each case independently from one another represent CH; $CR^5$; N; or C which is connected to L; wherein one of $Y^1$, $Y^2$, $Y^3$, $Y^4$, $Y^5$ and $Y^6$ represents C which is connected to L;

$R^5$ represents H; F; Cl; —$C_{1-10}$-alkyl; —$C_{1-10}$-alkenyl; —$C_{1-10}$-alkynyl; —$C_{3-6}$-cycloalkyl; —$C_{1-6}$-alkylene-$C_{3-6}$-cycloalkyl; 3 to 7 membered heterocycloalkyl; —$C_{1-6}$-alkylene-(3 to 7 membered heterocycloalkyl); aryl; —$C_{1-6}$-alkylene-aryl; 5 or 6-membered heteroaryl; —$C_{1-6}$-alkylene-(5 or 6-membered heteroaryl); —C(=O)—$C_{1-10}$-alkyl; —C(=O)—$C_{3-10}$-cycloalkyl; —C(=O)-(3 to 7 membered heterocycloalkyl); —O—$C_{1-10}$-alkyl; —O—$C_{3-10}$-cycloalkyl; —O-(3 to 7 membered heterocycloalkyl); —O-aryl; —O-(5 or 6-membered heteroaryl); —S(=O)$_{1-2}$—$C_{1-10}$-alkyl; —S(=O)$_{1-2}$—$C_{3-10}$-cycloalkyl; —S(=O)$_{1-2}$-(3 to 7 membered heterocycloalkyl); —S(=O)$_{1-2}$-aryl; or —S(=O)$_{1-2}$-(5 or 6-membered heteroaryl);

wherein —$C_{1-10}$-alkyl, —$C_{1-4}$-alkyl and —$C_{1-6}$-alkylene- in each case independently from one another is linear or branched, saturated or unsaturated;

wherein —$C_{1-10}$-alkyl, —$C_{1-6}$-alkylene-, —$C_{3-10}$-cycloalkyl and 3 to 7 membered heterocycloalkyl in each case independently from one another are unsubstituted or mono- or polysubstituted with one or more substituents selected from —F; —Cl; —Br; —I; —CN; —$CF_3$; —$CF_2H$; —$CFH_2$; —$CF_2Cl$; —$CFCl_2$; —C(=O)—$C_{1-6}$-alkyl; —C(=O)—OH; —C(=O)—O$C_{1-6}$-alkyl; —C(=O)—$NH_2$; —C(=O)—NH($C_{1-6}$-alkyl); —C(=O)—N($C_{1-6}$-alkyl)$_2$; —OH; =O; —$OCF_3$; —$OCF_2H$; —$OCFH_2$; —$OCF_2Cl$; —$OCFCl_2$; —O—$C_{1-6}$-alkyl; —O—C(=O)—$C_{1-6}$-alkyl; —O—C(=O)—O—$C_{1-6}$-alkyl; —O—(CO)—NH($C_{1-6}$-alkyl); —O—C(=O)—N($C_{1-6}$-alkyl)$_2$; —O—S(=O)$_2$—$NH_2$; —O—S(=O)$_2$—NH($C_{1-6}$-alkyl); —O—S(=O)$_2$—N($C_{1-6}$-alkyl)$_2$; —$NH_2$; —NH($C_{1-6}$-alkyl); —N($C_{1-6}$-alkyl)$_2$; —NH—C(=O)—$C_{1-6}$-alkyl; —NH—C(=O)—O—$C_{1-6}$-alkyl; —NH—C(=O)—$NH_2$; —NH—C(=O)—NH($C_{1-6}$-alkyl); —NH—C(=O)—N($C_{1-6}$-alkyl)$_2$; —N($C_{1-6}$-alkyl)-C(=O)—$C_{1-6}$-alkyl; —N($C_{1-6}$-alkyl)-C(=O)—O—$C_{1-6}$-alkyl; —N($C_{1-6}$-alkyl)-C(=O)—$NH_2$; —N($C_{1-6}$-alkyl)-C(=O)—NH($C_{1-6}$-alkyl); —N($C_{1-6}$-alkyl)-C(=O)—N($C_{1-6}$-alkyl)$_2$; —NH—S(=O)$_2$OH; NH—S(=O)$_2$—$C_{1-6}$-alkyl; —NH—S(=O)$_2$—O—$C_{1-6}$-alkyl; —NH—S(=O)$_2$—$NH_2$; —NH—S(=O)$_2$—NH($C_{1-6}$-alkyl); —NH—S(=O)$_2$N($C_{1-6}$-alkyl)$_2$; —N($C_{1-6}$-alkyl)-S(=O)$_2$—OH; —N($C_{1-6}$-alkyl)-S(=O)$_2$—$C_{1-6}$-alkyl; —N($C_{1-6}$-alkyl)-S(=O)$_2$—O—$C_{1-6}$-alkyl; —N($C_{1-6}$-alkyl)-S(=O)$_2$—$NH_2$; —N($C_{1-6}$-alkyl)-S(=O)$_2$—NH($C_{1-6}$-alkyl); —N($C_{1-6}$-alkyl)-S(=O)$_2$—N($C_{1-6}$-alkyl)$_2$; —$SCF_3$; —$SCF_2H$; —$SCFH_2$; —S(=O)—$C_{1-6}$-alkyl; —S(=O)$_2$—$C_{1-6}$-alkyl; —S(=O)$_2$—OH; —S(=O)$_2$—O—$C_{1-6}$-alkyl; —S(=O)$_2$—$NH_2$; —S(=O)$_2$—NH($C_{1-6}$-alkyl); —S(=O)$_2$—N($C_{1-6}$-alkyl)$_2$; —$C_{3-6}$-cycloalkyl; 3 to 6-membered heterocycloalkyl; phenyl; 5 or 6-membered heteroaryl; —O—$C_{3-6}$-cycloalkyl; —O-(3 to 6-membered heterocycloalkyl); —O-phenyl; —O-(5 or 6-membered heteroaryl); —C(=O)—$C_{3-6}$-cycloalkyl; —C(=O)-(3 to 6-membered heterocycloalkyl); —C(=O)-phenyl; —C(=O)-(5 or 6-membered heteroaryl); —S(=O)$_2$—($C_{3-6}$-cycloalkyl); —S(=O)$_2$-(3 to 6-membered heterocycloalkyl); —S(=O)$_2$-phenyl or —S(=O)$_2$-(5 or 6-membered heteroaryl);

wherein aryl and 5 or 6-membered heteroaryl in each case independently from one another are unsubstituted or mono- or polysubstituted with one or more substituents selected from —F; —Cl; —Br; —I; —CN; —$C_{1-6}$-alkyl; —$CF_3$; —$CF_2H$; —$CFH_2$; —$CF_2Cl$; —$CFCl_2$; —$C_{1-4}$-alkylene-$CF_3$; —$C_{1-4}$-alkylene-$CF_2H$; —$C_{1-4}$-alkylene-$CFH_2$; —C(=O)—$C_{1-6}$-alkyl; —C(=O)—OH; —C(=O)—O$C_{1-6}$-alkyl; —C(=O)—NH(OH);

—C(=O)—NH$_2$; —C(=O)—NH(C$_{1-6}$-alkyl); —C(=O)—N(C$_{1-6}$-alkyl)$_2$; —OH; =O; —OCF$_3$; —OCF$_2$H; —OCFH$_2$; —OCF$_2$Cl; —OCFCl$_2$; —O—C$_{1-6}$-alkyl; —O—C$_{3-6}$-cycloalkyl; —O-(3 to 6-membered heterocycloalkyl); —O-aryl; —O-(5 or 6-membered heteroaryl); —NH$_2$; —NH(C$_{1-6}$-alkyl); —N(C$_{1-6}$-alkyl)$_2$; —NH—C(=O)—C$_{1-6}$-alkyl; —N(C$_{1-6}$-alkyl)-C(=O)—C$_{1-6}$-alkyl; —NH—C(=O)—NH$_2$; —NH—C(=O)—NH(C$_{1-6}$-alkyl); —NH—C(=O)—N(C$_{1-6}$-alkyl)$_2$; —N(C$_{1-6}$-alkyl)-C(=O)—NH(C$_{1-6}$-alkyl); —N(C$_{1-6}$-alkyl)-C(=O)—N(C$_{1-6}$-alkyl)$_2$; —NH—S(=O)$_2$—C$_{1-6}$-alkyl; —SCF$_3$; —S—C$_{1-6}$-alkyl; —S(=O)—C$_{1-6}$-alkyl; —S(=O)$_2$—C$_{1-6}$-alkyl; —S(=O)$_2$—NH$_2$; —S(=O)$_2$—NH(C$_{1-6}$-alkyl); —S(=O)$_2$—N(C$_{1-6}$-alkyl)$_2$; —C$_{3-6}$-cycloalkyl; —C$_{1-4}$-alkylene-C$_{3-6}$-cycloalkyl; —C$_{1-4}$-alkylene-(3 to 6-membered heterocycloalkyl); or phenyl;

in the form of the free compound or a physiologically acceptable salt thereof.

In a preferred embodiment, the compound according to the invention is present in form of the free compound. For the purpose of specification, "free compound" preferably means that the compound according to the invention is not present in form of a salt. Methods to determine whether a chemical substance is present as the free compound or as a salt are known to the skilled artisan such as $^{14}$N or $^{15}$N solid state NMR, x-ray diffraction, x-ray powder diffraction, IR, Raman, XPS. $^{1}$H-NMR recorded in solution may also be used to consider the presence of protonation.

In another preferred embodiment, the compound according to the invention is present in form of a physiologically acceptable salt. For the purposes of this specification, the term "physiologically acceptable salt" preferably refers to a salt obtained from a compound according to the invention and a physiologically acceptable acid or base.

According to the invention, the compound according to the invention may be present in any possible form including solvates, cocrystals and polymorphs. For the purposes of this specification, the term "solvate" preferably refers to an adduct of (i) a compound according to the invention and/or a physiologically acceptable salt thereof with (ii) distinct molecular equivalents of one or more solvents.

Further, the compound according to the invention may be present in form of the racemate, enantiomers, diastereomers, tautomers or any mixtures thereof.

The invention also includes isotopic isomers of a compound of the invention, wherein at least one atom of the compound is replaced by an isotope of the respective atom which is different from the naturally predominantly occurring isotope, as well as any mixtures of isotopic isomers of such a compound. Preferred isotopes are $^{2}$H (deuterium), $^{3}$H (tritium), $^{13}$C and $^{14}$C. Isotopic isomers of a compound of the invention can generally be prepared by conventional procedures known to a person skilled in the art.

According to the invention, the terms "—C$_{1-10}$-alkyl", "—C$_{1-8}$-alkyl", "—C$_{1-6}$-alkyl" and "—C$_{1-4}$-alkyl" preferably mean acyclic saturated or unsaturated aliphatic (i.e. non-aromatic) hydrocarbon residues, which can be linear (i.e. unbranched) or branched and which can be unsubstituted or mono- or polysubstituted (e.g. di- or trisubstituted), and which contain 1 to 10 (i.e. 1, 2, 3, 4, 5, 6, 7, 8, 9 or 10), 1 to 8 (i.e. 1, 2, 3, 4, 5, 6, 7 or 8), 1 to 6 (i.e. 1, 2, 3, 4, 5 or 6) and 1 to 4 (i.e. 1, 2, 3 or 4) carbon atoms, respectively. In a preferred embodiment, —C$_{1-10}$-alkyl, —C$_{1-8}$-alkyl, —C$_{1-6}$-alkyl and —C$_{1-4}$-alkyl are saturated.

Preferred —C$_{1-10}$-alkyl groups are selected from methyl, ethyl, ethenyl (vinyl), n-propyl, 2-propyl, 1-propynyl, 2-propynyl, propenyl (—CH$_2$CH=CH$_2$, —CH=CH—CH$_3$, —C(=CH$_2$)—CH$_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, 1-propynyl, 2-propynyl, propenyl (—CH$_2$CH=CH$_2$, —CH=CH—CH$_3$, —C(=CH$_2$)—CH$_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, n-heptyl, n-octyl, n-nonyl and n-decyl. Particularly preferred —C$_{1-10}$-alkyl groups are selected from C$_{1-4}$-alkyl groups.

Preferred —C$_{1-8}$-alkyl groups are selected from methyl, ethyl, ethenyl (vinyl), n-propyl, 2-propyl, 1-propynyl, 2-propynyl, propenyl (—CH$_2$CH=CH$_2$, —CH=CH—CH$_3$, —C(=CH$_2$)—CH$_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, 1-propynyl, 2-propynyl, propenyl (—CH$_2$CH=CH$_2$, —CH=CH—CH$_3$, —C(=CH$_2$)—CH$_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, n-heptyl and n-octyl. Particularly preferred —C$_{1-8}$-alkyl groups are selected from C$_{1-4}$-alkyl groups.

Preferred —C$_{1-6}$-alkyl groups are selected from methyl, ethyl, ethenyl (vinyl), n-propyl, 2-propyl, n-butyl, isobutyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, 1-propynyl, 2-propynyl, propenyl (—CH$_2$—CH=CH$_2$, —CH=CH—CH$_3$, —C(=CH$_2$)—CH$_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-penlynyl, 2-methylbutyl, 3-methylbutyl, 3-methylbut-2-yl, 2-methylbut-2-yl, 3-methylbut-1-ynyl, 2,2-dimethylpropyl, n-hexyl. Particularly preferred —C$_{1-6}$-alkyl groups are selected from C$_{1-4}$-alkyl groups.

Preferred —C$_{1-4}$-alkyl groups are selected from methyl, ethyl, ethenyl (vinyl), n-propyl, 2-propyl, 1-propynyl, 2-propynyl, propenyl (—CH$_2$CH=CH$_2$, —CH=CH—CH$_3$, —C(=CH$_2$)—CH$_3$), n-butyl, 1-butynyl, 2-butynyl, 1-butenyl, 2-butenyl, isobutyl, sec-butyl, tert-butyl and 3-methylbut-1-ynyl. More preferred —C$_{1-4}$-alkyl groups are selected from methyl, ethyl, n-propyl, 2-propyl, 1-propynyl, 2-propynyl, n-butyl, isobutyl, sec-butyl, and tert-butyl.

Further according to the invention, the terms "—$C_{1-6}$-alkylene-"; "—$C_{1-4}$-alkylene" and "—$C_{1-2}$-alkylene" relate to a linear or branched, preferably linear, and preferably saturated aliphatic residues which are preferably selected from the group consisting of methylene (—$CH_2$—), ethylene (—$CH_2CH_2$—), propylene (—$CH_2CH_2CH_2$— or —$C(CH_3)_2$—), butylene (—$CH_2CH_2CH_2CH_2$—), pentylene (—$CH_2CH_2CH_2CH_2CH_2$—) and hexylene (—$CH_2CH_2CH_2CH_2CH_2CH_2$—); more preferably methylene (—$CH_2$—) and ethylene (—$CH_2CH_2$—) and most preferably methylene (—$CH_2$—). Preferably, —$C_{1-6}$-alkylene- is selected from —$C_{1-4}$-alkylene-, more preferably from —$C_{1-2}$-alkylene-.

Still further according to the invention, the terms "—$C_{3-10}$-cycloalkyl" and "—$C_{3-6}$-cycloalkyl" preferably mean cyclic aliphatic hydrocarbons containing 3, 4, 5, 6, 7, 8, 9 or 10 carbon atoms and 3, 4, 5 or 6 carbon atoms, respectively, wherein the hydrocarbons in each case can be saturated or unsaturated (but not aromatic), unsubstituted or mono- or poly substituted.

Preferably, —$C_{3-10}$-cycloalkyl and —$C_{3-6}$-cycloalkyl are saturated. The —$C_{3-10}$-cycloalkyl and —$C_{3-6}$-cycloalkyl can be bound to the respective superordinate general structure via any desired and possible ring member of the cycloalkyl group. The —$C_{3-10}$-cycloalkyl and —$C_{3-6}$-cycloalkyl groups can also be condensed with further saturated, (partially) unsaturated, (hetero)cyclic, aromatic or heteroaromatic ring systems, i.e. with cycloalkyl, heterocyclyl, aryl or heteroalyl residues, which in each case can in turn be unsubstituted or mono- or polysubstituted. Further, —$C_{3-10}$-cycloalkyl and —$C_{3-6}$-cycloalkyl can be singly or multiply bridged such as, for example, in the case of adamantyl, bicyclo[2.2.1]heptyl or bicyclo[2.2.2]octyl. However, preferably, —$C_{3-10}$-cycloalkyl and —$C_{3-6}$-cycloalkyl are neither condensed with further ring systems nor bridged. More preferably, —$C_{3-10}$-cycloalkyl and —$C_{3-6}$-cycloalkyl are neither condensed with further ring systems nor bridged and are saturated. Preferred —$C_{3-10}$-cycloalkyl groups are selected from the group consisting of cyclopropyl, cyclobutyl, cyclopentyl, cyclohexyl, cyclopentenyl, cyclohexenyl, cyclo-heptyl, cyclooctyl, cyclononyl, cyclodecyl, adamantly, cyclopentenyl, cyclohexenyl, cycloheptenyl and cyclooctenyl. Particularly preferred —$C_{3-10}$-cycloalkyl groups are selected from —$C_{3-6}$-cycloalkyl groups.

Preferred —$C_{3-6}$-cycloalkyl groups are selected from the group consisting of cyclopropyl, cyclobutyl, cyclopentyl, cyclohexyl, cyclopentenyl and cyclohexenyl. Particularly preferred —$C_{3-6}$-cycloalkyl groups are selected from the group consisting of cyclopropyl, cyclobutyl, cyclopentyl and cyclohexyl, most preferably cyclopropyl and cyclobutyl.

According to the invention, the terms "3 to 7-membered heterocycloalkyl" and "3 to 6-membered heterocycloalkyl" preferably mean heterocycloaliphatic saturated or unsaturated (but not aromatic) residues having 3 to 7, i.e. 3, 4, 5, 6 or 7 ring members and 3 to 6, i.e. 3, 4, 5 or 6 ring members, respectively, wherein in each case at least one, if appropriate also two or three carbon atoms are replaced by a heteroatom or a heteroatom group each selected independently of one another from the group consisting of O, S, S(=O), S(=O)$_2$, N, NH and N($C_{3-4}$-alkyl) such as N($CH_3$), wherein the carbon atoms of the ring can be unsubstituted or mono- or polysubstituted. Preferably, the 3 to 7-membered heterocycloalkyl and the 3 to 6-membered heterocycloalkyl contain only one heteroatom or heteroatom group within the ring.

Preferably, 3 to 7-membered heterocycloalkyl and 3 to 6-membered heterocycloalkyl are saturated. The 3 to 7-membered heterocycloalkyl and the 3 to 6-membered heterocycloalkyl groups can also be condensed with further saturated or (partially) unsaturated cycloalkyl or heterocyclyl, aromatic or heteroaromatic ring systems. However, more preferably, 3 to 7-membered heterocycloalkyl and 3 to 6-membered heterocycloalkyl are not condensed with further ring systems. Still more preferably, 3 to 7-membered heterocycloalkyl and 3 to 6-membered heterocycloalkyl are not condensed with further ring systems and are saturated. The 3 to 7-membered heterocycloalkyl and the 3 to 6-membered heterocycloalkyl group can be bound to the superordinate general structure via any desired and possible ring member of the heterocycloaliphatic residue if not indicated otherwise. In a preferred embodiment, 3 to 7-membered heterocycloalkyl and 3 to 6-membered heterocycloalkyl are bound to the superordinate general structure via a carbon atom.

Preferred 3 to 7-membered heterocycloalkyl groups are selected from the group consisting of tetrahydrofuranyl, azepanyl, dioxepanyl, oxazepanyl, diazepanyl, thiazolidinyl, tetrahydrothiophenyl, tetrahydropyridinyl, thiomorpholinyl, tetrahydropyranyl, oxetanyl, oxiranyl, morpholinyl, pyrrolidinyl, pyrrolidinonyl, 4-methylpiperazinyl, morpholinonyl, azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, piperazinyl, piperidinyl, N-methylpyridinonyl, pyrazolidinyl, pyranyl; tetrahydropyrrolyl, dihydroquinolinyl, dihydroisoquinolinyl, dihydroindolinyl, dihydroisoindolyl, tetrahydroquinolinyl, tetrahydroisoquinolinyl and tetrahydroindolinyl. Particularly preferred 3 to 7-membered heterocycloalkyl groups are selected from 3 to 6-membered heterocycloalkyl groups.

Preferred 3 to 6-membered heterocycloalkyl groups are selected from the group consisting of tetrahydrofuranyl, tetrahydropyranyl, oxetanyl, oxiranyl, thiazolidinyl, tetrahydrothiophenyl, tetrahydropyridinyl, thiomorpholinyl, morpholinyl, pyrrolidinyl, pyrrolidinonyl, 4-methylpiperazinyl, morpholinonyl, azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, piperazinyl, piperidinyl, N-methylpyridinonyl, pyrazolidinyl, pyranyl, tetrahydropyrrolyl, dihydroindolinyl, dihydroisoindolyl and tetrahydroindolinyl. More preferred 3 to 6-membered heterocycloalkyl groups are selected from the group consisting of N-methylpyridinonyl, tetrahydrofuranyl, tetrahydropyranyl, oxetanyl, and oxiranyl; still more preferably N-methylpyridinonyl.

According to the invention, the term "aryl" preferably means aromatic hydrocarbons having 6 to 14, i.e. 6, 7, 8, 9, 10, 11, 12, 13 or 14 ring members, preferably having 6 to 10, i.e. 6, 7, 8, 9 or 10 ring members, including phenyls and naphthyls. Each aryl residue can be unsubstituted or mono- or polysubstituted. The aryl can be bound to the superordinate general structure via any desired and possible ring member of the aryl residue. The aryl residues can also be condensed with further saturated or (partially) unsaturated cycloalkyl or heterocycloalkyl, aromatic or heteroaromatic ring systems, which can in turn be unsubstituted or mono- or polysubstituted. In a preferred embodiment, aryl is condensed with a further ring system. Examples of condensed aryl residues are 2H-benzo [b][1,4]oxazin-3 (4H)-onyl, 1H-benzo[d]imidazolyl, 2,3-dihydro-1H-indenyl, tetrahydronaphthalenyl, isochroman, 1,3-dihydroisobenzofuranyl, benzodioxolanyl and benzodioxanyl. In another preferred embodiment, aryl is not condensed with any further ring system.

Preferably, aryl is selected from the group consisting of phenyl, benzodioxanyl, 1H-benzo[d]imidazolyl, 2H-benzo[b][1,4]oxazin-3 (4H)-onyl, 2,3-dihydro-1H-indenyl, tetrahydronaphthalenyl, isochroman, 1,3-dihydroiso-benzofuranyl, 1-naphthyl, 2-naphthyl, fluorenyl and anthracenyl, each of which can be respectively unsubstituted or mono- or polysubstituted. A particularly preferred aryl is phenyl or benzodioxanyl, in each case unsubstituted or mono- or poly substituted.

According to the invention, the term "5- to 6-membered heteroaryl" preferably means a 5 or 6-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted, if not indicated otherwise. In the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. Preferably, the 5- to 6-membered heteroaryl is bound to the suprordinate general structure via a carbon atom of the heterocycle. The heteroaryl can also be part of a bi- or polycyclic system having up to 14 ring members, wherein the ring system can be formed with further saturated or (partially) unsaturated cycloalkyl or heterocycloalkyl, aromatic or heteroaromatic ring systems, which can in turn be unsubstituted or mono- or polysubstituted, if not indicated otherwise. In a preferred embodiment, the 5- to 6-membered heteroaryl is part of a bi- or polycyclic, preferably bicyclic, system. In another preferred embodiment, the 5- to 6-membered heteroaryl is not part of a bi- or polycyclic system.

Preferably, the 5- to 6-membered heteroaryl is selected from the group consisting of pyridyl (i.e. 2-pyridyl, 3-pyridyl, 4-pyridyl), thiazolyl, pyrazolyl, oxadiazolyl, pyrimidinyl, indazolyl, indolyl, N-methylpyridinonyl, oxazolyl, isoxazolyl, pyridone (pyridinone), pyridazinyl, pyrazinyl, pyrrolyl, imidazolyl, isothiazolyl, furanyl, thienyl (thiophenyl), triazolyl, thiadiazolyl, 4,5,6,7-tetrahydro-2H-indazolyl, 2,4,5,6-tetrahydrocyclopenta[c]pyrazolyl, benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, calbazolyl, quinolinyl, dibenzofuranyl, dibenzothienyl, imidazothiazolyl, indolizinyl, isoquinolinyl, naphthyridinyl, oxazolyl, phenazinyl, phenothiazinyl, phthalazinyl, purinyl, phenazinyl, tetrazolyl and triazinyl. Particularly preferred 5- to 6-membered heteroaryl are selected from the group consisting of pyridyl (i.e. 2-pyridyl, 3-pyridyl, 4-pyridyl), N-methylpyridinonyl, thiazolyl, oxazolyl, isoxazolyl, pyrazolyl, and oxadiazolyl. As pyridones can be regarded as pyridines that are substituted with =O, for the purpose of the specification the definition of pyridines that may optionally be substituted with =O covers pyridones.

The compounds according to the invention are defined by substituents, for example by $R^1$, $R^2$ and $R^3$ ($1^{st}$ generation substituents) which may optionally be for their part themselves be substituted ($2^{nd}$ generation substituents). Depending on the definition, these substituents of the substituents can optionally be for their part resubstituted ($3^{rd}$ generation substituents). If, for example, $R^1$=phenyl ($1^{st}$ generation substituent), then the phenyl can for its part be substituted, for example with —$C_{1-6}$-alkyl ($2^{nd}$ generation substituent). This produces the functional group $R^1$=phenyl-$C_{1-6}$-alkyl. The —$C_{1-6}$-alkyl can then for its part be resubstituted, for example with —F ($3^{rd}$ generation substituent). Overall, this produces the functional group $R^1$=phenyl-$C_{1-6}$-alkyl, wherein the —$C_{1-6}$-alkyl is substituted with —F.

However, in a preferred embodiment, the 3rd generation substituents may not be resubstituted, i.e. there are then no $4^{th}$ generation substituents. More preferably, the $2^{nd}$ generation substituents may not be resubstituted, i.e. there are no $3^{rd}$ generation substituents.

If a residue occurs multiply within a molecule, then this residue can have respectively different meanings for various substituents: if, for example, both $R^3$ and $R^{3'}$ denote —$C_{1-10}$-alkyl, then —$C_{1-10}$-alkyl can e.g. represent ethyl for $R^3$ and can represent methyl for $R^{3'}$.

In connection with the terms "—$C_{1-10}$-alkyl", "—$C_{1-6}$-alkyl", "—$C_{1-4}$-alkyl", "—$C_{3-10}$-cycloakl", "—$C_{3-6}$-cycloalkyl", "3 to 7 membered heterocycloalkyl", "3 to 6-membered heterocycloalkyl", "—$C_{1-6}$-alkylene-", "—$C_{1-4}$-alkylene-" and "—$C_{1-2}$-alkylene-", the term "substituted" refers in the sense of the invention, with respect to the corresponding residues or groups, to the single substitution (monosubstitution) or multiple substitution (polysubstitution), e.g. disubstitution or trisubstitution; more preferably to monosubstitution or disubstitution; of one or more hydrogen atoms each independently of one another by at least one substituent. In case of a multiple substitution, i.e. in case of poly substituted residues, such as di- or trisubstituted residues, these residues may be poly substituted either on different or on the same atoms, for example trisubstituted on the same carbon atom, as in the case of —$CF_3$, —$CH_2CF_3$ or disubstituted as in the case of 1,1-difluorocyclohexyl, or at various points, as in the case of —CH(OH)—CH=CH—$CHCl_2$ or 1-chloro-3-fluorocyclohexyl. The multiple substitution can be carried out using the same or using different substituents.

In relation to the terms "aryl" and "5- to 6-membered heteroaryl", the term "substituted" refers in the sense of this invention to the single substitution (monosubstitution) or multiple substitution (polysubstitution), e.g. disubstitution or trisubstitution, of one or more hydrogen atoms each independently of one another by at least one substituent. The multiple substitution can be carried out using the same or using different substituents.

According to the invention, preferably —$C_{1-10}$-alkyl-, —$C_{1-6}$-alkyl, —$C_{3-10}$-cycloalkyl, —$C_{3-6}$-cyclo-alkyl, 3 to 7 membered heterocycloalkyl, 3 to 6-membered heterocycloalkyl, —$C_{1-6}$-alkylene-, —$C_{1-4}$-alkylene- and —$C_{1-2}$-alkylene- in each case independently from one another are unsubstituted or mono- or polysubstituted with one or more substituents selected from —F; —Cl; —Br; —I; —CN; —$C_{1-6}$-alkyl; —$CF_3$; —$CF_2H$; —$CFH_2$; —$CF_2Cl$; —$CFCl_2$; —C(=O)—$C_{1-6}$-alkyl; —C(=O)—OH; —C(=O)—$OC_{1-6}$-alkyl; —C(=O)—$NH_2$; —C(=O)—NH($C_{1-6}$-alkyl); —C(=O)—N($C_{1-6}$-alkyl)$_2$; —OH; =O; —$OCF_3$; —$OCF_2H$; —$OCFH_2$; —$OCF_2Cl$; —$OCFCl_2$; —O—$C_{1-6}$-alkyl; —O—C(=O)—$C_{1-6}$-alkyl; —O—C(=O)—O—$C_{1-6}$-alkyl; —O—(CO)—NH($C_{1-6}$-alkyl); —O—C(=O)—N($C_{1-6}$-alkyl)$_2$; —O—S(=O)$_2$—$NH_2$; —O—S(=O)$_2$—NH($C_{1-6}$-alkyl); —O—S(=O)$_2$—N($C_{1-6}$-alkyl)$_2$; —$NH_2$; —NH($C_{1-6}$-alkyl); —N($C_{1-6}$-alkyl)$_2$; —NH—C(=O)—$C_{1-6}$-alkyl; —NH—C(=O)—O—$C_{1-6}$-alkyl; —NH—C(=O)—$NH_2$; —NH—C(=O)—NH($C_{1-6}$-alkyl); —NH—C(=O)—N($C_{1-6}$-alkyl)$_2$; —N($C_{1-6}$-alkyl)-C(=O)—$C_{1-6}$-alkyl; —N($C_{1-6}$-alkyl)-C(=O)—O—$C_{1-6}$-alkyl; —N($C_{1-6}$-alkyl)-C(=O)—$NH_2$; —N($C_{1-6}$-alkyl)-C (=O)—NH(C$_{1-6}$-alkyl); —N(C$_{1-6}$-alkyl)-C(=O)—N(C$_{1-6}$-alkyl)$_2$; —NH—S(=O)$_2$OH; NH—S(=O)$_2$—C$_{1-6}$-alkyl; —NH—S(=O)$_2$—O—C$_{1-6}$-alkyl; —NH—S(=O)$_2$—NH$_2$; —NH—S(=O)$_2$—NH(C$_{1-6}$-alkyl); —NH—S(=O)$_2$N(C$_{1-6}$-alkyl)$_2$; —N(C$_{1-6}$-alkyl)-S(=O)$_2$—OH; —N(C$_{1-6}$-alkyl)-S(=O)$_2$—C$_{1-6}$-alkyl; —N(C$_{1-6}$-alkyl)-S(=O)$_2$—O—C$_{1-6}$-alkyl; —N(C$_{1-6}$-alkyl)-S(=O)$_2$—NH$_2$; —N(C$_{1-6}$-alkyl)-S(=O)$_2$—NH(C$_{1-6}$-alkyl); —N(C$_{1-6}$-alkyl)-S(=O)$_2$—N(C$_{1-6}$-alkyl)$_2$; —SCF$_3$; —SCF$_2$H; —SCFH$_2$; —S—C$_{1-6}$-alkyl; —S(=O)—C$_{1-6}$-alkyl; —S(=O)$_2$—C$_{1-6}$-alkyl; —S(=O)$_2$—OH; —S(=O)$_2$—O—C$_{1-6}$-alkyl; —OS(=O)$_2$—NH$_2$; —S(=O)$_2$—NH(C$_{1-6}$-alkyl); —S(=O)$_2$—N(C$_{1-6}$-alkyl)$_2$; —C$_{3-6}$-cycloalkyl; 3 to 6-membered heterocycloalkyl; phenyl; 5 or 6-membered heteroaryl; —O—C$_{3-6}$-cycloalkyl; —O-(3 to 6-membered heterocycloalkyl); —O-phenyl; —O-(5 or 6-membered heteroaryl); —C(=O)—C$_{3-6}$-cycloalkyl; —C(=O)-(3 to 6-membered heterocycloalkyl); —C(=O)-phenyl; —C(=O)-(5 or 6-membered heteroaryl); —S(=O)$_2$—(C$_{3-6}$-cycloalkyl); —S(=O)$_2$-(3 to 6-membered heterocycloalkyl); —S(=O)$_2$-phenyl or —S(=O)$_2$-(5 or 6-membered heteroaryl).

Preferred substituents of —C$_{1-10}$-alkyl, —C$_{1-6}$-alkyl, —C$_{1-4}$-alkyl, —C$_{3-10}$-cycloalkyl, —C$_{3-6}$-cycloalkyl, 3 to 7 membered heterocycloalkyl, 3 to 6-membered heterocycloalkyl, —C$_{1-6}$-alkylene- and —C$_{1-4}$-alkylene- are selected from the group consisting of —F; —Cl; —Br; —I; —CN; —C$_{1-6}$-alkyl; —CF$_3$; —CF$_2$H; —CFH$_2$; —C(=O)—NH$_2$; —C(=O)—NH(C$_{1-6}$-alkyl); —C(=O)—N(C$_{1-6}$-alkyl)$_2$; =O; —OH; —OCF$_3$; —OCF$_2$H; —OCFH$_2$; —O—C$_{1-6}$-alkyl; —NH$_2$; —NH(C$_{1-6}$-alkyl); —N(C$_{1-6}$-alkyl)$_2$; —SCF$_3$; —SCF$_2$H; —SCFH$_2$; —S—C$_{1-6}$-alkyl; —S(=O)—C$_{1-6}$-alkyl; —S(=O)$_2$—C$_{1-6}$-alkyl; —C$_{3-6}$-cycloalkyl; 3 to 6-membered heterocycloalkyl; phenyl and 5 or 6-membered heteroaryl; and particularly preferably —F, —CN, —CH$_3$, —CH$_2$CH$_3$, —CF$_3$; —CF$_2$H; —CFH$_2$; —C(=O)—NH$_2$; —C(=O)—NH(CH$_3$); —C(=O)—N(CH$_3$)$_2$; =O; —OH, —NH$_2$, —OCH$_3$, —SCH$_3$, —S(=O)$_2$(CH$_3$), —S(=O)(CH$_3$), —N(CH$_3$)$_2$, cyclopropyl and oxetanyl. According to this embodiment, —C$_{1-10}$-alkyl, —C$_{1-6}$-alkyl, —C$_{1-4}$-alkyl, —C$_{3-10}$-cycloalkyl, —C$_{3-6}$-cycloalkyl, 3 to 7 membered heterocycloalkyl, 3 to 6-membered heterocycloalkyl are preferably each independently from one another unsubstituted, mono- di- or trisubstituted, more preferably unsubstituted or monosubstituted or disubstituted with a substituent selected from the group consisting of —F; —Cl; —Br; —I; —CN; —C$_{1-6}$-alkyl; —CF$_3$; —CF$_2$H; —CFH$_2$; —C(=O)—NH$_2$; —C(=O)—NH(C$_{1-6}$-alkyl); —C(=O)—N(C$_{1-6}$-alkyl)$_2$; =O; —OH; —OCF$_3$; —OCF$_2$H; —OCFH$_2$; —O—C$_{1-6}$-alkyl; —NH$_2$; —NH(C$_{1-6}$-alkyl); —N(C$_{1-6}$-alkyl)$_2$; —SCF$_3$; —SCF$_2$H; —SCFH$_2$; —S—C$_{1-6}$-alkyl; —S(=O)—C$_{1-6}$-alkyl; —S(=O)$_2$—C$_{1-6}$-alkyl; —C$_{3-6}$-cycloalkyl; 3 to 6-membered heterocycloalkyl; phenyl and 5 or 6-membered heteroaryl; more preferably —F; —Cl; —Br; —CN; —C$_{1-6}$-alkyl; —CF$_3$; —CF$_2$H; —CFH$_2$; =O; —OH; —OCF$_3$; —OCF$_2$H; and —OCFH$_2$; and particularly preferably —F; —Cl; —Br; —CH$_3$ and =O. Preferably, —C$_{1-6}$-alkylene- groups and —C$_{1-4}$-alkylene- groups are unsubstituted.

According to the invention, preferably aryl and 5 or 6-membered heteroaryl in each case independently from one another are unsubstituted or mono- or polysubstituted; preferably unsubstituted, mono- di- or trisubstituted, still more preferably unsubstituted or monosubstituted or disubstituted; with one or more substituents selected from —F; —Cl; —Br; —I; —CN; —C$_{1-6}$-alkyl; —CF$_3$; —CF$_2$H; —CFH$_2$; —CF$_2$Cl; —CFCl$_2$; —C$_{1-4}$-alkylene-CF$_3$; —C$_{1-4}$-alkylene-CF$_2$H; —C$_{1-4}$-alkylene-CFH$_2$; —C(=O)—C$_{1-6}$-alkyl; —C(=O)—OH; —C(=O)—OC$_{1-6}$-alkyl; —C(=O)—NH(OH); —C(=O)—NH$_2$; —C(=O)—NH(C$_{1-6}$-alkyl); —C(=O)—N(C$_{1-6}$-alkyl)$_2$; —OH; =O; —OCF$_3$; —OCF$_2$H; —OCFH$_2$; —OCF$_2$Cl; —OCFCl$_2$; —O—C$_{1-6}$-alkyl; —O—C$_{3-6}$-cycloalkyl; —O-(3 to 6-membered heterocycloalkyl); —O-aryl; —O-(5 or 6-membered heteroaryl); —NH$_2$; —NH(C$_{1-6}$-alkyl); —N(C$_{1-6}$-alkyl)$_2$; —NH—C(=O)—C$_{1-6}$-alkyl; —N(C$_{1-6}$-alkyl)-C(=O)—C$_{1-6}$-alkyl; —NH—C(=O)—NH$_2$; —NH—C(=O)—NH(C$_{1-6}$-alkyl); —NH—C(=O)—N(C$_{1-6}$-alkyl)$_2$; —N(C$_{1-6}$-alkyl)-C(=O)—NH(C$_{1-6}$-alkyl); —N(C$_{1-6}$-alkyl)-C(=O)—N(C$_{1-6}$-alkyl)$_2$; —NH—S(=O)$_2$—C$_{1-6}$-alkyl; —SCF$_3$; —S—C$_{1-6}$-alkyl; —S(=O)—C$_{1-6}$-alkyl; —S(=O)$_2$—C$_{1-6}$-alkyl; —S(=O)$_2$—NH$_2$; —S(=O)$_2$—NH(C$_{1-6}$-alkyl); —S(=O)$_2$—N(C$_{1-6}$-alkyl)$_2$; —C$_{3-6}$-cycloalkyl; —C$_{1-4}$-alkylene-C$_{3-6}$-cycloalkyl; —C$_{1-4}$-alkylene-(3 to 6-membered heterocycloalkyl); or phenyl.

Preferred substituents of aryl and 5 or 6-membered heteroaryl are selected from the group consisting of —F; —Cl; —Br; —I; —CN; —C$_{1-6}$-alkyl; —CF$_3$; —CF$_2$H; —CFH$_2$; —C$_{1-4}$-alkylene-CF$_3$; —C$_{1-4}$-alkylene-CF$_2$H; —C$_{1-4}$-alkylene-CFH$_2$; —OH; =O; —OCF$_3$; —OCF$_2$H; —OCFH$_2$; —O—C$_{1-6}$-alkyl; —O—C$_{3-6}$-cycloalkyl; —C$_{3-6}$-cycloalkyl; and —S(=O)$_2$—C$_{1-6}$-alkyl; and more preferably of —F; —Cl; —Br; —CN; —CH$_3$; —CH$_2$CH$_3$; —CF$_3$; —CF$_2$H; —CFH$_2$; —CH$_2$—CF$_3$; —OH; =O; —OCF$_3$; —OCF$_2$H; —OCFH$_2$; —O—CH$_3$; —O-cyclopropyl; cyclopropyl; and —S(=O)$_2$—CH$_3$; still more preferably —F; —Cl; —Br; —CH$_3$; —CH$_2$CH$_3$; —CF$_3$; —CF$_2$H; —CFH$_2$; —OH; =O; —OCF$_3$; —O—CH$_3$; and —S(=O)$_2$—CH$_3$; and particularly preferably preferably —F; —Cl; —Br; —CH$_3$; —O—CH$_3$; =O; and —S(=O)$_2$—CH$_3$. According to this embodiment, aryl and 5 or 6-membered heteroaryl are preferably each independently from one another unsubstituted, mono- di- or trisubstituted, more preferably unsubstituted or monosubstituted or disubstituted with a substituent selected from the group consisting of —F; —Cl; —Br; —I; —CN; —C$_{1-6}$-alkyl; —CF$_3$; —CF$_2$H; —CFH$_2$; —C$_{1-4}$-alkylene-CF$_3$; —C$_{1-4}$-alkylene-CF$_2$H; —C$_{1-4}$-alkylene-CFH$_2$; —OH; =O; —OCF$_3$; —OCF$_2$H; —OCFH$_2$; —O—C$_{1-6}$-alkyl; —O—C$_{3-6}$-cycloalkyl; —C$_{3-6}$-cycloalkyl; and —S(=O)$_2$—C$_{1-6}$-alkyl. A preferred substituted 5 or 6-membered heteroaryl is N-methyl-2-oxo-pyridyl.

In a preferred embodiment, the compound according to the invention has a stereochemistry according to general formula (II), (III), (IV), (V), (VI), (VII), (VIII), (IX), (X), (XI), (XII), (XIII), (XIV), (XV), (XVI) or (XVII)

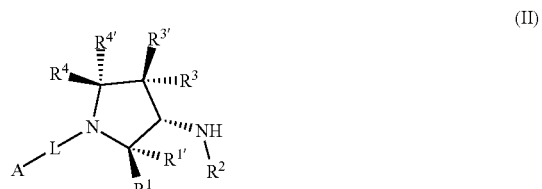

(II)

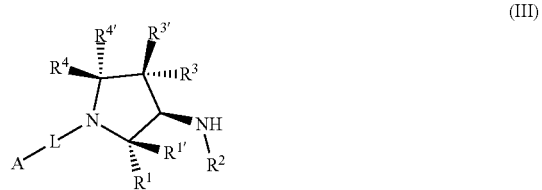

(III)

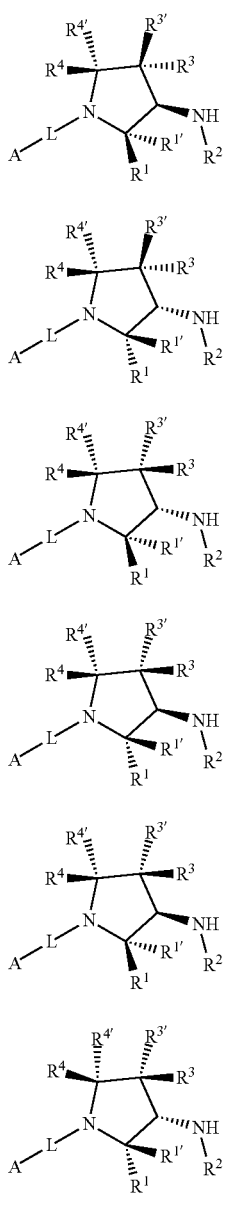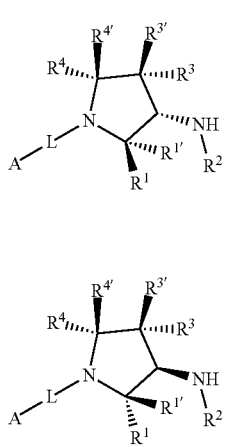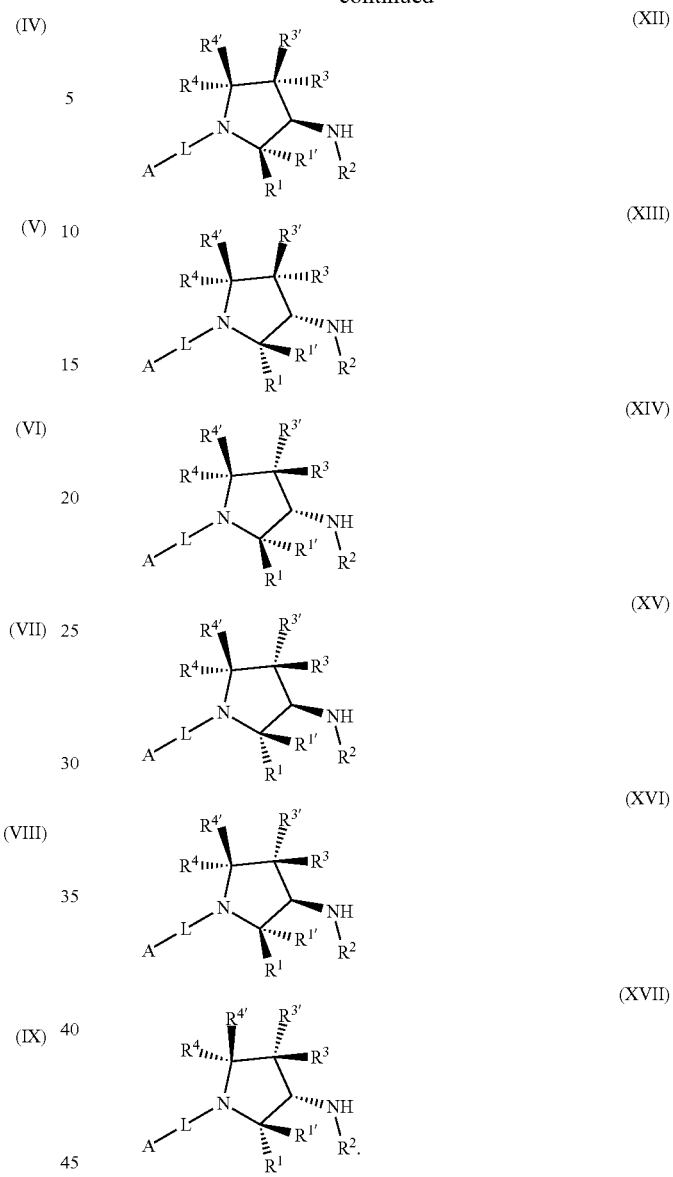

In a preferred embodiment, the compound according to the invention has a stereochemistry according to general formula (II), (III), (VI), (VII), (X), (XI), (XIV) or (XV), such that the residues —$R^1$ and —NH—$R^2$ on the pyrrolidone ring are oriented trans. Preferably, the compound according to the invention has a stereochemistry according to general formula (II) or (VI). Preferably, the compound according to the invention has a stereochemistry according to general formula (III), (VII), (X), (XI), (XIV) or (XV). The stereochemistry according to general formula (II) or (VI) is particularly preferred.

In another preferred embodiment, the compound according to the invention has a stereochemistry according to general formula (IV), (V), (VIII), (IX), (XII), (XIII), (XVI) or (XVII), such that the residues —$R^1$ and —NH—$R^2$ on the pyrrolidone ring are oriented cis. Preferably, the compound according to the invention has a stereochemistry according to general formula (IV) or (VIII). Preferably, the compound according to the invention has a stereochemistry according to general formula (V), (IX), (XII), (XIII), (XVI) or (XVII).

In a particularly preferred embodiment, the compound according to the invention has a stereochemistry according to general formula (II) or (VI).

In the compound of the invention according to any of general formulas (I) to (XVII) represents —$C_{1-10}$-alkyl; —$C_{3-10}$-cycloalkyl; —$C_{1-6}$-alkylene-$C_{3-10}$-cycloalkyl; 3 to 7 membered heterocycloalkyl; —$C_{1-6}$-alkylene-(3 to 7 membered heterocycloalkyl); aryl; —$C_{1-6}$-alkylene-aryl; 5 or 6-membered heteroaryl; or —$C_{1-6}$-alkylene-(5 or 6-membered heteroaryl).

In a preferred embodiment, represents —$C_{1-10}$-alkyl; —$C_{3-10}$-cycloalkyl; —$C_{1-6}$-alkylene-$C_{3-10}$-cycloalkyl; aryl; or 5 or 6-membered heteroaryl; preferably wherein 5 or 6-membered heteroaryl is unsubstituted or mono- or disubstitued with a substituent selected from the group consisting of —$C_{1-4}$-alkyl; —O—$C_{1-4}$-alkyl; —F; —Cl and —Br; more preferably —$C_{1-4}$-alkyl or —O—$C_{1-4}$-alkyl.

Preferably, represents
(i) —$C_{1-10}$-alkyl which is selected from the group consisting of —$CH_3$; —$CH_2CH_3$; n-propyl and 2-propyl, more preferably —$CH_3$ or 2-propyl; or
(ii) —$C_{3-10}$-cycloalkyl which is selected from the group consisting of cyclopropyl and cyclobutyl; or
(iii) —$C_{1-6}$-alkylene-$C_{3-10}$-cycloalkyl which is selected from the group consisting of —$CH_2$-cyclopropyl and —$CH_2$-cyclobutyl; or
(iv) aryl which is selected from the group consisting of phenyl and benzodioxanyl; or
(v) 5 or 6-membered heteroaryl which is selected from the group consisting of pyridinyl and pyrazolyl.

In the compound of the invention according to any of general formulas (I) to (XVII) $R^{1'}$ represents H; —$C_{1-10}$-alkyl; or —$C_{3-10}$-cycloalkyl.

In a preferred embodiment, $R^{1'}$ represents H; methyl, ethyl, n-propyl; cyclopropyl; cyclobutyl; cyclopentyl or cyclohexyl; more preferably H, methyl; ethyl; cyclopropyl or cyclobutyl; still more preferably H; methyl or cyclopropyl.

In a particularly preferred embodiment, $R^{1'}$ represents H.

In a preferred embodiment, represents —$C_{1-10}$-alkyl; —$C_{3-10}$-cycloalkyl; —$C_{1-6}$-alkylene-$C_{3-10}$-cycloalkyl; aryl; or 5 or 6-membered heteroaryl; and/or $R^{1'}$ represents H; $CH_3$; or cyclopropyl.

In a more preferred embodiment, represents
(i) —$C_{1-10}$-alkyl which is selected from the group consisting of —$CH_3$; —$CH_2CH_3$; n-propyl and 2-propyl, more preferably —$CH_3$ or 2-propyl; or
(ii) —$C_{3-10}$-cycloalkyl which is selected from the group consisting of cyclopropyl and cyclobutyl; or
(iii) —$C_{1-6}$-alkylene-$C_{3-10}$-cycloalkyl which is selected from the group consisting of —$CH_2$-cyclopropyl and —$CH_2$-cyclobutyl; or
(iv) aryl which is selected from the group consisting of phenyl and benzodioxanyl; or
(v) 5 or 6-membered heteroaryl which is selected from the group consisting of pyridinyl and pyrazolyl;
and preferably $R^{1'}$ represents H.

In another preferred embodiment, $R^1$ and $R^{1'}$ together with the carbon atom to which they are bound form a $C_{3-10}$-cycloalkyl; or 3 to 7 membered heterocycloalkyl; more preferably $C_{3-10}$-cycloalkyl; still more preferably cyclopropyl and cyclopentyl; most preferably cyclobutyl.

In the compound of the invention according to any of general formulas (I) to (XVII) $R^2$ represents aryl; 5 or 6-membered heteroaryl; —C(=O)—$C_{1-10}$-alkyl; —C(=O)—O—$C_{1-10}$-alkyl; —C(=O)—$C_{3-10}$-cycloalkyl; —C(=O)—$C_{1-6}$-alkylene-$C_{3-10}$-cycloalkyl; —C(=O)—O—$C_{3-10}$-cycloalkyl; —C(=O)-(3 to 7 membered heterocycloalkyl); —C(=O)—$C_{1-6}$-alkylene-(3 to 7 membered heterocycloalkyl); —C(=O)—O-(3 to 7 membered heterocycloalkyl); —C(=O)-aryl; —C(=O)—$C_{1-6}$-alkylene-aryl; —C(=O)—O-aryl; —C(=O)-(5 or 6-membered heteroaryl); —C(=O)—$C_{1-6}$-alkylene-(5 or 6-membered heteroaryl); —C(=O)—O-(5 or 6-membered heteroaryl); —S(=O)$_{1-2}$—$C_{1-10}$-alkyl; —S(=O)$_{1-2}$—$C_{3-10}$-cycloalkyl; —S(=O)$_{1-2}$—$C_{1-6}$-alkylene-$C_{3-10}$-cycloalkyl; —S(=O)$_{1-2}$-(3 to 7 membered heterocycloalkyl); —S(=O)$_{1-2}$—$C_{1-6}$-alkylene-(3 to 7 membered heterocycloalkyl); —S(=O)$_{1-2}$-aryl; —S(=O)$_{1-2}$—$C_{1-6}$-alkylene-aryl; —S(=O)$_{1-2}$-(5 or 6-membered heteroaryl); or —S(=O)$_{1-2}$—$C_{1-6}$-alkylene-(5 or 6-membered heteroaryl).

In a preferred embodiment, $R^2$ represents 5 or 6-membered heteroaryl; —C(=O)—$C_{1-10}$-alkyl; —C(=O)—O—$C_{1-10}$-alkyl; —C(=O)—$C_{3-10}$-cycloalkyl; —C(=O)-aryl; —C(=O)-(5 or 6-membered heteroaryl); —S(=O)$_2$—$C_{1-10}$-alkyl; or —S(=O)$_2$—$C_{3-10}$-cycloalkyl; more preferably 5 or 6-membered heteroaryl; —C(=O)—$C_{1-10}$-alkyl; —C(=O)—O—$C_{1-10}$-alkyl; —C(=O)-(5 or 6-membered heteroaryl); or —S(=O)$_2$—$C_{3-10}$-cycloalkyl.

In another preferred embodiment, $R^2$ represents
(i) 5 or 6-membered heteroaryl, wherein said 5- to 6-membered heteroaryl is selected from the group consisting of thiazolyl, pyrimidinyl; pyrazolyl, oxazolyl, oxadiazolyl, isoxazolyl, isothiazolyl, wherein in each case said 5- to 6-membered heteroaryl is unsubstituted or mono- or disubstituted with substituents selected from the group consisting of —F, —Cl, —Br, —$CH_3$, —$CF_3$, —CN, =O, and —$OCH_3$;
(ii) —C(=O)—$C_{1-10}$-alkyl, unsubstituted or mono- or disubstituted with substituents selected from the group consisting of —F, —Cl, and —Br;
(iii) —C(=O)—O—$C_{1-10}$-alkyl, wherein said —$C_{1-10}$-alkyl is unsubstituted and is selected from the group consisting of methyl, ethyl, n-propyl, 2-propyl, n-butyl, 2-butyl, and tert-butyl;
(iv) —C(=O)—(5- to 6-membered heteroaryl), wherein said 5- to 6-membered heteroaryl is selected from the group consisting of thiazolyl, pyrazolyl, oxazolyl and 1-oxa-2,4-diazolyl, 1,2,5-oxadiazolyl, isoxazolyl, isothiazolyl, wherein in each case said 5- to 6-membered heteroaryl is unsubstituted or mono- or disubstituted with substituents selected from the group consisting of —F, —Cl, —Br, —$CH_3$, —$CF_3$, —CN, =O, and —$OCH_3$; or
(v) —S(=O)$_2$-cyclopropyl, unsubstituted.

In the compound of the invention according to any of general formulas (I) to (XVII) $R^{2'}$ represents H.

In another preferred embodiment, $R^2$ and $R^{2'}$ together with the carbon atom to which they are bound form a $C_{3-10}$-cycloalkyl or 3 to 7 membered heterocycloalkyl; more preferably 3 to 7 membered heterocycloalkyl; still more preferably pyrrolidinone.

In the compound of the invention according to any of general formulas (I) to (XVII) $R^3$ and $R^{3'}$ independently from one another represent H; F; Cl; —$C_{1-10}$-alkyl; —$C_{3-6}$-cycloalkyl; —$C_{1-6}$-alkylene-$C_{3-6}$-cycloalkyl; 3 to 7 membered heterocycloalkyl; —$C_{1-6}$-alkylene-(3 to 7 membered heterocycloalkyl); —$C_{1-6}$-alkylene-aryl; or —$C_{1-6}$-alkylene-(5 or 6-membered heteroaryl).

In a preferred embodiment, $R^3$ represents H or —$C_{1-10}$-alkyl; and/or $R^{3'}$ represents H or —$C_{1-10}$-alkyl; more pereferably $R^3$ represents H or —$CH_3$; and/or $R^{3'}$ represents H or —$CH_3$; still more preferably, $R^3$ and $R^{3'}$ both represent H.

In another preferred embodiment, $R^3$ and $R^{3'}$ both represent —$C_{3-10}$-alkyl; more preferably —$CH_3$.

In still another preferred embodiment, $R^3$ and $R^{3'}$ together with the carbon atom to which they are bound form a $C_{3-10}$-cycloalkyl; or 3 to 7 membered heterocycloalkyl; more preferably cyclopropyl or cyclobutyl.

In the compound of the invention according to any of general formulas (I) to (XVII) $R^4$ and $R^{4'}$ independently from one another represent H; F; Cl; —$C_{1-10}$-alkyl; —$C_{3-6}$-cycloalkyl; —$C_{1-6}$-alkylene-$C_{3-6}$-cycloalkyl; 3 to 7 membered heterocycloalkyl; —$C_{1-6}$-alkylene-(3 to 7 membered heterocycloalkyl); —$C_{1-6}$-alkylene-aryl; or —$C_{1-6}$-alkylene-(5 or 6-membered heteroaryl).

In a preferred embodiment, $R^4$ represents H or —$C_{1-10}$-alkyl; and/or $R^{4'}$ represents H or —$C_{1-10}$-alkyl; more pereferably $R^4$ represents H or —$CH_3$; and/or $R^{4'}$ represents H or —$CH_3$; still more preferably, $R^4$ and $R^{4'}$ both represent H.

In another preferred embodiment, $R^4$ and $R^{4'}$ both represent —$C_{1-10}$-alkyl; more preferably —$CH_3$.

In the compound of the invention according to any of general formulas (I) to (XVII) L represents bond or —$C_{1-6}$-alkylene-; more preferably bond or —$CH_2$—; still more preferably bond.

In the compound of the invention according to any of general formulas (I) to (XVII)
A represents —$C_{1-10}$-alkyl; —$C_{3-6}$-cycloalkyl; —$C_{1-6}$-alkylene-$C_{3-6}$-cycloalkyl; 3 to 7 membered heterocycloalkyl; or —$C_{1-6}$-alkylene-(3 to 7 membered heterocycloalkyl);
or A represents substructure (S1)

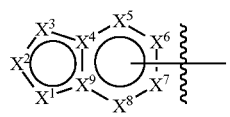

(S1)

wherein
$X^1$, $X^2$ and $X^3$ independently from one another represent CH; $CR^5$; N; NH; $NR^5$; O; or S; wherein at least one of $X^1$, $X^2$ and $X^3$ represents N; NH; $NR^5$; O; or S;
$X^4$ and $X^9$ independently from one another represent C or N;
$X^5$, $X^6$, $X^7$ and $X^8$ in each case independently from one another represent CH; $CR^5$; N; or C which is connected to L; wherein one of $X^5$, $X^6$, $X^7$ and $X^8$ represents C which is connected to L;
or A represents substructure (S2)

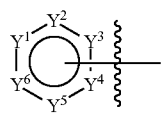

(S2)

wherein
$Y^1$, $Y^2$, $Y^3$, $Y^4$, $Y^5$ and $Y^6$ in each case independently from one another represent CH; $CR^5$; N; or C which is connected to L; wherein one of $Y^1$, $Y^2$, $Y^3$, $Y^4$, $Y^5$ and $Y^6$ represents C which is connected to L.

In a preferred embodiment, A represents substructure (S1). According to this embodiment, preferably $X^5$, $X^6$, $X^7$ and $X^8$ in each case independently from one another represent CH; or C which is connected to L; wherein one of $X^5$, $X^6$, $X^7$ and $X^8$ represents C which is connected to L.

In another preferred embodiment, A represents indolyl; indazolyl; benzisoxazolyl; benzisothiazolyl; benzotriazolyl; imidazopyridinyl; or benzoimidazolyl; in each case unsubstituted or mono- or disubstituted with $R^5$.

In another preferred embodiment, A represents substructure (S2). According to this embodiment, A preferably represents phenyl or pyridinyl; wherein said phenyl and pyridinyl in each case independently from one another are unsubstituted or mono- or disubstituted with substituents selected from the group consisting of —F, —Cl, —Br, —$CF_3$, —CN, —O—$C_{1-10}$-alkyl, —O—$C_{3-10}$-cycloalkyl, —O-(3 to 7 membered heterocycloalkyl), —O-aryl or —O-(5 or 6-membered heteroaryl).

In still another preferred embodiment, A represents —$C_{1-10}$-alkyl which is selected from the group consisting of methyl, ethyl, n-propyl, 2-propyl, n-butyl, isobutyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl and n-hexyl; more preferably methyl, ethyl, n-propyl, 2-propyl, n-butyl, isobutyl, sec-butyl and tert-butyl; most preferably isobutyl.

In a particularly preferred embodiment, A represents isobutyl; phenyl; indolyl; or indazolyl in each case unsubstituted or mono- or disubstituted with substituents independently of one another selected from the group consisting of —F; —Cl; —Br; —$C_{1-4}$-alkyl; —C(=O)—$C_{1-4}$-alkyl; —$OC_{1-4}$-alkyl; phenyl; —O-phenyl; pyridinyl; N-methylpyridinone; and —S(=O)$_2$—$C_{1-4}$-alkyl;
wherein phenyl is unsubstituted or mono- or disubstituted with substituents selected from the group consisting of —F, —Cl, —Br, —$CH_3$, —$CF_3$, —CN, cyclopropyl and —$OCH_3$.

In the compound of the invention according to any of general formulas (I) to (XVII) $R^5$ represents H; F; Cl; —$C_{3-6}$-cycloalkyl; —$C_{1-6}$-alkylene-$C_{3-6}$-cycloalkyl; 3 to 7 membered heterocycloalkyl; —$C_{1-6}$-alkylene-(3 to 7 membered heterocycloalkyl); aryl; —$C_{1-6}$-alkylene-aryl; 5 or 6-membered heteroaryl; —$C_{1-6}$-alkylene-(5 or 6-membered heteroaryl); —C(=O)—$C_{1-10}$-alkyl; —C(=O)—$C_{3-10}$-cycloalkyl; —C(=O)-(3 to 7 membered heterocycloalkyl); —O—$C_{1-10}$-alkyl; —O—$C_{3-6}$-cycloalkyl; —O-(3 to 7 membered heterocycloalkyl); —O-aryl; —O-(5 or 6-membered heteroaryl); —S(=O)$_{1-2}$—$C_{1-10}$-alkyl; —S(=O)$_{1-2}$—$C_{3-10}$-cycloalkyl; —S(=O)$_{1-2}$-(3 to 7 membered heterocycloalkyl); —S(=O)$_{1-2}$-aryl; or —S(=O)$_{1-2}$-(5 or 6-membered heteroaryl).

In a preferred embodiment, $R^5$ represents H; F; Cl; —$C_{1-10}$-alkyl; —C(=O)—$C_{1-10}$-alkyl; —O—$C_{1-10}$-alkyl; —S(=O)$_{1-2}$—$C_{1-10}$-alkyl; —$C_{3-6}$-cycloalkyl; 3 to 7 membered heterocycloalkyl; aryl; —O-aryl; 5 or 6-membered heteroaryl; or —S(=O)$_{1-2}$—$C_{1-10}$-alkyl.

Particularly preferably, $R^5$ represents —H; —F; —Cl; —Br; —$C_{1-4}$-alkyl; —C(=O)—$C_{1-4}$-alkyl; —$OC_{1-4}$-alkyl; phenyl; —O-phenyl; pyridinyl; N-methylpyridinone; and —S(=O)$_2$—$C_{1-4}$-alkyl;
wherein phenyl is unsubstituted or mono- or disubstituted with substituents selected from the group consisting of —F, —Cl, —Br, —$CH_3$, —$CF_3$, —CN, cyclopropyl and —$OCH_3$.

In a particularly preferred embodiment of the invention according to any of general formulas (I) to (XVII)
(i) $R^1$ represents —$C_{1-10}$-alkyl; —$C_{3-10}$-cycloalkyl; —$C_{1-6}$-alkylene-$C_{3-10}$-cycloalkyl; aryl; or 5 or 6-membered heteroaryl; and $R^{1'}$ represents H; $CH_3$ or cyclopropyl; or R' and R^{1'} together with the carbon atom to which they are bound form cyclobutyl; and/or
(ii) R² represents 5 or 6-membered heteroaryl; —C(=O)—C$_{1-10}$-alkyl; —C(=O)—O—C$_{1-10}$-alkyl; —C(=O)-(5 or 6-membered heteroaryl); or —S(=O)$_2$—C$_{3-10}$-cycloalkyl; and R^{2'} represents H; or R² and R^{2'} together with the carbon atom to which they are bound form pyrrolidinone; and/or
(iii) A represents isobutyl; phenyl; indolyl; or indazolyl in each case unsubstituted or mono- or disubstituted with substituents independently of one another selected from the group consisting of —F; —Cl; —Br; —C$_{1-4}$-alkyl; —C(=O)—C$_{1-4}$-alkyl; —OC$_{1-4}$-alkyl; phenyl; —O-phenyl; pyridinyl; N-methylpyridinone; and —S(=O)$_2$—C$_{1-4}$-alkyl;
wherein phenyl is unsubstituted or mono- or disubstituted with substituents selected from the group consisting of —F, —Cl, —Br, —CH$_3$, —CF$_3$, —CN, cyclopropyl and —OCH$_3$; and/or
(iv) R³ represents H or CH$_3$; and/or
(v) R^{3'} represents H or CH$_3$; and/or
(vi) R⁴ represents H or CH$_3$; and/or
(vii) R^{4'} represents H or CH$_3$; and/or
(viii) L represents CH$_2$ or bond.

In a preferred embodiment, the compound according to the invention is selected from the group consisting of 1 N-[rac-(2S,3R)-2-(2,3-Dihydro-[1,4]benzodioxin-6-yl)-1-(1H-indol-4-yl-methyl)-pyrrolidin-3-yl]-cyclopropanesulfonic acid amide
2 2,2-Difluoro-N-[rac-(2R,3 S)-2-phenyl-1-(1-pyridin-4-yl-1H-indazol-5-yl)-pyrrolidin-3-yl]-propionamide
3 N-[rac-(2S,3R)-2-Cyclopropyl-1-[1-(4-fluorophenyl)-1H-indazol-5-yl]-pyrrolidin-3-yl]-2,2-difluoro-propionamide
4 N-[rac-(2S,3R)-2-(2,3-Dihydro-[1,4]benzodioxin-6-yl)-1-[(3-methoxyphenyl)-methyl]-pyrrolidin-3-yl]-2,2-difluoro-propionamide
5 N-[rac-(2R,3 S)-2-(2,3-Dihydro-[1,4]benzodioxin-6-yl)-1-[(5-fluoro-1H-indol-7-yl)-methyl]-pyrrolidin-3-yl]-cyclopropanesulfonic acid amide
6 N-[rac-(2R,3 S)-2-(2,3-Dihydro-[1,4]benzodioxin-6-yl)-1-(2-methyl-propyl)-pyrrolidin-3-yl]-2,2,2-trifluoro-acetamide
7 6-(2,3-Dihydro-[1,4]benzodioxin-6-yl)-7-[1-(4-fluorophenyl)-1H-indazol-5-yl]-1,7-diazaspiro[4.4]nonan-2-one
8 N-[(2R,3 S)-2-Cyclopropyl-1-[1-(4-fluorophenyl)-1H-indazol-5-yl]-pyrrolidin-3-yl]-2,2-difluoro-propionamide
9 N-[rac-(2R,3R)-2-(Cyclopropyl-methyl)-1-[1-(4-fluorophenyl)-1H-indazol-5-yl]-pyrrolidin-3-yl]-2,2-difluoro-propionamide
10 N-[rac-(2R,3 S)-2-(2,3-Dihydro-[1,4]benzodioxin-6-yl)-1-(1H-indazol-4-yl-methyl)-pyrrolidin-3-yl]-cyclopropanesulfonic acid amide
11 N-[rac-(2R,3 S)-2-Phenyl-1-(1-pyridin-4-yl-1H-indazol-5-yl)-pyrrolidin-3-yl]-cyclopropanecarboxylic acid amide
12 5-Methyl-N-[rac-(2R,3 S)-1-[1-(1-methyl-6-oxo-1H-pyridin-3-yl)-1H-indazol-5-yl]-2-phenyl-pyrrolidin-3-yl]-[1,2,4]oxadiazole-3-carboxylic acid amide
13 2,2-Difluoro-N-[rac-(2R,3 S)-1-[1-(4-fluorophenyl)-1H-indazol-5-yl]-2-methyl-pyrrolidin-3-yl]-propionamide
14 N-[rac-(2R,3 S)-2-(2,3-Dihydro-[1,4]benzodioxin-6-yl)-1-[(1-methyl-1H-indol-4-yl)-methyl]-pyrrolidin-3-yl]-cyclopropanesulfonic acid amide
15 N-[rac-(2R,3 S)-2-(2,3-Dihydro-[1,4]benzodioxin-6-yl)-1-[(1-methylsulfonyl-1H-indol-4-yl)-methyl]-pyrrolidin-3-yl]-cyclopropanesulfonic acid amide
16 2,2-Difluoro-N-[rac-(2R,3R)-1-[1-(4-fluorophenyl)-1H-indazol-5-yl]-2-(1-methyl-1H-pyrazol-4-yl)-pyrrolidin-3-yl]-propionamide
17 2,2-Difluoro-N-[rac-(2R,3 S)-1-[1-(4-fluorophenyl)-1H-indazol-5-yl]-2-isopropyl-pyrrolidin-3-yl]-propionamide
18 N-[rac-(2R,3 S)-1-[1-(1-Methyl-6-oxo-1H-pyridin-3-yl)-1H-indazol-5-yl]-2-phenyl-pyrrolidin-3-yl]-cyclopropanesulfonic acid amide
19 N-[rac-(2R,3R)-2-(Cyclopropyl-methyl)-1-[1-(4-fluorophenyl)-1H-indazol-5-yl]-pyrrolidin-3-yl]-carbamic acid tert-butyl ester
20 N-[2-(6-Methoxy-pyridin-3-yl)-1-[(3-phenoxy-phenyl)-methyl]-pyrrolidin-3-yl]-cyclopropanesulfonic acid amide
21 N-[rac-(2R,3R)-2-Cyclobutyl-1-[1-(4-fluorophenyl)-1H-indazol-5-yl]-pyrrolidin-3-yl]-carbamic acid tert-butyl ester
22 N-[rac-(2R,3 S)-1-[(1-Acetyl-1H-indol-4-yl)-methyl]-2-(2,3-dihydro-[1,4]benzodioxin-6-yl)-pyrrolidin-3-yl]-cyclopropanesulfonic acid amide
23 [rac-(2R,3S)-2-Cyclopropyl-1-[1-(4-fluorophenyl)-1H-indazol-5-yl]-pyrrolidin-3-yl]-thiazol-2-yl-amine
24 [rac-(2R,3S)-2-Cyclopropyl-1-[1-(4-fluorophenyl)-1H-indazol-5-yl]-pyrrolidin-3-yl]-pyrimidin-2-yl-amine
25 N-[rac-(2R,3R)-1-[1-(4-Fluorophenyl)-1H-indazol-5-yl]-2-(1-methyl-1H-pyrazol-4-yl)-pyrrolidin-3-yl]-carbamic acid tert-butyl ester
26 1-Methyl-N-[rac-(2R,3 S)-1-[1-(1-methyl-6-oxo-1H-pyridin-3-yl)-1H-indazol-5-yl]-2-phenyl-pyrrolidin-3-yl]-1H-pyrazole-3-carboxylic acid amide
27 2,2-Difluoro-N-[5-[1-(4-fluorophenyl)-1H-indazol-5-yl]-5-azaspiro[3.4]octan-8-yl]-propionamide
28 N-((2R,3S)-1-(1-(4-fluorophenyl)-1H-indazol-5-yl)-2-phenylpyrrolidin-3-yl)cyclopropanecarboxamide
29 N-((2R,3 S)-1-(1-(4-fluorophenyl)-1H-indazol-5-yl)-2-phenylpyrrolidin-3-yl)methanesulfonamide
30 2,2-difluoro —N-(2R,3 S)-1-(1-(4-fluorophenyl)-1H-indazol-5-yl)-2-phenylpyrrolidin-3-yl)propanamid
31 2,2-difluoro —N-[4rac-(2R,3S)-1-(1-(4-fluorophenyl)-1H-indazol-5-yl)-5,5-dimethyl-2-phenylpyrrolidin-3-yl)]propanamide
32 N-[rac-((2R,3 S)-1-(1-(4-fluorophenyl)-1H-indazol-5-yl)-5,5-dimethyl-2-phenylpyrrolidin-3-yl)]cyclopropanecarboxamide
33 2,2-difluoro-N-[rac-((2R,3S,5S)-1-(1-(4-fluorophenyl)-1H-indazol-5-yl)-5-methyl-2-phenylpyrrolidin-3-yl)]propanamide
34 N-[rac-((2R,3S,5S)-1-(1-(4-fluorophenyl)-1H-indazol-5-yl)-5-methyl-2-phenylpyrrolidin-3-yl)]cyclopropanecarboxamide
35 2,2-difluoro-N-[rac-((2R,3 S,5R)-1-(1-(4-fluorophenyl)-1H-indazol-5-yl)-5-methyl-2-phenylpyrrolidin-3-yl)]propanamide
36 N-[rac-((2R,3 S,5R)-1-(1-(4-fluorophenyl)-1H-indazol-5-yl)-5-methyl-2-phenylpyrrolidin-3-yl)]cyclopropanecarboxamide
in each case in the form of the free compound or a physiologically acceptable salt thereof.

The compounds according to the invention can be synthesized by standard reactions in the field of organic chemistry known to the person skilled in the art or in a manner as described herein (cf. Reaction Schemes below) or analogously. The reaction conditions in the synthesis routes described herein are known to the skilled person and are for some cases also exemplified in the Examples described herein.

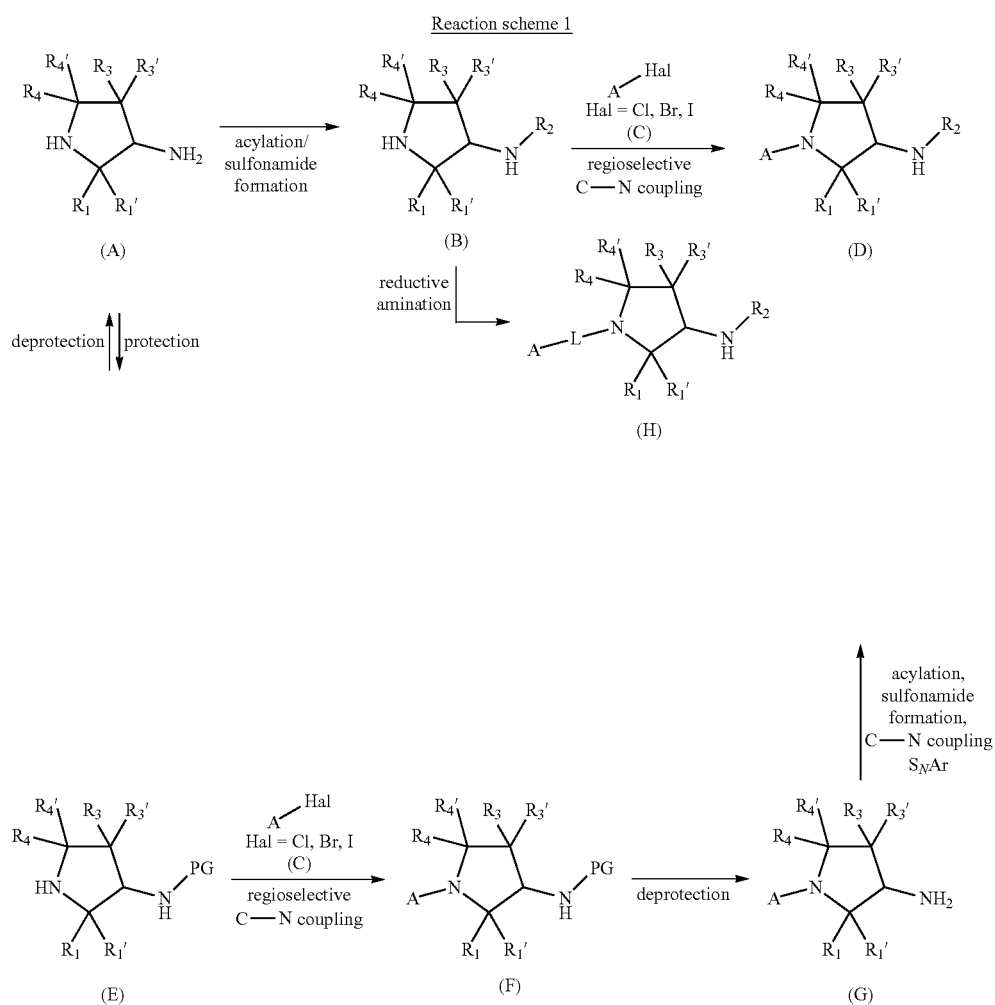

Substituted aryl moieties in compounds of formula (D) and formula (F) are introduced by subjecting amine (B) or amine (E) in a regioselective metal catalyzed C—N coupling reaction with corresponding arylhalides (C), preferred with corresponding arylbromides and aiyliodides. Metal catalyzed C—N coupling reactions are generally known in the art (*Current Organic Synthesis*, 2011, 8, 53). Favorable C—N coupling reactions are palladium catalyzed cross-coupling reactions (*Chem. Rev.*, 2016, 116, 12564). Regioselective C—N couplings with arylhalides are known in the art (*Chem. Sci.*, 2011, 2, 27; *J. Am. Chem. Soc.*, 2001, 123, 7727).

Primaiy amines (A) and (G) are converted to corresponding amides and sulfonamides (acylation and sulfonamide formation) (B) and (D) using commercially available acids (activation of acids using e.g. HATU) or acid chlorides under standard amide coupling reaction conditions (*March's Advanced Organic Chemistry*, 2007, 6th Edition, page 1427-1474). Amines (G) can furthermore be used in C—N coupling reactions or nuleophilic aromatic substitutions (*Current Organic Synthesis*, 2011, 8, 53; *March's Advanced Organic Chemistry*, 2007, 6th Edition, page 853ff).

Introduction of different orthogonal protecting groups PG (e.g. Boc, Cbz) to convert (A) to (E) as well as deprotection of compounds of formula (E) to (A) is well described in the literature (T. W. Green, P. G. M. Wuts, *Protective Groups in Organic Synthesis*, Wiley-Interscience, New York, 1999).

Compounds of the general formula (H) can be prepared from pyrrolidines of the general formula (B) by reductive amination, a process well known in the art (*Adv. Synth. Catal.* 2002, 344, 1037).

Reaction scheme 1.1

Compounds (A) and (E) can be synthesized according to procedures which are described in the literature.

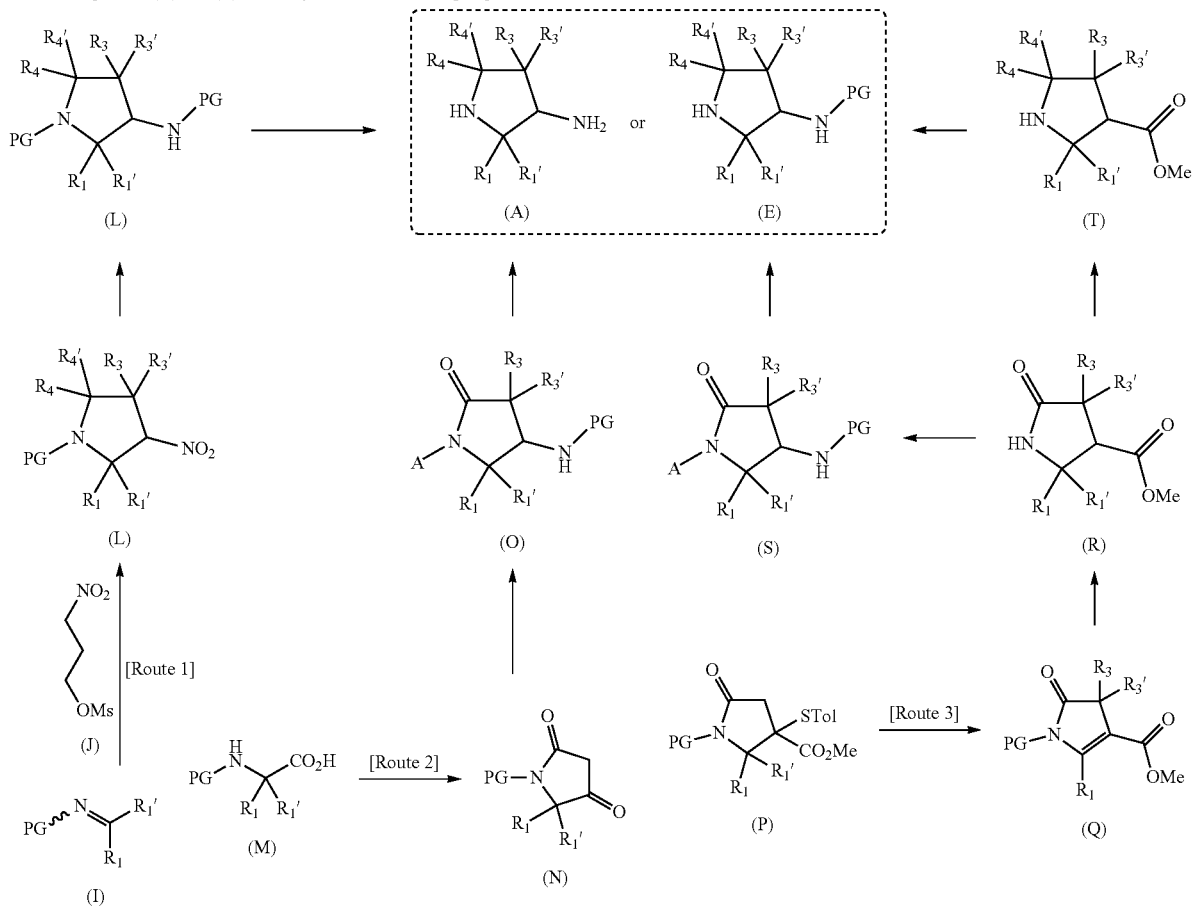

Route 1: Synthesis of nitro-compounds of the general formula (L) using imine (I) and mesylate (J) are known in the art (*Tetrahedron Letters*, 2004, 45, 7, 1373). Reduction of nitro groups (*March's Advanced Organic Chemistry*, 2007, 6th Edition, page 1815f) to give amines of formula (L) and orthogonal removal of one protecting group are well known in the art (T. W. Green, P. G. M. Wuts, *Protective Groups in Organic Synthesis*, Wiley-Interscience, New York, 1999).
Route 2: Cyclization of protected amino acids (M) using Meldrum's acid to compounds of the general formula (N) are known in the art (*Tetrahedron Letters*, 2013, 54, 4821). Conversion to compounds of the general formula (E) takes places via reductive amination (*Adv. Synth. Catal.* 2002, 344, 1037), tioamide formation using preferentially Lawesson's reagent (*Chem. Rev.* 2007, 107, 5210) and reduction as key steps.
Route 3: Synthesis of compounds of formula (P) is described in the literature (*Org. Lett.*), 2007, 9, 4077). Introduction of substituents R3 and R3' can be achieved via alkylation. C-alkylations of pyrrolidinones (*Tetrahedron*, 1999, 55, 13321) and elimination of sulfonium salts (*Tetrahedron Letters* 1983, 24, 4331) are well known in the art. Compounds of formula (A) and (E) via compounds of the formula (S) and (T) can be synthesized using Curtius rearrangement and amide-reduction as key steps from esters of the formula (R). Curtius rearrangement (*Tetrahedron Letters*, 2010, 51, 385) and amide reduction (*Synthesis*, 2018, 50 984) are well known in the art. Favoured reducing reagents include $Zn(OTf)_2$/TMDS and $LiAlH_4$/$AlCl_3$.

The compounds according to the invention can be produced in the manner described here or in an analogous manner.

The compounds according to the invention can be produced in the manner described here or in an analogous manner.

In a preferred embodiment, the compounds according to the invention are modulators of the glucocorticoid receptor. In the sense of the invention, the term "selective modulator of the glucocorticoid receptor (glucocorticoid receptor modulator)" preferably means that the respective compound exhibits in a cellular target engagement assay for agonistic or antagonistic potency on the glucocorticoid receptor an EC50 or IC50 value on the glucocorticoid receptor of at most 15 µM ($10.10^{-6}$ mol/L) or at most 10 µM; more preferably at most 1 µM; still more preferably at most 500 nM ($10^{-9}$ mol/L); yet more preferably at most 300 nM; even more preferably at most 100 nM; most preferably at most 10 nM; and in particular at most 1 nM. In a preferred embodiment, the compound according to the invention exhibits in a cellular target engagement assay for agonistic or antagonistic potency on the glucocorticoid receptor an EC50 or IC50 value on the glucocorticoid receptor in the range of from 1 µM to 15 µM, more preferably from 100 nM to 1 µM, most preferably below 100 nM.

The person skilled in the art knows how to test compounds for modulation (agonistic or antagonistic) of the activity of the glucocorticoid receptor. Preferred target engagement assays for testing compounds for their agonistic or antagonistic potency (EC50, IC50) on the glucocorticoid receptor are described herein below:

Glucocorticoid Receptor Cell-Based Assays

Potential selective glucocorticoid receptor modulators of this intervention can be tested for modulation of the activity of the glucocorticoid receptor using cell-based assays. These assays involve a Chinese hamster ovary (CHO) cell line which contains fragments of the glucocorticoid receptor as well as fusion proteins. The glucocorticoid receptor fragments used are capable of binding the ligand (e.g. beclomethasone) to identify molecules that compete for binding with glucocorticoid receptor ligands. In more detail, the glucocorticoid receptor ligand binding domain is fused to the DNA binding domain (DBD) of the transcriptionfactor GAL4 (GAL4 DBD-GR) and is stably integrated into a CHO cell line containing a GAL4-UAS-Luciferase reporter construct. To identify selective glucocorticoid receptor modulators, the reporter cell line is incubated with the molecules using an 8-point half-log compound dilution curve for several hours. After cell lysis the luminescence that is produced by luciferase after addition of the substrate is detected and EC50 or IC50 values can be calcuated. Engagement of molecules which induce gene expression via glucocortocoid receptor binding to the DNA leads to expression of the luciferase gene under the control of the fusion protein GAL4 DBD-GR and therefore to a dosedependent increase of the luminescence signal. Binding of molecules which repress beclomethasone-induced gene expression of the luciferase gene under the control of the fusion protein GAL4 DBD-GR leads to a dosedependent reduction of the luminescence signal.

In a preferred embodiment, the compound according to the invention exhibits in a cellular target engagement assay for agonistic or antagonistic potency on the glucocorticoid receptor an EC50 or IC50 value on the glucocorticoid receptor of at most 1 µM ($10^{-6}$ mol/L); still more preferably at most 500 nM ($10^{-9}$ mol/L); yet more preferably at most 300 nM; even more preferably at most 100 nM; most preferably at most 50 nM; and in particular at most 10 nM or at most 1 nM.

In a preferred embodiment, the compound according to the invention exhibits in a cellular target engagement assay for agonistic or antagonistic potency on the glucocorticoid receptor an EC50 or IC50 value on the glucocorticoid receptor in the range of from 1 µM to 15 µM, more preferably from 100 nM to 1 µM, most preferably below 100 nM.

In a preferred embodiment, the compound according to the invention exhibits in a cellular target engagement assay for agonistic or antagonistic potency on the glucocorticoid receptor an EC50 or IC50 value on the glucocorticoid receptor in the range of from 0.1 nM ($10^{-9}$ mol/L) to 1000 nM; still more preferably 1 nM to 800 nM; yet more preferably 1 nM to 500 nM; even more preferably 1 nM to 300 nM; most preferably 1 nM to 100 nM; and in particular 1 nM to 80 nM.

Preferably, the compounds according to the invention are useful as selective modulators of the glucocorticoid receptor.

Therefore, the compounds according to the invention are preferably useful for the in vivo treatment or prevention of diseases in which participation of the glucocorticoid receptor is implicated.

The invention therefore further relates to a compound according to the invention for use in the modulation of glucocorticoid receptor activity.

Therefore, another aspect of the invention relates to a compound according to the invention for use in the treatment and/or prophylaxis of a disorder which is mediated at least in part by the glucocorticoid receptor. Still another aspect of the invention relates to a method of treatment of a disorder which is mediated at least in part by the glucocorticoid receptor comprising the administration of a therapeutically effective amount of a compound according to the invention to a subject in need thereof, preferably a human.

A further aspect of the invention relates to the use of a compound according to the invention as medicament.

Another aspect of the invention relates to a pharmaceutical dosage form comprising a compound according to the invention. Preferably, the pharmaceutical dosage form comprises a compound according to the invention and one or more pharmaceutical excipients such as physiologically acceptable carriers, additives and/or auxiliary substances; and optionally one or more further pharmacologically active ingredient. Examples of suitable physiologically acceptable carriers, additives and/or auxiliary substances are fillers, solvents, diluents, colorings and/or binders. These substances are known to the person skilled in the art (see H. P. Fiedler, Lexikon der Hilfsstoffe fur Pharmazie, Kosmetik and angrenzende Gebiete, Editio Cantor Aulendoff).

The pharmaceutical dosage form according to the invention is preferably for systemic, topical or local administration, preferably for oral administration. Therefore, the pharmaceutical dosage form can be in form of a liquid, semisolid or solid, e.g. in the form of injection solutions, drops, juices, syrups, sprays, suspensions, tablets, patches, films, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and can also be administered as such.

The pharmaceutical dosage form according to the invention is preferably prepared with the aid of conventional means, devices, methods and processes known in the art. The amount of the compound according to the invention to be administered to the patient may vary and is e.g. dependent on the patients weight or age and also on the type of administration, the indication and the severity of the disorder. Preferably 0.001 to 100 mg/kg, more preferably 0.05 to 75 mg/kg, most preferably 0.05 to 50 mg of a compound according to the invention are administered per kg of the patients body weight.

The glucocorticoid receptor is believed to have potential to modify a variety of diseases or disorders in mammals such as humans These include in particular inflammatory diseases.

Another aspect of the invention relates to a compound according to the invention for use in the treatment and/or prophylaxis of pain and/or inflammation; more preferably inflammatory pain.

A further aspect of the invention relates to a method of treatment of pain and/or inflammation; more preferably inflammatory pain.

The following examples further illustrate the invention but are not to be construed as limiting its scope.

Synthesis of 2,2-difluoro-N-(trans-2-phenylpyrrolidin-3-yl)propanamide (intermediate A1)

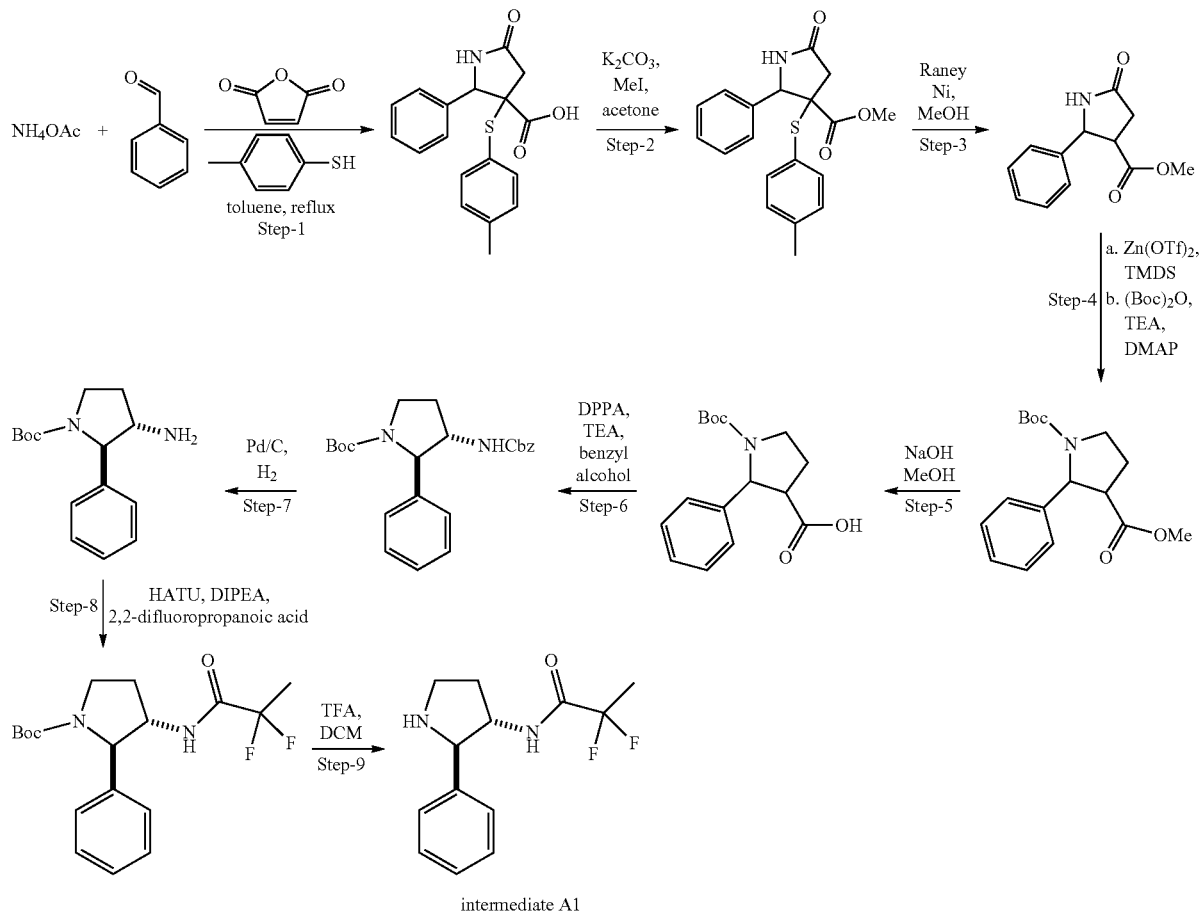

intermediate A1

Step 1: Maleic anhydride (9.8 g, 100 mmol, 1.0 eq.), p-thiocresol (12.4 g, 100 mmol, 1.0 eq.), ammonium acetate (7.8 g, 100 mmol, 1.0 eq.) and benzaldehyde (10 mL, 100 mmol, 1.0 eq.) were put in a sealed tube and 100 mL toluene was added. The reaction mixture was stirred at RT for 1 h and then stirred at 150° C. for 16 h. After cooling to RT, the solvent was evaporated under reduced pressure, and the residue was basified with sat. $NaHCO_3$ solution and was extracted with DCM. The aqueous layer was acidified with 2N HCl under ice cooling and the crude product was extracted twice with EtOAc. The combined organic layers were washed with brine, dried over $Na_2SO_4$, filtered and concentrated to get crude 5-oxo-2-phenyl-3-(p-tolylthio) pyrrolidine-3-carboxylic acid (10.0 g, crude).

Step 2: To a stirred solution of crude 5-oxo-2-phenyl-3-(p-tolylthio)pyrrolidine-3-carboxylic acid (10.0 g, 30.58 mmol, 1.0 eq.) in acetone (100 mL), potassium carbonate (16.8 g, 122.32 mmol, 4.0 eq.) and methyl iodide (7.6 ml, 122.32 mmol, 4.0 eq.) were added at 0° C., and the reaction was stirred for 16 hat RT. The solvent was removed under reduced pressure, and the residue was partitioned between DCM and water. The aqueous layer was extracted twice with DCM. The combined organic layers were washed with brine, dried over Nae $SO_4$, filtered, and concentrated. The crude product was purified by column chromatography (100-200 silica gel, 50% EtOAc:hexanes) to give methyl 5-oxo-2-phenyl-3-(p-tolylthio)pyrrolidine-3-carboxylate (4.0 g, 38%) as an off-white solid.

Step 3: To a stirred solution of methyl5-oxo-2-phenyl-3-(p-tolylthio)pyrrolidine-3-carboxylate (4.0 g, 11.73 mmol, 1.0 eq.) in EtOH:THF (100 mL, 2:1), Raney Nickel (1 g) was added and the reaction mixture was stirred for 2 h at RT. After completion, the reaction mixture was filtered through a celite bed and the celite bed was washed 2-3 times with EtOAc. The combined organic layers were concentrated and the crude was purified by column chromatography (100-200 silica gel, 50% EtOAc:hexanes) to afford methyl 5-oxo-2-phenylpyrrolidine-3-carboxylate (2.2 g, 88%, syn:anti, 1:1 mixture) as an off-white solid.

Step 4: To a stirred solution of methyl 5-oxo-2-phenylpyrrolidine-3-carboxylate (11.0 g, 50.2 mmol, 1.0 eq.) in toluene (200 mL) was added zinc(II)triflate (18.23 g, 50.2 mmol, 1.0 eq.) followed by TMDS (20.2 g, 150.6 mmol, 3.0 eq). The reaction mixture was then heated to 110° C. for 24 hours under an inert atmosphere. After completion of the reaction (monitored by TLC, solvent system=30% EA in hexane, Rf-0.3), the reaction mixture was cooled to ambient temperature followed by the addition of $Boc_2O$ (21.9 g, 100.4 mmol, 2.0 eq.) and triethylamine (15.2 g, 150.6 mmol, 3.0 eq.). The mixture was then stirred for 16 hours. After completion of the reaction (monitored by TLC, solvent system=20% EA in hexane, Rf-0.5), the reaction mixture was diluted with ethyl acetate (250 mL), washed with water (3×100 mL), dried over Na$_2$SO$_4$ and concentrated under reduced pressure. The crude compound was then purified by column chromatography using 230-400 silica and 15% ethyl acetate in hexane as eluting solvent to afford 1-(tert-butyl) 3-methyl 2-phenylpyrrolidine-1,3-dicarboxylate (6.0 g, 39%).

Step 5: To a stirred solution of 1-(tert-butyl) 3-methyl 2-phenylpyrrolidine-1,3-dicarboxylate (5.9 g, 19.32 mmol, 1.0 eq.) in MeOH (120 mL) was added 2 N NaOH solution (24 mL) and the reaction mixture was stirred at 80° C. for 16 h. After completion of the reaction (monitored by TLC, TLC system 5% methanol in DCM, Rf-0.1), the reaction mixture was concentrated and acidified with NaHSO$_4$ solution to obtain a solid, which was filtered off and washed with diethyl ether and dried under vacuum to afford 1-(tert-butoxycarbonyl)-2-phenylpyrrolidine-3-carboxylic acid (4.0 g, 71%) as a white solid.

Step 6: To a stirred solution of 1-(tert-butoxycarbonyl)-2-phenylpyrrolidine-3-carboxylic acid (1.5 g, 5.15 mmol, 1.0 eq.) in toluene (20 mL) were added TEA (0.8 mL, 5.41 mmol, 1.05 eq.) and DPPA (1.3 mL, 6.177 mmol, 1.2 eq.) and the reaction mixture was stirred at 90° C. for 30 min. After 30 min, benzyl alcohol (1.1 mL, 10.30 mmol, 2.0 eq.) was added to the reaction mixture and the mixture was heated to reflux for 16 h. After completion of the reaction (monitored by TLC, TLC system 30% EtOAc/Hexane, Rf-0.3), the reaction mixture was concentrated under reduced pressure, diluted with ethyl acetate (150 mL), washed with water (2×100 mL), dried over anh. Na$_2$SO$_4$ and concentrated under reduced pressure to get the crude compound which was purified by column chromatography (230-400 mesh silica gel; 15% EtOAc/Hexane) to afford tert-butyl trans-3-(ftbenzyloxy)carbonyftamino)-2-phenylpyrrolidine-1-carboxylate (0.7 g, 34%).

Step 7: To a stirred solution of tert-butyl trans-3-(ftbenzyloxy)carbonypamino)-2-phenylpyrrolidine-1-carboxylate (0.6 g, 1.51 mmol, 1.0 eq) in methanol:THF (40 mL, 2:1), Pd/C (0.3 g, 10% moist) was added and the reaction was stirred under hydrogen balloon pressure for 2 h at ambient temperature. After completion (monitored by TLC, TLC system 5% methanol in DCM, Rf-0.2), the reaction mixture was filtered through a celite bed and the celite bed was washed 2-3 times with THF. The filtrate was concentrated to get tert-butyl trans-3-amino-2-phenylpyrrolidine-1-carboxylate as a brown gum (0.42 g, 96%).

Step 8: To a stirred solution of 2,2-difluoropropanoic acid (0.1 g, 0.915 mmol, 1.2 eq.) in DMF (5 mL), HATU (0.58 g, 1.524 mmol, 2.0 eq.), DIPEA (0.62 mL, 3.811 mmol, 5.0 eq.) and tert-butyl trans-3-amino-2-phenylpyrrolidine-1-carboxylate (0.2 g, 0.76 mmol, 1.0 eq.) were added at 0° C. and the reaction was then stirred at ambient temperature for 16 h. After completion of the reaction (monitored by TLC, TLC system 5% methanol in DCM, Rf-0.3), the reaction mixture was diluted with ethyl acetate (50 mL), washed with ice cold water (3×25 mL), dried over Na$_2$SO$_4$ and concentrated to get the crude compound which was purified by column chromatography (230-400 mesh silica gel; 0 to 2% MeOH-DCM) to afford tert-butyl trans-3-(2,2-difluoropropanamido)-2-phenylpyrrolidine-1-carboxylate (0.16 g, 58%).

Step 9: To a stirred solution of tert-butyl trans-3-(2,2-difluoropropanamido)-2-phenylpyrrolidine-1-carboxylate (0.16 g, 0.440 mmol, 1.0 eq.) in DCM (5 mL) was added TFA (1.5 mL) dropwise at 0° C. and the mixture was stirred for 2 h at ambient temperature. The reaction mixture was then concentrated under reduced pressure to obtain a residue which was azeotroped with DCM and washed with Et$_2$O to afford 2,2-difluoro-N-(trans-2-phenylpyrrolidin-3-yl)propanamide (0.1 g, 89%) as an off-white solid.

Synthesis of tert-butyl (trans-2-cyclopropyl-1-(1-(4-fluorophenyl)-1H-indazol-5-yl)pyrrolidin-3-yl)cathamate (intermediate A2)

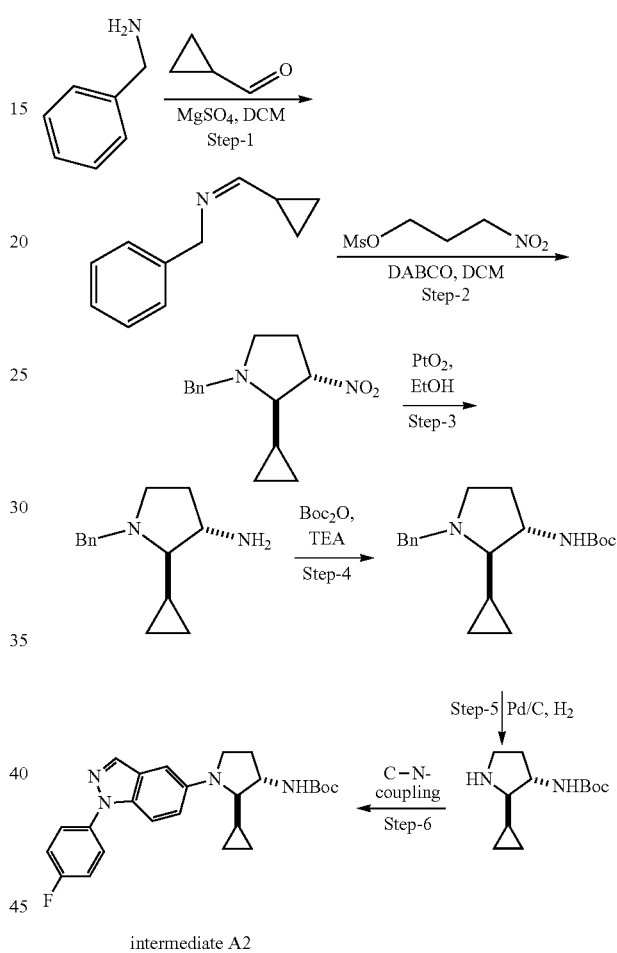

intermediate A2

Step 1: To a stirred solution of cyclopropane carboxaldehyde (5.0 g, 71.42 mmol, 1.0 eq.) in DCM (525 mL) benzylamine (7.64 g, 71.42 mmol, 1.0 eq.) was added along with anhydrous MgSO$_4$ (68.5 g, 571.42 mmol, 8.0 eq.) and the mixture was stirred for 48 hours. The reaction mixture was then filtered through a celite bed and the solvent was distilled off to reduce the amount of solvent down to approx. half of its initial volume at low temperature (below 30° C.). This mixture was used in the next step.

Step 2: To a stirred solution of crude N-benzyl-1-cyclopropylmethanimine (11.3 g, 71.42 mmol, 1.0 eq.) in DCM (200 mL), 3-nitropropylmethanesulfonate (13.0 g, 71.42 mmol, 1.0 eq.) in DCM was added along with DABCO (1.0 g, 8.9 mmol) and scandium(III)triflate (1.0 g, 2.0 mmol). The resulting mixture was stirred for 72 hours. The reaction mixture was then diluted with DCM (50 mL), washed with water (20 mL×3), brine (50 mL) and finally dried over anhydrous sodium sulfate. The organic layer was concentrated under reduced pressure to get the crude compound which was purified by column chromatography (silica gel 230-400) using 2% ethyl acetate/hexane (Rf value 0.5 at 10% EA-hexane) as eluent to obtain trans-1-benzyl-2-cyclopropyl-3-nitropyrrolidine (6.7 g, light yellow liquid, 37%)

Step 3: A stirred solution of trans-1-benzyl-2-cyclopropyl-3-nitropyrrolidine (6.7 g, 27.23 mmol, 1.0 eq.) in EtOH (250 mL) was deoxygenated for 10 minutes, then platinum oxide (2.16 g, 10% by weight) was added and the mixture was again degassed thoroughly with argon and was then stirred for 12 hours under hydrogen balloon pressure. The reaction mixture was then filtered through a celite bed and was then concentrated under reduced pressure to obtain crude trans-1-benzyl-2-cyclopropylpyrrolidin-3-amine (5.7 g, colorless liquid, 95%) which was used in the next step without further purification.

Step 4: To a stirred solution of crude trans-1-benzyl-2-cyclopropylpyrrolidin-3-amine (0.6 g, 2.77 mmol, 1.0 eq.) in DCM (20 mL) was added triethyl amine (0.75 mL, 5.55 mmol, 2.0 eq.) followed by addition of $Boc_2O$ (0.91 g, 4.17 mmol, 1.5 eq.) at 0° C. The mixture was stirred for 3 hours, and was then diluted with DCM (50 mL), washed with water (30 mL×2), dried over anhydrous sodium sulfate and evaporated under reduced pressure and triturated with hexane to afford tert-butyl (trans-1-benzyl-2-cyclopropylpyrrolidin-3-yl)carbamate (0.7 g, white solid, 80%).

Step 5: A stirred solution of tert-butyl (trans-1-benzyl-2-cyclopropylpyrrolidin-3-yl)carbamate (0.6 g, 1.84 mmol, 1.0 eq.) in MeOH (60 mL) was deoxygenated for 10 minutes, then Pd/C (0.12 g, 20% by weight) was added and the mixture was again degassed thoroughly with argon and was then stirred for one hour under hydrogen balloon pressure. The reaction mixture was then filtered through a celite bed and was concentrated under reduced pressure to obtain crude tert-butyl (trans-2-cyclopropylpyrrolidin-3-yl) carbamate (0.4 g, colorless liquid, 92%), which was used in the next step without further purification.

Step 6: To a stirred solution of crude tert-butyl (trans-2-cyclopropylpyrrolidin-3-yl)carbamate (0.15 g, 0.64 mmol, 1.0 eq.) in toluene (5 mL) were added 5-bromo-1-(4-fluorophenyl)-1H-indazole (0.22 g, 0.76 mmol, 1.2 eq.) and $Cs_2CO_3$ (0.42 g, 1.27 mmol, 2.0 eq.) and the mixture was deoxygenated for 15 minutes in a sealed tube. Then 2-dicyclohexylphosphino-2',6'-diisopropoxybiphenyl (RuPhos, 0.013 g, 0.032 mmol, 0.05 eq.) was added and the mixture was deoxygenated for 15 minutes. Then, (RuPhos)palladium (II) phenethylamine chloride (RuPhos Palladacycle, 0.019 g, 0.0327 mmol, 0.05 eq.) was added and the mixture was refluxed at 120° C. for 16 hours. The reaction mixture was then filtered and diluted with ethylacetate. The organic layer was washed with brine, dried over anhydrous $Na_2SO_4$ and evaporated under reduced pressure to get the crude compound which was purified by 230-400 mesh silicagel, using 20% EA-hexane (Rf-value 0.5) as eluent to afford tert-butyl (trans-2-cyclopropyl-1-(1-(4-fluorophenyl)-1H-indazol-5-yl)pyrrolidin-3-yl)carbamate (0.1 g, light yellow solid, 36%).

Synthesis of N-(trans-2-(2,3-dihydrobenzo[b][1,4] dioxin-6-yl)pyrrolidin-3-yl)cyclopropanesulfonamide (intermediate A3)

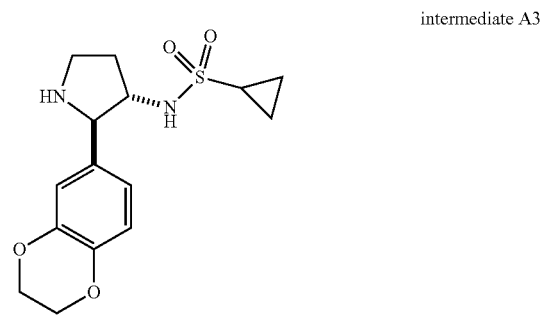 [SMILES: O=S(=O)(N[C@H]1CCN[C@@H]1c1ccc2c(c1)OCCO2)C1CC1]

intermediate A3

Intermediate A3 can be prepared in analogy to the synthesis of intermediate A1 using synthetic variations obvious to the person skilled in the art.

Synthesis of tert-butyl (5-(1-(4-fluorophenyl)-1H-indazol-5-yl)-5-azaspiro[3.4]octan-8-yl)carbamate (intermediate A4)

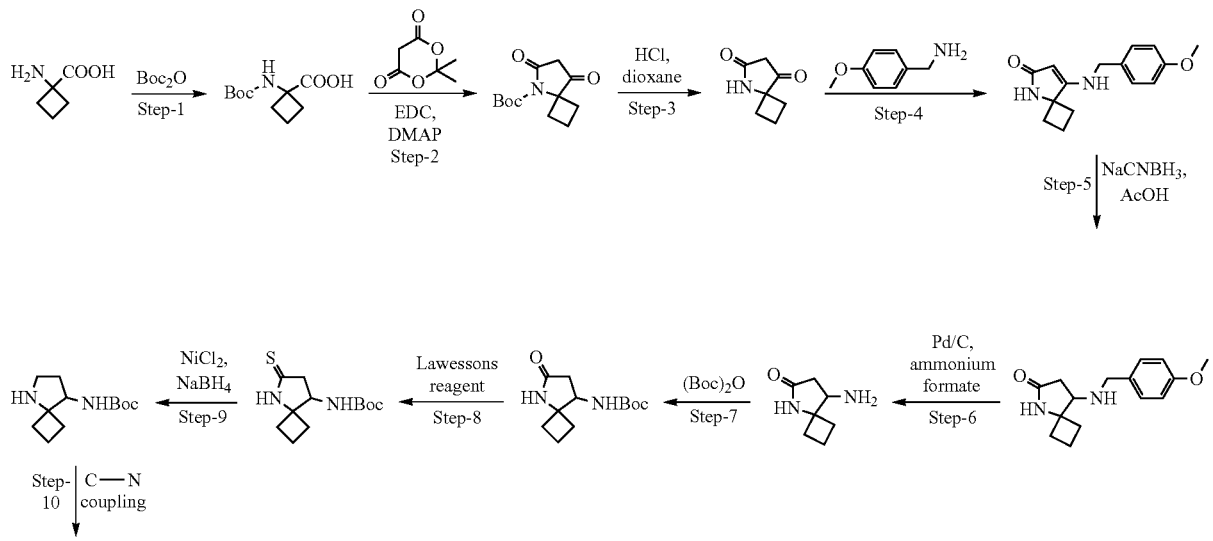

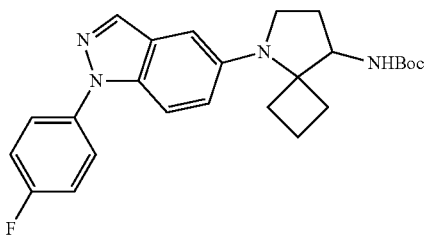

intermediate A4

Step 1: To a stirred solution of 1-aminocyclobutane-1-carboxylic acid (5.0 g, 43.455 mmol) in 0.5N NaOH solution (100 mL) and 1,4-dioxane (100 mL) was added di-tert-butyl-di-carbonate (14.2 g, 65.183 mmol) at 0° C. The reaction mixture was then allowed to warm to ambient temperature and was stirred for 16 h. The reaction mixture was then acidified with 2N HCl solution. The mixture was extracted with ethyl acetate, washed with brine, dried over anhydrous sodium sulphate and concentrated under reduced pressure to afford 1-((tert-butoxycarbonyl)amino)cyclobutane-1-carboxylic acid as a white solid. Yield: 5.8 g, 62%.

Step 2: To a stirred solution of 1-((tert-butoxycarbonyl)amino)cyclobutane-1-carboxylic acid (7.0 g, 32.520 mmol) in DCM (140 mL) were added Meldrum's acid (5.33 g, 35.772 mmol) and DMAP (5.95 g, 48.780 mmol) at 0° C. The reaction mixture was allowed to stirr at that temperature for 30 minutes, then EDC HCl salt (14.96 g, 78.048 mmol) was added and the reaction mixture was stirred at ambient temperature for 20 h. The reaction mixture was then diluted with ethyl acetate, was washed with cold 5% $KHSO_4$ solution, water and brine. The organic layer was then heated to 75° C. for one hour, the mixture was concentrated under reduced pressure and the obtained residue was triturated with diethyl ether to afford tert-butyl 6,8-dioxo-5-azaspiro[3.4]octane-5-calboxylate as an off white solid. Yield 3.5 g, 23%.

Step 3: To a stirred solution of tert-butyl 6,8-dioxo-5-azaspiro[3.4]octane-5-carboxylate (2.5 g, 10.455 mmol) in 1,4-dioxane (25 mL) was added HCl in 1,4-dioxane (25 mL) at 0° C. The reaction was then continued at ambient temperature for 2 hours. The reaction mixture was then concentrated under reduced pressure. The obtained residue was triturated with diethyl ether to afford 5-azaspiro[3.4]octane-6,8-dione as a white solid. Yield: 1.2 g, 83%.

Step 4: To a stirred solution of 5-azaspiro[3.4]octane-6,8-dione (1.2 g, 8.623 mmol) in ethanol (50 mL) and acetic acid (5 mL) was added (4-methoxyphenyl)methanamine (1.18 g, 8.623 mmol) under a nitrogen atmosphere. The reaction was then heated to 80° C. for 3 hours. The reaction mixture was then concentrated under reduced pressure, the obtained residue was basified with 1N NaOH causing the precipitation of an off-white solid. The precipitated solid was filtered off and dried under reduced pressure to afford 8-((4-methoxybenzyl)amino)-5-azaspiro[3.4]oct-7-en-6-one. Yield: 1.6 g, 72%.

Step 5: To a stirred solution of 8-((4-methoxybenzyDamino)-5-azaspiro[3.4]oct-7-en-6-one (1.6 g, 6.193 mmol) in acetic acid (30 mL) was added sodium cyanoborohydride (1.95 g, 30.969 mmol) at 0° C., and the reaction was stirred for one hour. The reaction mixture was then concentrated under reduced pressure; the obtained residue was basified with 2N NaOH and extracted with ethyl acetate. The combined organic layers were washed with water and brine, dried over anhydrous sodium sulphate and concentrated under reduced pressure. The crude compound was purified by column chromatography using neutral aluminium oxide and 1% methanol in DCM as an eluent to afford 8-((4-methoxybenzypamino)-5-azaspiro[3.4]octan-6-one as a white solid. Yield: 1.3 g, 81%.

Step 6: To a stirred solution of 8-((4-methoxybenzypamino)-5-azaspiro[3.4]octan-6-one (2.0 g, 7.682 mmol) in MeOH (50 mL) were added 2N HCl (2.0 mL), ammonium formate (9.69 g, 153.645 mmol) and 10% Palladium on carbon (2.0 g). The reaction mixture was then heated to 80° C. for 18 hours. The reaction mixture was then filtered through a celite bed; the filtrate was concentrated under reduced pressure to afford 8-amino-5-azaspiro[3.4]octan-6-one as a colorless sticky material. Yield: 1.3 g Step 7: To a stirred solution of 8-amino-5-azaspiro[3.4]octan-6-one (1.3 g, 9.273 mmol) in DCM (13 mL) were added TEA (2.8 g, 27.819 mmol) and $Boc_2O$ (2.23 g, 10.200 mmol) at 0° C. The reaction mixture was then stirred at ambient temperature for 14 hours. The reaction mixture was then diluted with DCM, was washed with water and brine, dried over anhydrous sodium sulphate and concentrated under reduced pressure. The obtained residue was purified by column chromatography using neutral aluminium oxide and 1% methanol in DCM as eluent to afford tert-butyl (6-oxo-5-azaspiro[3.4]octan-8-yl)carbamate as a white solid. Yield: 1.5 g, 62%

Step 8: To a stirred solution of tert-butyl (6-oxo-5-azaspiro[3.4]octan-8-yl)carbamate (1.5 g, 6.245 mmol) in toluene (60 mL) was added Lawesson's reagent (1.76 g, 4.371 mmol). The reaction mixture was then heated to 75° C. for four hours. The reaction mixture was then concentrated under reduced pressure and the obtained residue was purified by column chromatography using neutral aluminium oxide and 1% methanol in DCM as an eluent to afford tert-butyl (6-thioxo-5-azaspiro[3.4]octan-8-yl)carbamate as a white solid. Yield: 1.3 g, 81%

Step 9: To a stirred solution of tert-butyl (6-thioxo-5-azaspiro[3.4]octan-8-yl)carbamate (1.2 g, 4.680 mmol) in THF:MeOH (1:1, 120 mL) were added $NiCl_2 \cdot 6\ H_2O$ (8.91 g, 37.447 mmol) and $NaBH_4$ (4.26 g, 112.342 mmol) under a nitrogen atmosphere at 0° C. The reaction was then stirred at that temperature for fifteen minutes. The reaction mixture was filtered and the filtrate was concentrated under reduced pressure. The obtained residue was purified by column chromatography using neutral aluminium oxide and 2% methanol in DCM as an eluent to afford tert-butyl (5-azaspiro[3.4]octan-8-yl)carbamate as a white solid. Yield: 0.7 g, 66%

Step 10: Under a nitrogen atmosphere, tert-butyl (5-azaspiro[3.4]octan-8-yl)carbamate (75.0 mg, 0.331 mmol, 1.0 eq.), 5-bromo-1-(4-fluorophenyl)indazole (193.0 mg. 0.663 mmol, 2.0 eq.) and $Cs_2CO_3$ (323.9 mg, 0.994 mmol, 3.0 eq.) were weighed out into a vial. Then Chloro(2-dicyclohexylphosphino-2',4',6'-triisopropyl-1,1'-biphenyl)[2-(2'-amino-1,1'-biphenyl)]palladium(II) (XPhosG2, 52.2 mg, 0.066 mmol, 0.2 eq.) was added, a stir bar was added, the vial was sealed and purged with nitrogen. Then, 1,4-dioxane (2.8 mL) was added, and the reaction mixture was heated to 95° C. for 16 hours. The solvent was then removed under reduced pressure and the residue was purified via LC to yield 58.0 mg (59%) of tert-butyl (5-(1-(4-fluorophenyl)-1H-indazol-5-yl)-5-azaspiro[3.4]octan-8-yp-cathamate.

Synthesis of (2R,3S)-1-(1-(4-fluorophenyl)-1H-indazol-5-yl)-4,4-dimethyl-2-phenylpyrrolidin-3-amine (intermediate A5)

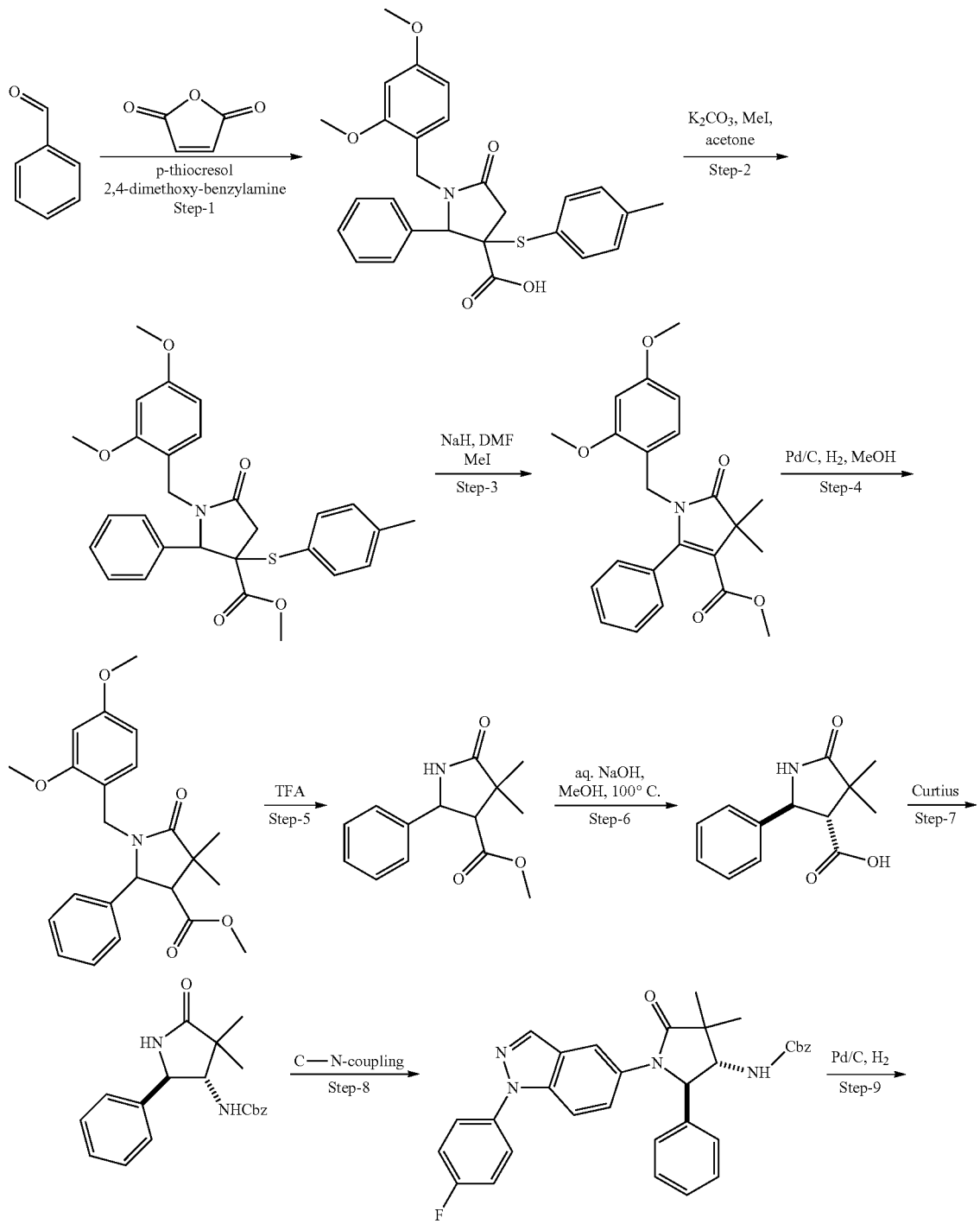

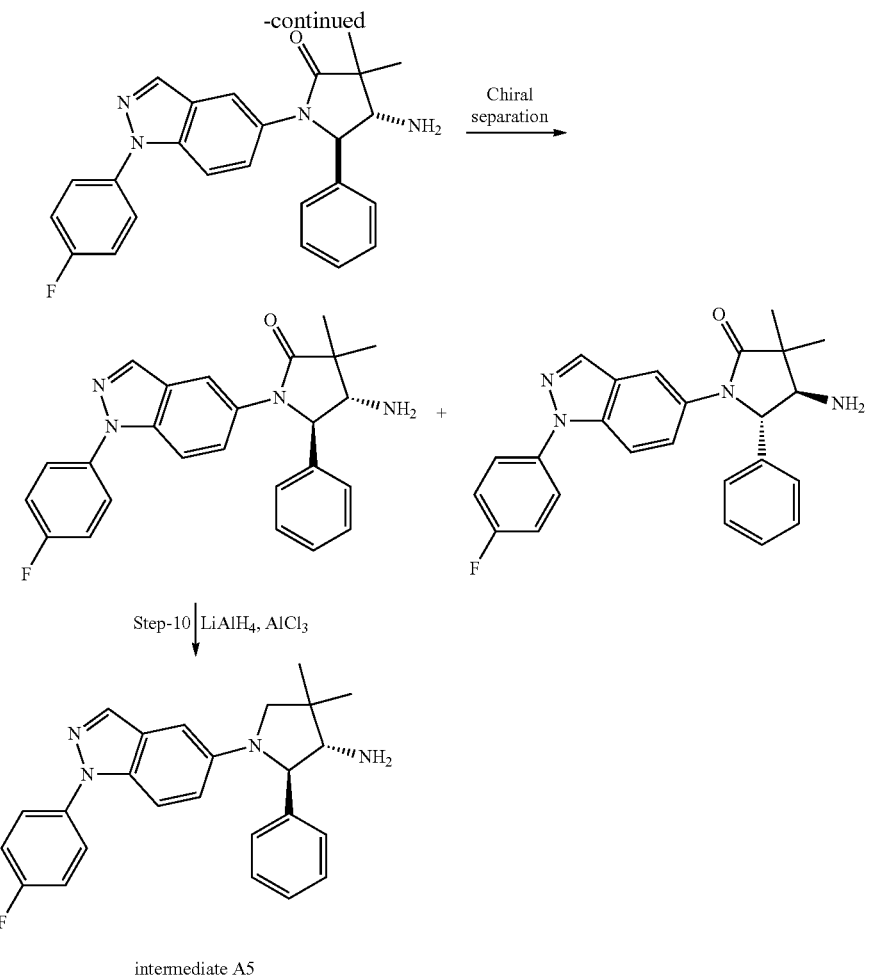

intermediate A5

Step 1: A solution of benzaldehyde (95.18 g, 0.898 mol), 4-methylbenzenethiol (111.37 g, 0.898 mol), maleic anhydride (88.04 g, 0.898 mol) and 2,4-dimethoxybenzylamine (150.00 g, 0.898 mol) in toluene (600 ml) was stirred at ambient temperature for 2 h and was then heated to 120° C. for 16 h. After completion of the reaction (monitored by TLC, mobile phase 5% MeOH-DCM, Rf 0.4) the reaction mixture was cooled to ambient temperature and was concentrated under reduced pressure to obtain the crude product which was triturated with MTBE to afford 1-(2,4-dimethoxy-benzyl)-5-oxo-2-phenyl-3-p-tolylsulfanyl-pyrrolidine-3-carboxylic acid (150.0 g, 35%) as an off white solid.

Step 2: To a suspension of 1-(2,4-dimethoxy-benzyl)-5-oxo-2-phenyl-3-p-tolylsulfanyl-pyrrolidine-3-carboxylic acid (500.0 g, 1.05 mol) in acetone (5 L) was added $K_2CO_3$ (579.0 g, 4.19 mol) followed by methyl iodide (261.0 ml, 4.19 mol). The resulting suspension was stirred at ambient temperature for 16 h. The reaction mixture was then filtered and the filtrate was concentrated. The residue was taken up in EtOAc (1.5 L) and was washed with water. The organic layer was washed with brine, dried over sodium sulfate and was concentrated under reduced pressure to afford 1-(2,4-dimethoxy-benzyl)-5-oxo-2-phenyl-3-p-tolylsulfanyl-pyrrolidine-3-carboxylic acid methyl ester (480.0 g, 94%) as an off white solid.

Step 3: To a solution of 1-(2,4-dimethoxy-benzyl)-5-oxo-2-phenyl-3-p-tolylsulfanyl-pyrrolidine-3-carboxylic acid methyl ester (50.0 g, 0.101 mol) in DMF (0.5 L) was added sodium hydride (50% in mineral oil, 24.4 g, 0.509 mol) at 0° C. The resulting reaction mixture was stirred at 0° C. for 30 minutes. After 30 minutes, methyl iodide (31.7 ml, 0.509 mol) was added slowly. The resulting reaction mixture was then stirred for 30 min at 0° C. After completion of the reaction (monitored by TLC, mobile phase 30%-ethyl acetate-hexane, Rf 0.3) the reaction was quenched with saturated ammonium chloride solution and extracted with EtOAc (2.0 L). The combined organic layers were dried over sodium sulfate and concentrated under reduced pressure to obtain the crude compound, which was purified by column chromatography (silica gel, 100-200 mesh, 10-20% EtOAc/hexane) to afford 142,4-dimethoxy-benzyl)-4,4-dimethyl-5-oxo-2-phenyl-4,5-dihydro-1H- pyrrole-3-carboxylic acid methyl ester (28.0 g, 70%) as a pale yellow solid.

Step 4: To a solution of 1-(2,4-dimethoxy-benzyl)-4,4-dimethyl-5-oxo-2-phenyl-4,5-dihydro-1H-pyrrole-3-carboxylic acid methyl ester (26.0 g, 0.117 mol) in methanol (300 ml) was added 10% palladium on charcoal (50% moisture, 13.4 g, 0.063 mol) and the resulting mixture was stirred for 16 h at ambient temperature under hydrogen pressure (balloon pressure). After completion of the reaction (monitored by TLC, mobile phase 30%-ethyl acetate-hexane, $R_f$ 0.30) the reaction mixture was filtered through a celite pad. The filtrate was concentrated under reduced pressure to obtain the crude compound which was triturated in diethyl ether to afford 1-(2,4-dimethoxy-benzyl)-4,4-dimethyl-5-oxo-2-phenyl-pyrrolidine-3-carboxylic acid methyl ester (25.0 g, 96%).

Step 5: A stirred suspension of 1-(2,4-dimethoxy-benzyl)-4,4-dimethyl-5-oxo-2-phenyl-pyrrolidine-3-carboxylic acid methyl ester (25.0 g, 0.063 mol) in TFA (250 ml) was heated to 90° C. for 16 h. After completion of the reaction (monitored by TLC, 50% ethyl ether-hexane, Rf-0.3) the reaction was cooled to ambient temperature and was concentrated under reduced pressure. The remains were basified with sat. NaHCO3 solution, followed by the addition of EtOAc (1 L) and stirring of the resulting mixture for 30 minutes. The obtained solid was filtered off and dried under high vacuum to afford 4,4-dimethyl-5-oxo-2-phenyl-pyrrolidine-3-carboxylic acid methyl ester (18.0 g, crude) which was used in the next step.

Step 6: To a suspension of 4,4-dimethyl-5-oxo-2-phenyl-pyrrolidine-3-carboxylic acid methyl ester (43.0 g, 0.174 mmol) in MeOH (400 ml) was added 2 M NaOH (174 ml) at 0° C. The resulting suspension was stirred at 100° C. for 4 h. After consumption of the starting material (monitored by TLC, mobile phase 5% MeOH/DCM, Rf 0.2) the reaction mixture was concentrated and the residue was diluted with water and was washed with ethyl acetate (2×75 ml). The aqueous layer was then acidified to pH 3 with 6N HCl and was extracted with 10% MeOH/DCM (2×75 ml). The combined organic layers were dried over anhydrous $Na_2SO_4$, filtered and concentrated under reduced pressure to afford trans-4,4-dimethyl-5-oxo-2-phenyl-pyrrolidine-3-carboxylic acid (22.0 g, 55.0%) as a brown solid.

Step 7: To a stirred solution of trans-4,4-dimethyl-5-oxo-2-phenyl-pyrrolidine-3-carboxylic acid (22.0 g, 0.095 mol) in benzene-THF (4:1, 125 ml) was added DPPA (25.0 ml, 0.114 mol) followed by IhA (13.35 ml, 0.095 mol) at ambient temperature and the mixture was stirred for 2 h. Benzyl alcohol (14.8 ml, 0.142 mol) was then added and the reaction mixture was heated to 90° C. for 4 h. After completion of the reaction (monitored by TLC) the reaction mixture was diluted with water (10 ml) and extracted with ethyl acetate (3×100 ml). The combined organic layers were washed with 10% citric acid solution (100 ml) followed by saturated $NaHCO_3$ solution (2×100 ml) and were then dried over anhydrous $Na_2SO_4$ and concentrated under reduced pressure. The residue was triturated with diethyl ether (2×80 ml). The obtained solid was filtered off and was dried under high vacuum to afford trans-benzyl 4,4-dimethyl-(5-oxo-2-phenylpyrrolidin-3-yl)carbamate (25.0 g, 78%) as an off white solid.

Step 8: To a stirred solution of benzyl (trans-4,4-dimethyl-5-oxo-2-phenylpyrrolidin-3-yl)carbamate (2.0 g, 5.91 mmol) in 1,4-dioxane (100 mL) in a sealed tube was added 1-(4-Fluoro-phenyl)-5-iodo-1H-indazole (2.4 g, 7.10 mmol) followed by potassium phosphate (2.51 g, 11.83 mmol) and the mixture was degassed using argon for 30 minutes. Then, trans-N,N'-dimethyl cyclohexane-1,2-diamine (0.4 ml, 2.37 mmol) and copper(I)iodide (225 mg, 1.18 mmol) were added and the mixture was heated to 100-110° C. for 16 h. After completion of the reaction (monitored by LCMS, 5% MeOH in DCM), the reaction mixture was filtered through a celite bed and the celite bed was washed with 1,4-dioxane (100 mL), the filtrate was then concentrated under reduced pressure. The reaction was carried out in 10 batches in parallel (2 g each). The combined crude material was purified by column chromatography (silica gel, 100-200 mesh, 2-2.5% MeOH/DCM) to afford benzyl (trans-1-(1-(4-fluorophenyl)-1H-indazol-5-yl)-4,4-dimethyl-5-oxo-2-phenylpyrrolidin-3-yl)carbamate (14.5 g, 45%) as a pale yellow solid.

Step 9: To a stirred solution of benzyl (trans-1-(1-(4-fluorophenyl)-1H-indazol-5-yl)-4,4-dimethyl-5-oxo-2-phenylpyrrolidin-3-yl)carbamate (4.0 g, 7.68 mmol) in THF/MeOH (500 mL, 1:1) was added 10% Pd/C (50% moist, 2.0 g) and the resulting mixture was stirred at ambient temperature under $H_2$ balloon pressure until completion of the reaction (monitored by TLC, 5% MeOH in DCM). The reaction mixture was then filtered through celite and the celite bed was washed with THF. The filtrate was then concentrated under reduced pressure. The reaction was carried out in four batches in parallel (4 g each) and the combined crude material was purified by column chromatography (silica gel, 100-200 mesh, 1.5-2.% MeOH/DCM as eluent) to afford trans-4-amino-1-(1-(4-fluorophenyl)-1H-indazol-5-yl)-3,3-dimethyl-5-phenylpyrrolidin-2-one (7.1 g, 56%) as an off-white solid.

Chiral separation (Chiralpak IC (21.0×250 mm), 5 mobile phase n-hexane/EtOAc/EtOH/isopropylamine 70/15/15/0.1, flow rate 21.0 mL/min) of the racemic compound (7.1 g) in normal phase afforded ((4S,5R)-4-amino-1-(1-(4-fluorophenyl)-1H-indazol-5-yl)-3,3-dimethyl-5-phenylpyrrolidin-2-one, retention time 6.10 minutes) and ((4R,5S)-4-amino-1-(1-(4-fluorophenyl)-1H-indazol-5-yl)-3,3-dimethyl-5-phenylpyrrolidin-2-one, retention time 7.30 minutes).

Step 10: To a solution of (4S,5R)-4-amino-1-(1-(4-fluorophenyl)-1H-indazol-5-yl)-3,3-dimethyl-5-phenylpyrrolidin-2-one (250 mg, 0.603 mmol) in dry THF (4.0 mL) was added lithium aluminium hydride (45.8 mg, 1.206 mmol, 2.0 eq.) at 0° C. under inert atmosphere. The mixture was heated to 60° C. for 2 h. After reaction control (UPLC) showed full consumption of the starting material and formation of the corresponding lactol, aluminium chloride (80.4 mg, 0.603 mmol, 1.0 eq.) was added. The mixture was heated again to 60° C. After stirring for one hour at that temperature the reaction was quenched according to Fieser's Method. To the mixture were added subsequently water (102 µl), 4 M NaOH (102 µl) and finally another amount of water (396 µl) at 0° C. Stirring was continued for 1 h at 0° C. and the mixture was filtered over celite. The solids were thoroughly washed with THF and the organics were combined. Evaporation of the solvent yielded crude (2R,3S)-1-(1-(4-fluorophenyl)-1H-indazol-5-yl)-4,4-dimethyl-2-phenylpyrrolidin-3-amine (282 mg, quant.) which was used directly in the next step without further purification.

EXAMPLE 2

2,2-difluoro-N-(trans-2-phenyl-1-(1-(pyridin-4-yl)-1H-indazol-5-yl)pyrrolidin-3-yl)propanamide

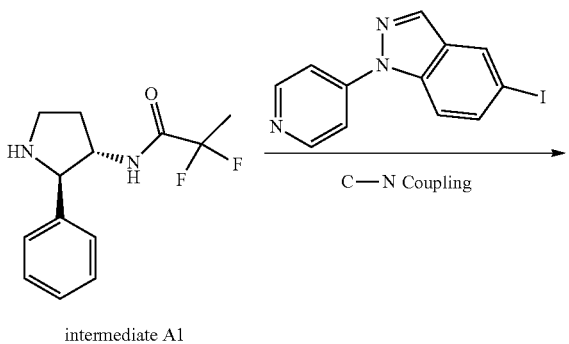

intermediate A1

41

-continued

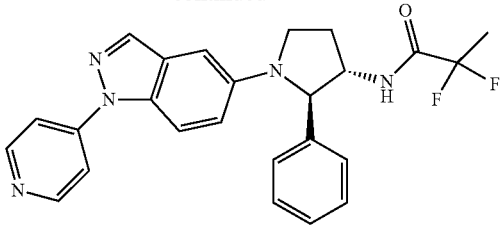

example 2

Step 1: A stirred solution of 2,2-difluoro-N-(trans-2-phenylpyrrolidin-3-yl)propanamide (0.5 g, 1.966 mmol, 1.0 eq.) and 5-iodo-1-(pyridin-4-yl)-1H-indazole (0.631 g, 1.966 mmol, 1.0 eq.) in toluene:THF (2:1, 25 mL) was degassed with argon for 30 min. Then, NaHMDS (1M, 7.86 mL, 7.86 mmol, 4.0 eq.), 2-Dicyclohexylphosphino-2'-(N,N-dimethylamino)biphenyl (Davephos, 0.038 g, 0.0983 mmol, 0.05 eq.) and Pd$_2$(dba)$_3$ (0.18 g, 0.1966 mmol, 0.1 eq.) were added and the reaction was heated to 100° C. for 16 h in a sealed tube. After completion of the reaction (monitored by TLC, TLC system 5% methanol in DCM, Rf-0.4), the reaction was quenched by the addition of water and the mixture was extracted with 10% MeOH in DCM. The combined organic layers were concentrated under reduced pressure to get the crude compound which was purified by column chromatography (230-400 mesh silica gel; 0 to 2% MeOH in DCM) followed by prep. HPLC to afford 2,2-difluoro-N-(trans-2-phenyl-1-(1-(pyridin-4-yl)-1H-indazol-5-yl)pyrrolidin-3-yl)propanamide (0.09 g, 10%).

$^1$H NMR (DMSO-d$_6$) δ=9.18 (d, 1H), 8.67-8.56 (m, 2H), 8.25 (s, 1H), 7.93 (d, 1H), 7.86-7.76 (m, 2H), 7.35 (d, 4H), 7.26 (h, 1H), 6.83 (dd, 1H), 6.73 (d, 1H), 4.75 (d, 1H), 4.13 (s, 1H), 3.85 (dt, 1H), 3.73 (q, 1H), 2.24 (dt, 1H), 2.16 2.02 (m, 1H), 1.76 (t, 3H).

EXAMPLE 3

N-((2S,3R)-2-cyclopropyl-1-(1-(4-fluorophenyl)-1H-indazol-5-yl)pyrrolidin-3-yl)-2,2-difluoropropanamide and example 8: N-((2R,3S)-2-cyclopropyl-1-(1-(4-fluorophenyl)-1H-indazol-5-yl)pyrrolidin-3-yl)-2,2-difluoropropanamide

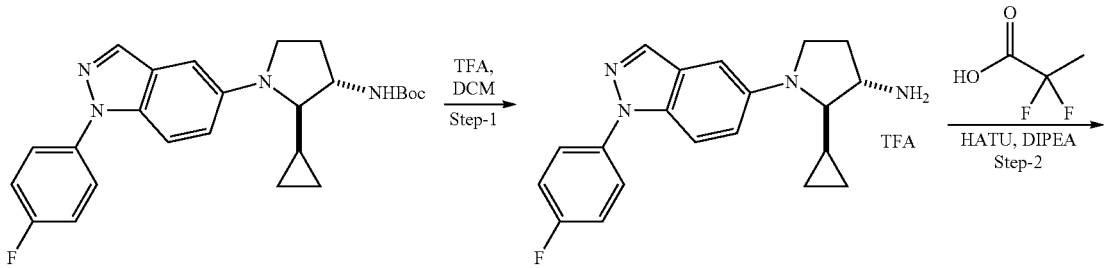

intermediate A2

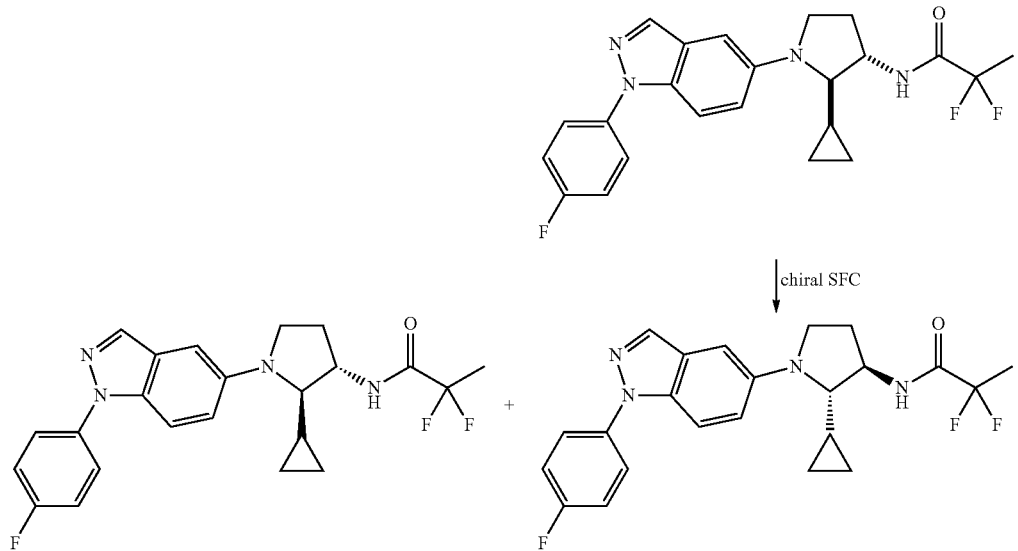

example 8 + example 3

Step 1: To stirred solution of intermediate A2 (11.0 g, 25.22 mmol, 1.0 eq.) in DCM (500 mL) was added TFA (130 mL) at 0° C. The reaction mixture was then stirred at ambient temperature for 1 h. The solvent was then evaporated under reduced pressure to afford trans-2-cyclopropyl-1-(1-(4-fluorophenyl)-1H-indazol-5-yl)pyrrolidin-3-amine TFA salt (15 g, crude, brown viscous oil). TLC system: 5% MeOH-DCM; Rf: 0.28.

Step 2: To stirred solution of trans-2-cyclopropyl-1-(1-(4-fluorophenyl)-1H-indazol-5-yl)pyrrolidin-3-amine TFA salt (15 g, 34.64 mmol, 1.0 eq.) in DMF (500 mL), were added HATU (15.79 g, 41.57 mmol, 1.2 eq.) and DIPEA (18 mL, 103.92 mmol, 3 eq.) at 0° C. and the mixture was stirred for 10 min at 0° C. before the addition of 2,2-difluoropropanoic acid (4.57 g, 41.57 mmol, 1.2 eq.) at 0° C. The reaction mixture was then stirred at ambient temperature for 18 h. The reaction mixture was then diluted with EtOAc (2 L), washed with water (5×800 mL) and brine (800 mL), dried over $Na_2SO_4$, filtered and concentrated under reduced pressure. The obtained residue was purified by flash column chromatography, eluent 2% MeOH-DCM. The obtained material was then purified by reverse phase column chromatography to afford N-(trans-2-cyclopropyl-1-(1-(4-fluorophenyl)-1H-indazol-5-yl)pyrrolidin-3-yl)-2,2-difluoropropanamide (3.2 g, 30% over two steps, off-white solid). TLC system: 40% EtOAc-Pet ether; Rf: 0.28. N-(trans-2-cyclopropyl-1-(1-(4-fluorophenyl)-1H-indazol-5-yl)pyrrolidin-3-yl)-2,2-difluoropropanamide (3.2 g) was then separated into the individual enantiomers by chiral Prep-SFC (column: Chiralpak AD-H (250×30) mm, solvent: 65% $CO_2$, 35% methanol, total flow: 100.0 g/min, back pressure 100 bar) to obtain the corresponding individual enantiomers example 8 (1.18 g; pale yellow solid, rt: 2.67 min) and example 3 (1.29 g; light green solid rt: 3.79 min)

Example 3: $^1$H NMR (DMSO-$d_6$) δ=8.83 (d, 1H), 8.15 (d, 1H), 7.76 (ddt, 2H), 7.67 (d, 1H), 7.45-7.35 (m, 2H), 7.05 (dd, 1H), 6.88 (d, 1H), 4.21 (t, 1H), 3.62 (d, 1H), 3.50 (td, 1H), 3.45-3.39 (m, 1H), 2.37 (dtd, 1H), 2.02 (ddt, 1H), 1.71 (td, 3H), 1.01 0.91 (m, 1H), 0.52 0.44 (m, 2H), 0.33 (dddd, 2H).

Example 8: $^1$H NMR (DMSO-$d_6$) δ=8.83 (d, 1H), 8.15 (d, 1H), 7.81-7.72 (m, 2H), 7.67 (d, 1H), 7.40 (dd, 2H), 7.06 (dd, 1H), 6.89 (d, 1H), 4.22 (t, 1H), 3.63 (d, 1H), 3.50 (td, 1H), 3.45-3.39 (m, 1H), 2.38 (dtd, 1H), 2.03 (ddt, 1H), 1.72 (t, 3H), 1.01-0.92 (m, 1H), 0.54-0.45 (m, 2H), 0.44-0.37 (m, 1H), 0.26 (dtd, 1H).

EXAMPLE 7

6-(2,3-dihydrobenzo[b][1,4]dioxin-6-yl)-7-(1-(4-fluorophenyl)-1H-indazol-5-yl)-1,7-diazaspiro[4.4]nonan-2-one

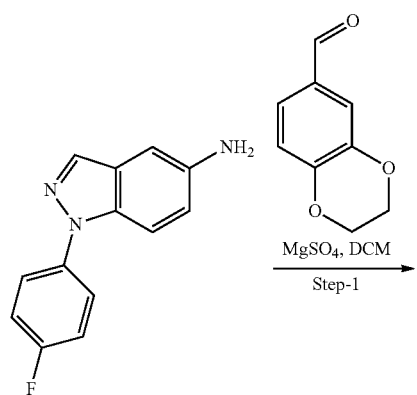

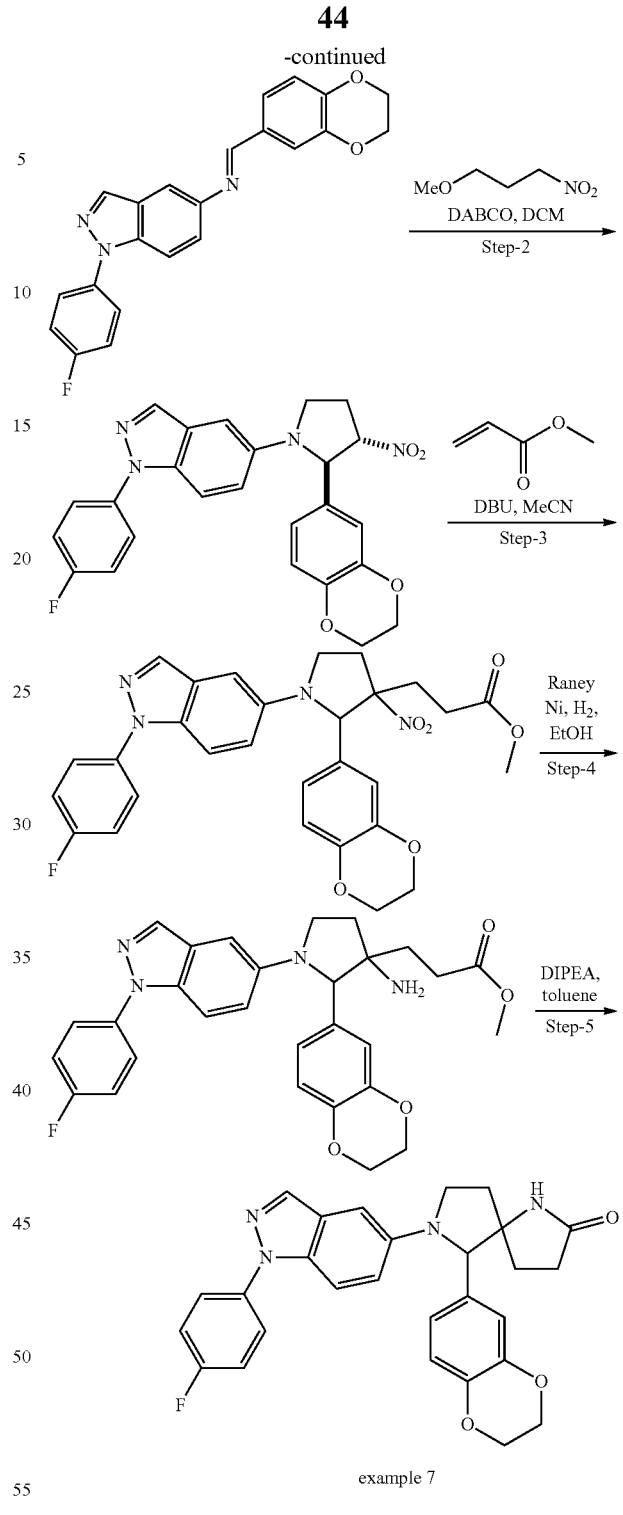

example 7

Step 1: To a stirred solution of 1-(4-fluorophenyl)-1H-indazol-5-amine (1.5 g, 1.0 eq.) and 2,3-dihydrobenzo[b][1,4]dioxine-6-carbaldehyde (1.08 g, 1.0 eq.) in dichloromethane (35 mL) was added anhydrous $MgSO_4$ (6.3 g, 8.0 eq.). The resulting solution was then stirred at ambiente temperature for 48 h. After completion of the reaction, the reaction mixture was filtered through a small pad of celite and was then concentrated under reduced pressure to afford 1-(2,3-dihydrobenzo[b][1,4]dioxin-6-yl)-N-(1-(4-fluoropheny 1)-1H-indazol-5-y fimethanimine (2.4 g, 99%). This material was used without further purification in the next step.

Step 2: To a stirred solution of 1-(2,3-dihydrobenzo[b][1,4]dioxin-6-yl)-N-(1-(4-fluorophenyl)-1H-indazol-5-yl)methanimine (500 mg, 1.0 eq.) in DCM (10 mL) was added 3-nitropropyl methanesulfonate (470 mg, 1.0 eq.), followed by the addition of DABCO (50 mg, 0.33 eq.) and scandium (III)triflate (50 mg, 0.08 eq.) and stirring was continued for 72 hours. The completion of the reaction was monitored by TLC. The reaction mixture was quenched with water and extracted with DCM (20 mL×3). The combined organic layers were washed with brine, dried over anhydrous sodium sulfate, filtered and evaporated under reduced pressure to obtain the crude compound. The crude compound was then purified by column chromatography (40% ethyl acetate-hexane) to afford 1-(4-fluorophenyl)-5-(trans-3-nitro-2-phenylpyrrolidin-1-yl)-1H-indazole (160 mg, 26%) as a pale yellow solid.

Step 3: To a stirred solution of 1-(4-fluorophenyl)-5-(trans-3-nitro-2-phenylpyrrolidin-1-yl)-1H-indazole (430 mg, 1.0 eq.) in MeCN (7 mL) were added DBU (100 mg, 1.0 eq.) and methyl acrylate (60 mg, 1.0 eq.) under an inert atmosphere and the resulting mixture was stirred for 24 hours. After completion of the reaction, the reaction mixture was quenched with ice-water and extracted with ethyl acetate (20 mL×3). The combined organic layers were washed with brine, dried over anhydrous sodium sulfate, filtered and evaporated under reduced pressure to obtain a residue. This was then purified by column chromatography (70% ethyl acetate-hexane) to obtain methyl 3-(2-(2,3-dihydrobenzo[b][1,4]dioxin-6-yl)-1-(1-(4-fluorophenyl)-1H-indazol-5-yl)-3-nitropyrrolidin-3-yl)propanoate (380 mg, 75% yield) as a pale yellow liquid.

Step 4: To a stirred and deoxygenated solution of methyl 3-(2-(2,3-dihydrobenzo[b][1,4]dioxin-6-yl)-1-(1-(4-fluorophenyl)-1H-indazol-5-yl)-3-nitropyrrolidin-3-yl)propanoate (380 mg, 1.0 eq.) in ethanol (20 mL) was added Raney-Ni (190 mg, 50% by wt) and the mixture was stirred under a $H_2$ balloon for 12 hours. After completion of the reaction (monitored by TLC), the reaction mixture was filtered through a celite bed and the filtrate was evaporated under reduced pressure and was used as such for the next step.

Step 5: To a stirred solution of methyl 3-(3-amino-2-(2,3-dihydrobenzo[b][1,4]dioxin-6-yl)-1-(1-(4-fluorophenyl)-1H-indazol-5-yl)pyrrolidin-3-yl)propanoate (300 mg, 1.0 eq.) in toluene (20 mL) was added DIPEA (200 μL, 2.0 eq.) and the mixture was heated to reflux for 24 hours. After completion of the reaction (monitored by LCMS), the reaction mixture was evaporated under reduced pressure and purified by preparative HPLC to obtain 50 mg (18%) of 6-(2,3-dihydrobenzo[b][1,4]dioxin-6-yl)-7-(1-(4-fluorophenyl)-1H-indazol-5-yl)-1,7-diazaspiro[4.4]nonan-2-one.

$^1$H NMR (DMSO-d$_6$) δ=8.09 (s, 1H), 7.74-7.72 (m, 2H), 7.60 (d, 1H), 7.38-7.34 (m, 3H), 6.81-6.78 (m, 2H), 6.67-6.66 (m, 3H), 4.48 (s, 1H), 4.19 (m, 4H), 3.82-3.78 (m, 1H), 3.45-3.38 (m, 1H), 2.44-1.90 (m, 6H).

m/z: found for [m+H]$^+$=485.20, calc. for $C_{28}H_{25}FN_4O_3$: 484.19

EXAMPLE 10

N-(trans-1-((1H-indazol-4-yl)methyl)-2-(2,3-dihydrobenzo[b][1,4]dioxin-6-yl)pyrrolidin-3-yl)cyclopropanesulfonamide

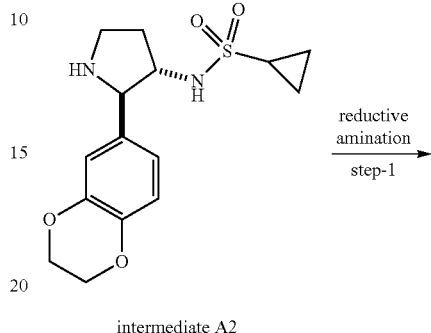

intermediate A2 reductive amination
step-1

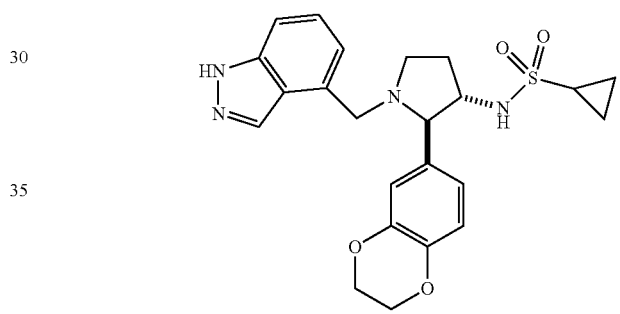

example 10

Step 1: N-(trans-2-(2,3-dihydrobenzo[b][1,4]dioxin-6-yl)pyrrolidin-3-yl)cyclopropanesulfonamide (80.0 mg, 0.247 mmol, 1.0 eq.), 1H-indazole-4-carbaldehyde (90.1 mg, 0.617 mmol, 2.5 eq.) and sodium triacetoxyborohydride (156.8 mg, 0.740 mmol, 3.0 eq.) were weighed out into a microwave vial. A stir bar was added, the vial was sealed and purged with nitrogen. Then, DCM (2.4 mL) and glacial acetic acid (0.014 mL) were added and the mixture was heated to 60° C. for one hour. Then, DCM and sat. NaHCO$_3$ solution were added, and the mixture was filtered through a hydrophobic frit. The organic layer was evaporated, and the obtained residue was purified via LC and HPLC to yield 48.0 mg (43%) of N-(trans-1-((1H-indazol-4-yl)methyl)-2-(2,3-dihydrobenzo[b][1,4]dioxin-6-yl)pyrrolidin-3-yl)cyclopropanesulfonamide.

m/z: found for [m+H]$^+$=455.16, calc. for $C_{23}H_{26}N_4O_4S$: 454.17.15

EXAMPLE 23

N-(trans-2-cyclopropyl-1-(1-(4-fluorophenyl)-1H-indazol-5-yl)pyrrolidin-3-yl)thiazol-2-amine

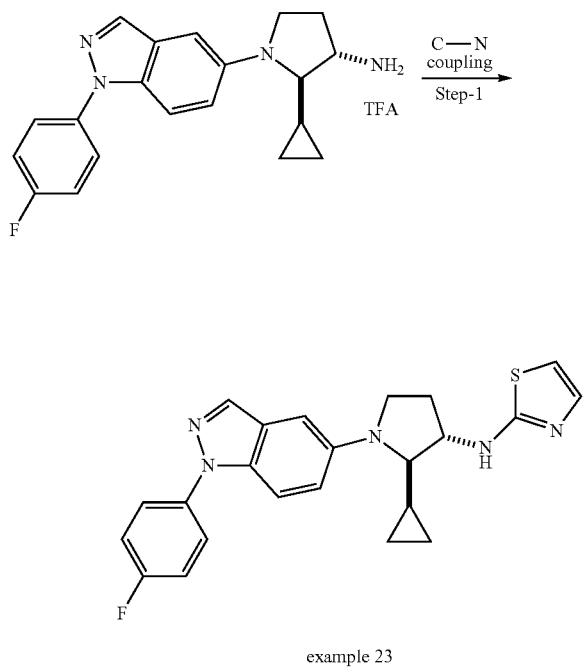

example 23

Step 1: To a solution of trans-2-cyclopropyl-1-(1-(4-fluorophenyl)-1H-indazol-5-yppyrrolidin-3-amine TFA salt (0.2 g, 0.595 mmol, 1.0 eq., see example 3) in toluene (3 mL) were added 2-bromothiazole (0.195 g, 1.190 mmol, 2.0 eq.) and caesium carbonate (0.386 g, 1.190 mmol, 2.0 eq.). The reaction mixture was then deoxygenated using argon for 10 minutes. Then, (RuPhos)palladium(II) phenethylamine chloride (RuPhos Palladacycle, 0.0242 g, 0.0297 mmol, 0.05 eq.) and 2-dicyclohexylphosphino-2',6'-diisopropoxybiphenyl (RuPhos, 0.0138 g, 0.0297 mmol, 0.05 eq.) were added and the reaction mixture was heated to 120° C. for 16 h. The reaction mixture was then diluted with toluene (10 mL) and filtered through a celite bed. The filtrate was washed with water (2×10 mL), the aqueous part was then extracted with ethyl acetate (2×10 mL). The combined organic layers were washed with brine, dried over Na$_2$SO$_4$ and concentrated under reduced pressure to get the crude material. The crude material purified using preparative HPLC to afford N-(trans-2-cyclopropyl-1-(1-(4-fluorophenyl)-1H-indazol-5-yl)pyrrolidin-3-yl)thiazol-2-amine amine (0.02 g, 8%) as a yellow solid.

$^1$H NMR (DMSO-d$_6$) δ=8.13 (s, 1H), 7.76-7.773 (m, 3H), 7.66 (d, 1H), 7.39 (t, 2H), 7.06-7.01 (m, 2H), 6.85 (s, 1H), 6.61 (d, 1H), 4.16-4.13 (m, 1H), 3.53-3.51 (m, 1H), 3.72-3.70 (m, 1H), 3.40-3.33 (m, 1H), 2.07-2.01 (m, 1H), 1.01-0.98 (m, 2H), 0.50-0.32 (m, 4H)

EXAMPLE 24

N-(trans-2-cyclopropyl-1-(1-(4-fluorophenyl)-1H-indazol-5-yl)pyrrolidin-3-yl)pyrimidin-2-amine

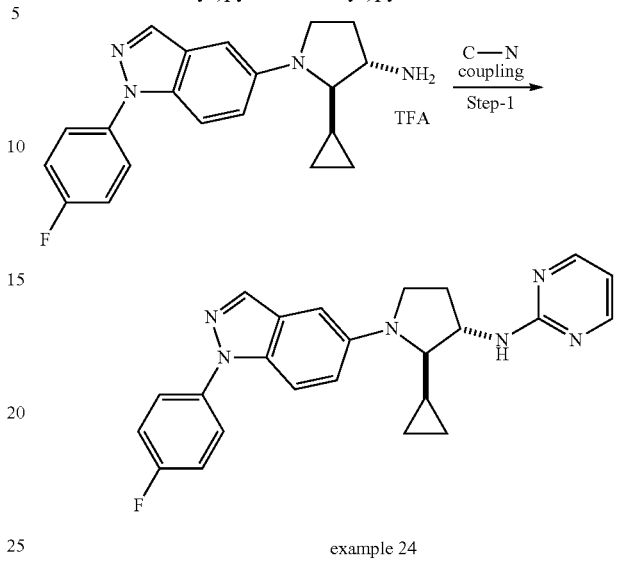

example 24

Step 1: To a solution of trans-2-cyclopropyl-1-(1-(4-fluorophenyl)-1H-indazol-5-yfipyrrolidin-3-amine TFA salt (0.1 g, 0.29 mmol, 1.0 eq., see example 3) in isopropanol (1.5 mL) ware added DIPEA (0.077 mL, 0.435 mmol, 1.5 eq.) and 2-chloropyrimidine (0.035 g, 0.276 mmol, 0.95 eq). The reaction mixture was then heated to 100° C. for 12 h. The reaction mixture was then diluted with water (10 mL) and the mixture was extracted with ethyl acetate (2×20 ml). The combined organic layers were washed with brine (20 mL), dried over Na$_2$SO$_4$ and concentrated under reduced pressure to get the crude material. The crude material was purified by column chromatography (230-400 mesh silica gel; 50% ethyl acetate/hexane; Rf-value-0.5) to afford N-(trans-2-cyclopropyl-1-(1-(4-fluorophenyl)-1H-indazol-5-yl)pyrrolidin-3-yl)pyrimidin-2-amine (0.03 g, 25%) as an off-white solid.

$^1$H NMR (DMSO-d$_6$) δ=8.30 (m, 2H), 8.12 (s, 1H), 7.76-7.73 (m, 2H), 7.64 (d, 1H), 7.41-7.36 (m, 3H), 7.00 (d, 1H), 6.83 (s, 1H), 5.89 (t, 1H), 4.27 (s, 1H), 3.68-3.67 (m, 1H), 3.47 (s, 1H), 2.50-2.42 (m, 1H), 2.08-2.05 (m, 1H), 1.24 (s, 1H), 1.04-1.02 (m, 1H), 0.48-0.36 (m, 4H)

EXAMPLE 27

2,2-difluoro-N-(5-(1-(4-fluorophenyl)-1H-indazol-5-yl)-5-azaspiro[3.4]octan-8-yl)propanamide

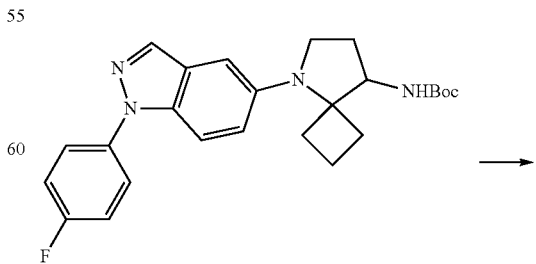

intermediate A4

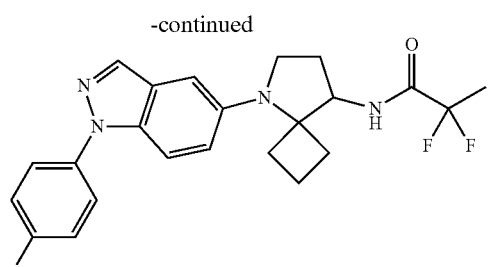

example 27

Example 27 was prepared in analogy to the synthesis of example 3, using intermediate 4 instead of intermediate 2 in the first step.

$^1$H NMR (DMSO-$d_6$) δ=8.76 (d, 1H), 8.22 (d, 1H), 7.82-7.77 (m, 2H), 7.75 (dt, 1H), 7.51-7.33 (m, 2H), 7.25 (dd, 1H), 7.23-7.20 (m, 1H), 4.52 (d, 1H), 3.48-3.38 (m, 1H), 3.31 (d, 1H), 2.70 (dt, 1H), 2.67 2.58 (m, 1H), 2.12 (s, 1H), 2.06 (s, 1H), 2.01 (d, 1H), 1.92 (ddt, 1H), 1.83 (t, 3H), 1.81-1.74 (m, 1H), 1.60 (dp, 1H).

EXAMPLE 28

N-((2R,3 S)-1-(1-(4-fluorophenyl)-1H-indazol-5-yl)-4,4-dimethyl-2-phenylpyrrolidin-3-yl)cyclopropanecarboxamide

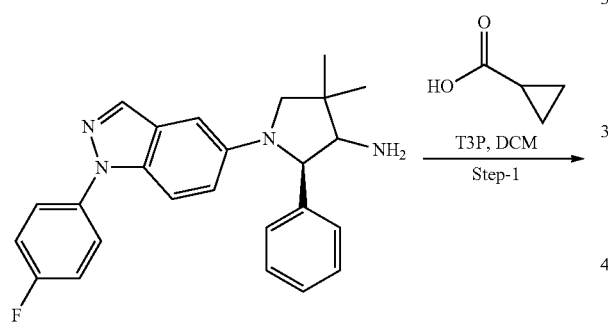

intermediate A5

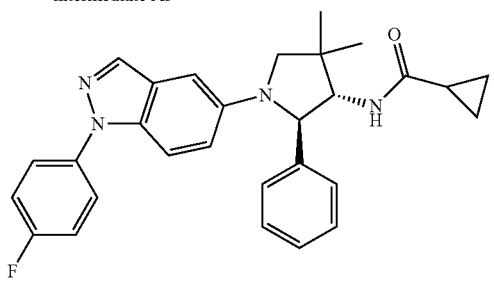

example 28

Step 1: To a solution of cyclopropanecarboxylic acid (38.7 mg, 0.449 mmol, 2.0 eq.) and triethyl amine (125 µl, 0.899 mmol, 4.0 eq) in dichloromethane (2.2 mL) propylphosphonic anhydride solution (>50 wt. % in ethyl acetate, 334 µl, 0.562 mmol, 2.5 eq.) was added dropwise at room temperature. After stirring for 15 min at room temperature, (2R,3 S)-1-(1-(4-fluorophenyl)-1H-indazol-5-yl)-4,4-dimethyl-2-phenyl)pyrrolidin-3-amine (90 mg, 0.225 mmol, 1.0 eq.) was added. After stirring overnight at room temperature, additional amounts of triethyl amine (63 µl, 0.339 mmol, 2.0 eq), propylphosphonic anhydride solution (>50 wt. % in ethyl acetate, 134 µl, 0.225 mmol, 1.0 eq.) and cyclopropanecarboxylic acid (19.3 mg, 0.225 mmol, 1.0 eq.) were added. Stirring was continued until reaction control (UPLC) showed full consumption of the starting material and the reaction was quenched using saturated $Na_2CO_3$-solution. After stirring for 30 mins at room temperature, the layers were separated and the aqueous layer was extracted with DCM three times. The combined organics were washed with water and filtered over a silica cartridge (1 g). The obtained crude product was purified by flash chromatography (12 g Silica, cyclohexane/ethyl acetate gradient as eluent) to obtain example N-((2R,3S)-1-(1-(4-fluorophenyl)-1H-indazol-5-yl)-4,4-dimethyl-2-phenylpyrrolidin-3-yl)cyclopropanecarboxamide (30 mg, 0.064 mmol, 28%) as a colorless solid.

$^1$H NMR (DMSO-$d_6$) δ=8.36-8.29 (m, 1H), 8.05 (d, 1H), 7.75-7.68 (m, 2H), 7.58 (dd, 1H), 7.39-7.32 (m, 4H), 7.29 (t, 2H), 7.22-7.17 (m, 1H), 6.80 (dd, 1H), 6.62 (d, 1H), 4.52 (d, 1H), 4.15 (dd, 1H), 3.75 (d, 1H), 1.69 (tt, 1H), 1.04 (s, 3H), 0.98 (s, 3H), 0.72 0.59 (m, 3H), 0.59 0.52 (m, 1H).

EXAMPLE 29

N-((2R,3 S)-1-(1-(4-fluorophenyl)-1H-indazol-5-yl)-4,4-dimethyl-2-phenylpyrrolidin-3-yl)methanesulfonamide

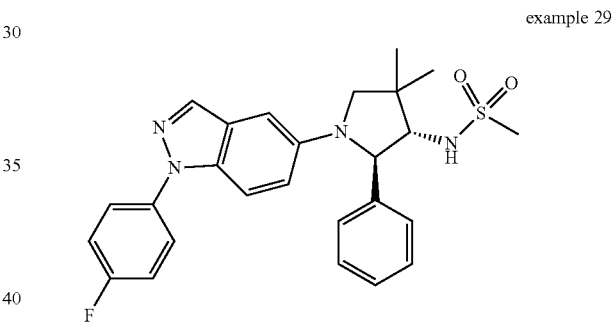

example 29

To a solution of (2R,3S)-1-(1-(4-fluorophenyl)-1H-indazol-5-yl)-4,4-dimethyl-2-phenylpyrrolidin-3-amine (90 mg, 0.225 mmol, 1.0 eq.) in dichloromethane (2.2 mL) was added triethyl amine (94 µl, 0.674 mmol, 3.0 eq.) at room temperature. The mixture was cooled down to 0° C. before methanesulfonyl chloride (26 µl, 0.337 mmol, 1.5 eq.) was added. The reaction was allowed to room temperature overnight. Then, another aliquot of triethyl amine (63 µl, 0.449 mmol, 2.0 eq) and methanesulfonyl chloride (17 µl, 0.25 mmol, 1.0 eq.) were added. Stirring was continued at room temperature until reaction control (UPLC) showed full consumption of the starting material. The reaction was then quenched using sat. $NaHCO_3$-solution and dichloromethane. The layers were separated by the means of a hydrophobic frit and the organic layer was adsorbed on diatomaceous earth. Flash chromatography (12 g silica, cyclohexane/ethyl acetate gradient as eluent) gave N-((2R,3S)-1-(1-(4-fluorophenyl)-1H-indazol-5-yl)-4,4-dimethyl-2-phenylpyrrolidin-3-yl)methanesulfonamide (30 mg, 0.0627 mmol, 28%) as a white solid.

$^1$H NMR (DMSO-$d_6$) δ=8.04 (d, 1H), 7.84 (d, 1H), 7.74-7.66 (m, 2H), 7.56 (d, 1H), 7.53 7.49 (m, 2H), 7.39-7.33 (m, 4H), 7.29-7.23 (m, 1H), 6.81 (ddd, 1H), 6.64 (d, 1H), 4.50 (d, 1H), 3.79 (d, 1H), 3.50 (t, 1H), 3.42 (d, 1H), 2.07 (s, 3H), 1.12 (s, 3H), 0.95 (s, 3H).

EXAMPLE 30

2,2-difluoro-N-((2R3S)-1-(1-(4-fluorophenyl)-1H-indazol-5-yl)-4,4-dimethyl-2-phenylpyrrolidin-3-yl)propanamide

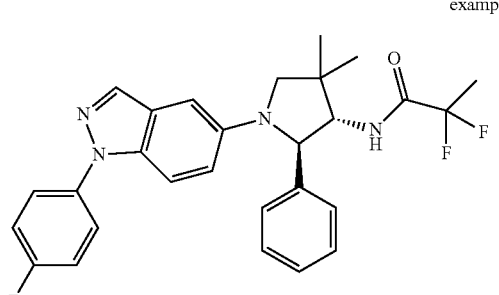

example 30

Example 30 was prepared in analogy to the synthesis described for example 28 using 2,2-difluoropropanoic acid instead of cyclopropanecarboxylic acid.

$^1$H NMR (DMSO-$d_6$) δ=8.89 (d, 1H), 8.06 (s, 1H), 7.76-7.67 (m, 2H), 7.59 (d, 1H), 7.37 (d, 2H), 7.34 (d, 1H), 7.33 (s, 1H), 7.30 (t, 2H), 7.21 (t, 1H), 6.80 (dd, 1H), 6.62 (d, 1H), 4.82 (d, 1H), 4.13 (t, 1H), 3.80 (d, 1H), 3.50 (d, 1H), 1.74 (t, 3H), 1.08 (s, 3H), 0.98 (s, 3H).

The examples in the table below have been synthesized in analogy to the described syntheses above, using variations obvious to the person skilled in the art.

| Example Nr. | Structure | Data |
|---|---|---|
| 1 | 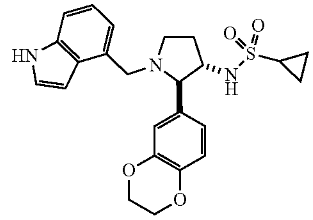 [SMILES: O=S(=O)(N[C@H]1CCN(Cc2cccc3[nH]ccc23)[C@@H]1c1ccc2c(c1)OCCO2)C1CC1] | $^1$H NMR (DMSO-$d_6$) δ = 11.01 (t, 1H), 7.43 (d, 1H), 7.28 (dd, 2H), 7.07 – 6.96 (m, 3H), 6.90 (dd, 2H), 6.41 (ddd, 1H), 4.24 (tt, 4H), 3.89 (d, 1H), 3.56 (qd, 1H), 3.26 (d, 1H), 3.16 (d, 1H), 2.87 (td, 1H), 2.35 (q, 1H), 2.18 (dd, 1H), 2.11 (tt, 1H), 1.69 (dddd, 1H), 0.76 (dtdd, 4H). |
| 4 | 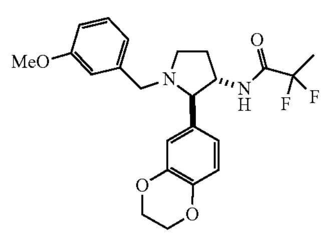 [SMILES: COc1cccc(CN2CC[C@H](NC(=O)C(C)(F)F)[C@H]2c2ccc3c(c2)OCCO3)c1] | $^1$H NMR (DMSO-$d_6$) δ = 8.84 (d, 1H), 7.23 (t, 1H), 6.91 (d, 1H), 6.88 – 6.76 (m, 5H), 4.22 (s, 4H), 4.02 – 3.95 (m, 1H), 3.74 (s, 3H), 3.68 – 3.60 (m, 1H), 3.45 – 3.36 (m, 1H), 3.11 (dd, 1H), 2.98 – 2.93 (m, 1H), 2.40 (dd, 1H), 2.21 – 2.11 (m, 1H), 1.66 (t, 4H). |
| 5 | 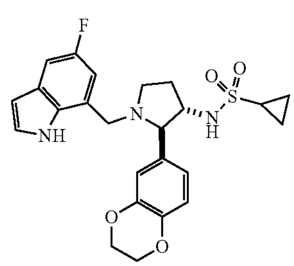 [SMILES: O=S(=O)(N[C@H]1CCN(Cc2cc(F)cc3cc[nH]c23)[C@@H]1c1ccc2c(c1)OCCO2)C1CC1] | $^1$H NMR (DMSO-$d_6$) δ = 10.86 (s, 1H), 7.36 (s, 1H), 7.15 (s, 1H), 7.09 – 7.05 (m, 1H), 6.98 (s, 1H), 6.83 (d, 2H), 6.42 (s, 1H), 4.22 (s, 4H), 3.85 (s, 1H), 3.71 (s, 1H), 3.46 (s, 1H), 3.23 (s, 1H), 3.03 (s, 1H), 2.33 (s, 2H), 2.14 – 2.08 (m, 1H), 1.74 (s, 1H), 0.77 (q, 4H). |
| 6 | 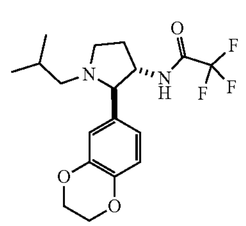 [SMILES: CC(C)CN1CC[C@H](NC(=O)C(F)(F)F)[C@H]1c1ccc2c(c1)OCCO2] | m/z: found for [m + H]$^+$ = 373.18, calc. for $C_{18}H_{23}F_3N_2O_3$: 372.17 |

-continued

| Example Nr. | Structure | Data |
|---|---|---|
| 9 | 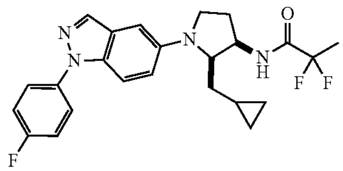 [SMILES: CC(F)(F)C(=O)N[C@@H]1CCN(c2ccc3c(cnn3-c3ccc(F)cc3)c2)[C@@H]1CC1CC1] | $^1$H NMR (DMSO-d$_6$) δ = 8.96 (d, 1H), 8.14 (d, 1H), 7.81 – 7.72 (m, 2H), 7.70 (d, 1H), 7.44 – 7.34 (m, 2H), 7.02 (dd, 1H), 6.82 (d, 1H), 4.35 (dq, 1H), 4.11 (td, 1H), 3.46 (td, 1H), 3.20 (td, 1H), 2.36 (tt, 1H), 2.18 (dtd, 1H), 1.85 – 1.68 (m, 3H), 1.57 – 1.43 (m, 1H), 1.18 (ddd, 1H), 0.65 (ddt, 1H), 0.50 -0.33 (m, 2H), 0.12 – 0.04 (m, 1H), 0.03 – −0.04 (m, 1H). |
| 11 | 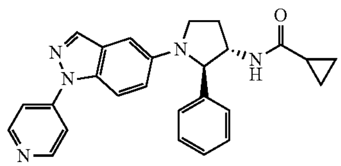 [SMILES: O=C(N[C@H]1CCN(c2ccc3c(cnn3-c3ccncc3)c2)[C@@H]1c1ccccc1)C1CC1] | m/z: found for [m + H]$^+$ = 424.2, calc. for C$_{26}$H$_{25}$N$_5$O: 423.21 |
| 12 | 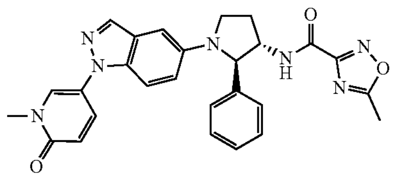 [SMILES: Cc1nc(C(=O)N[C@H]2CCN(c3ccc4c(cnn4-c4ccc(=O)n(C)c4)c3)[C@@H]2c2ccccc2)no1] | $^1$H NMR (DMSO-d$_6$) δ = 9.45 (d, 1H), 8.10 (d, 1H), 8.03 (d, 1H), 7.72 (dd, 1H), 7.48 (d, 1H), 7.41 – 7.31 (m, 4H), 7.29 – 7.23 (m, 1H), 6.77 (dd, 1H), 6.68 (d, 1H), 6.53 (d, 1H), 4.85 (d, 1H), 4.30 (tt, 1H), 3.86 (td, 1H), 3.74 (td, 1H), 3.50 (s, 3H), 2.65 (d, 3H), 2.33 -2.23 (m, 1H), 2.18 (ddt, 1H). |
| 13 | 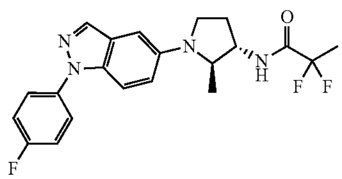 [SMILES: C[C@@H]1[C@@H](NC(=O)C(C)(F)F)CCN1c1ccc2c(cnn2-c2ccc(F)cc2)c1] | m/z: found for [m + H]$^+$ = 403.18, calc. for C$_{21}$H$_{21}$F$_3$N$_4$O: 402.17 |
| 14 | 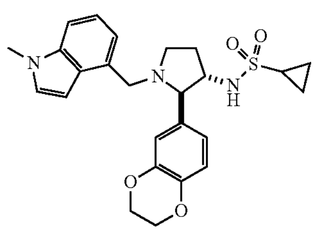 [SMILES: Cn1ccc2c(CN3CC[C@H](NS(=O)(=O)C4CC4)[C@H]3c3ccc4c(c3)OCCO4)cccc21] | m/z: found for [m + H]$^+$ = 468.21, calc. for C$_{25}$H$_{29}$N$_3$O$_4$S: 467.19 |
| 15 | 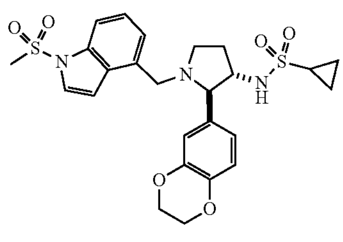 [SMILES: CS(=O)(=O)n1ccc2c(CN3CC[C@H](NS(=O)(=O)C4CC4)[C@H]3c3ccc4c(c3)OCCO4)cccc21] | m/z: found for [m + H]$^+$ = 532.2, calc. for C$_{25}$H$_{29}$N$_3$O$_6$S$_2$: 531.15 |
| 16 | 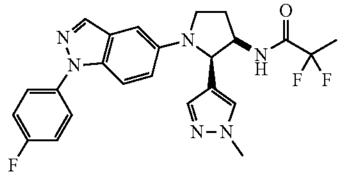 [SMILES: Cn1cc([C@@H]2[C@H](NC(=O)C(C)(F)F)CCN2c2ccc3c(cnn3-c3ccc(F)cc3)c2)cn1] | $^1$H NMR (DMSO-d$_6$) δ =8.48 (d, 1H), 8.10 (d, 1H), 7.79 – 7.69 (m, 2H), 7.66 – 7.58 (m, 1H), 7.43 – 7.30 (m, 3H), 7.15 (d, 1H), 6.89 (dd, 1H), 6.75 (d, 1H), 5.01 (d, 1H), 4.36 (dd, 1H), 3.75 (s, 3H), 3.70 – 3.61 (m, 1H), 3.41 – 3.29 (m, 1H), 2.37 – 2.25 (m, 1H), 2.25 – 2.14 (m, 1H), 1.68 (t, 3H). |
| 17 | 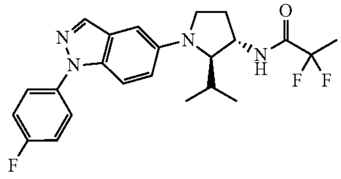 [SMILES: CC(C)[C@@H]1[C@@H](NC(=O)C(C)(F)F)CCN1c1ccc2c(cnn2-c2ccc(F)cc2)c1] | $^1$H NMR (DMSO-d$_6$) δ = 8.91 (d, 1H), 8.18 – 8.10 (m, 1H), 7.82 – 7.72 (m, 2H), 7.73 – 7.64 (m, 1H), 7.45 – 7.35 (m, 2H), 7.00 (dd, 1H), 6.84 (dd, 1H), 4.35(tt, 1H), 3.70 (dd, 1H), 3.56 (td, 1H), 3.45 (t, 1H), 2.30 – 2.20 (m, 1H), 2.20 – 2.10 (m, 1H), 2.03 – 1.89 (m, 1H), 1.76 (dt, 3H), 0.98 (d, 3H), 0.83 (dd, 3H). |

| Example Nr. | Structure | Data |
|---|---|---|
| 18 | 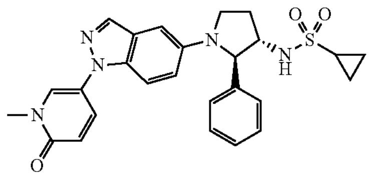 [SMILES: Cn1cc(-n2ncc3cc(N4CC[C@H](NS(=O)(=O)C5CC5)[C@H]4c4ccccc4)ccc32)ccc1=O] | m/z: found for [m + H]⁺ = 490.19, calc. for $C_{26}H_{27}N_5O_3S_2$: 489.18 |
| 19 | 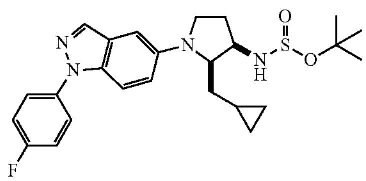 [SMILES: CC(C)(C)OS(=O)N[C@@H]1CCN(c2ccc3c(cnn3-c3ccc(F)cc3)c2)[C@@H]1CC1CC1] | ¹H NMR (DMSO-d₆) δ = 8.13 (d, 1H), 7.77 (dd, 2H), 7.69 (d, 1H), 7.39 (t, 2H), 7.28 (d, 1H), 6.99 (d, 1H), 6.77 (s, 1H), 4.08 (dq, 1H), 4.01 (d, 1H), 3.37 (dd, 1H), 3.15 (q, 1H), 2.10 (dt, 2H), 1.56 – 1.50 (m, 1H), 1.41 (s, 9H), 1.12 (dd, 1H), 0.73 (p, 1H), 0.40 (d, 2H), 0.09 (t, 1H), 0.02 (dd, 1H). |
| 20 | 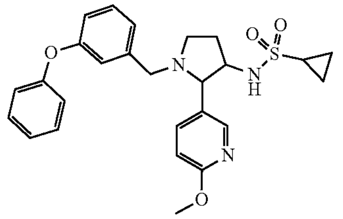 [SMILES: COc1ccc(C2C(NS(=O)(=O)C3CC3)CCN2Cc2cccc(Oc3ccccc3)c2)cn1] | m/z: found for [m + H]⁺ = 480.1, calc. for $C_{26}H_{29}N_3O_4S$: 479.19 |
| 21 | 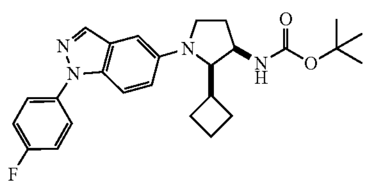 [SMILES: CC(C)(C)OC(=O)N[C@@H]1CCN(c2ccc3c(cnn3-c3ccc(F)cc3)c2)[C@@H]1C1CCC1] | ¹H NMR (DMSO-d6) δ= 8.13 (d, 1H), 7.80 – 7.73 (m, 2H), 7.66 (d, 1H), 7.43 – 7.36 (m, 2H), 7.05 – 6.99 (m, 2H), 6.83 (d, 1H), 3.79 (d, 1H), 3.75 (d, 1H), 3.51 – 3.45 (m, 1H), 3.39 – 3.31 (m, 1H), 2.16 (dtd, 1H), 2.01 – 1.95 (m, 1H), 1.92 – 1.80 (m, 4H), 1.79 – 1.63 (m, 2H), 1.41 (d, 1H), 1.36 (s, 9H). |
| 22 | 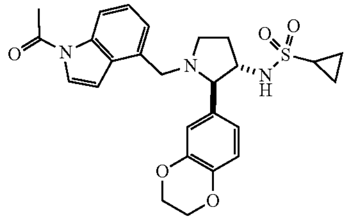 [SMILES: CC(=O)n1ccc2c(CN3CC[C@H](NS(=O)(=O)C4CC4)[C@H]3c3ccc4c(c3)OCCO4)cccc21] | m/z: found for [m + H]⁺ = 496.1, calc. for $C_{26}H_{29}N_3O_5S$: 495.18 |
| 25 | 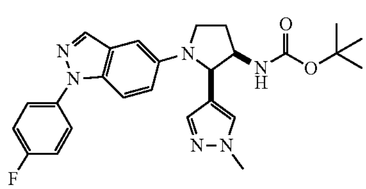 [SMILES: Cn1cc([C@@H]2[C@H](NC(=O)OC(C)(C)C)CCN2c2ccc3c(cnn3-c3ccc(F)cc3)c2)cn1] | ¹H NMR (DMSO-d₆) δ= 8.09 (s, 1H), 7.77 – 7.70 (m, 2H), 7.60 (d, 1H), 7.41 – 7.32 (m, 3H), 7.16 (s, 1H), 6.87 (dd, 1H), 6.77 (d, 1H), 6.72 (d, 1H), 4.95 (d, 1H), 4.08 (dd, 1H), 3.75 (s, 3H), 3.58 (t, 1H), 3.39 – 3.26 (m, 1H), 2.11 (dt, 1H), 2.10 – 1.97 (m, 1H), 1.42 (s, 9H). |
| 26 | 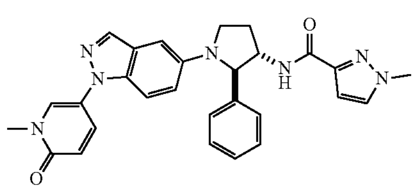 | ¹H NMR (DMSO-d₆) δ= 8.38 (d, 1H), 8.09 (d, 1H), 8.02 (d, 1H), 7.75 (d, 1H), 7.72 (dd, 1H), 7.47 (d, 1H), 7.42 – 7.37 (m, 2H), 7.34 (t, 2H), 7.28 – 7.21 (m, 1H), 6.75 (dd, 1H), 6.66 (dd, 2H), 6.53 (d, 1H), 4.84 (d, 1H), 4.27 (tt, 1H), 3.88 (s, 3H), 3.84 (td, 1H), 3.75 (td, 1H), 3.50 (s, 3H), 2.29 – 2.14 (m, 2H). |

GRE Agonist

The reporter cell line CHO—Gal4/GR consisted of a chinese hamster ovary (CHO) cell line (Leibniz Institute DSMZ—German Collection of Microorganisms and Cell Cultures GmbH: ACC-110) containing a firefly luciferase gene under the control of the GR ligand binding domain fused to the DNA binding domain (DBD) of GAL4 (GAL4 DBD-GR) stably integrated into CHO cells. This cell line was established by stable transfection of CHO cells with a GAL4-UAS-Luciferase reporter construct. In a subsequent step the ligand binding domain of the GR cloned into pIRES2-EGFP-GAL4 containing the DNA binding domain of GAL4 from pFA-AT2 was transfected. This fusion construct activated firefly luciferase expression under the control of a multimerized GAL4 upstream activation sequence (UAS). The signal of the emitted luminescence was recorded by the FLIPR$^{TETRA}$. This allowed for specific detection of ligand-induced activation of the GR and therefore for the identification of compounds with agonistic properties. The GAL4/UAS reporter was premixed with a vector that constitutively expressed Renilla luciferase, which served as an internal positive control for transfection efficiency.

The complete culture medium for the assay was:
DMEM F-12 (1:1) MIXTURE (LONZA cat. N°: BE04-687F/U1) 500 mL
5 mL of 100 mM Sodium Pyruvate (LONZA cat. N°: BE12-115E)
25 mL of 7.5% Sodium Bicarbonate (LONZA cat. N° BE17-613E)
6.5 mL of 1 M Hepes (LONZA cat. N°: BE17-737E)
5 mL of 100× Penicillin/Streptomycin (LONZA cat. N° DE17-602E)
50 mL of Fetal Bovine Serum (Euroclone cat. N° ECS 0180L)
0.25 mL of 10 mg/mL Puromycin (InvivoGen cat.: ant-pr-1)
0.5 mL of 100 mg/mL Zeocin (InvivoGen cat.: ant-zn-1)

Cryo-preserved CHO-Gal4/GR cells were suspended in complete medium and 5000 cells/25 µl/well were seeded into the wells of 384-well polystyrene assay plates (Thermo Scientific, cat.# 4332) and cultured at 37° C., 5% CO$_2$ and 95% humidity. After 24 hours growth medium was carefully removed and replaced by 30 µl Opti-MEM (GIBCO, cat.# 31985062) as assay buffer. To test the compounds an 8-point half-log compound dilution curve was generated in 100% DMSO starting from a 2 mM stock and compounds were then diluted 1:50 in Opti-MEM. 10 µl of compounds were then added to the wells containing 30 µl Opti-MEM resulting in a final assay concentration range from 10 µM to 0.003 µM in 0.5% DMSO. Compounds were tested at 8 concentrations in quadruplicate data points. Cells were incubated for 6 hour with compounds and beclometasone (Sigma, cat.# Y0000351) as control compound at 37° C., 5% CO$_2$ and 95% humidity in a total volume of 40 µl. Finally, cells were lysed with 20111 of Triton/Luciferin solution and the signal of the emitted luminescence was recorded at the FLIPR$^{TETRA}$ for 2 minutes.

The relative efficacy of a compound (% effect) was calculated based on the full effect of the agonist beclometasone:
% effect=((compound min)/(max min))×100
[min=Opti-MEM only, max=beclometasone]

To calculate EC$_{50}$, max, min and slope factor for each compound a concentration response curve was fitted by plotting % effect versus compound concentration using a 4 parameter logistic equation:

$$y=A+(B-A)/(1+((10C)/x)D)$$

[$A$=min $y$, $B$=max $y$, $C$=logEC$_{50}$, $D$=slope]

GRE Antagonist

The reporter cell line CHO—Ga14/GR consisted of a chinese hamster ovary (CHO) cell line (Leibniz Institute DSMZ—German Collection of Microorganisms and Cell Cultures GmbH: ACC-110) containing a firefly luciferase gene under the control of the GR ligand binding domain fused to the DNA binding domain (DBD) of GAL4 (GAL4 DBD-GR) stably integrated into CHO cells. This cell line was established by stable transfection of CHO cells with a GAL4-UAS-Luciferase reporter construct. In a subsequent step the ligand binding domain of the GR cloned into pIRES2-EGFP-GAL4 containing the DNA binding domain of GAL4 from pFA-AT2 was transfected. This fusion construct activated firefly luciferase expression under the control of a multimerized GAL4 upstream activation sequence (UAS). The signal of the emitted luminescence was recorded by the FLIPR$^{TETRA}$. This allowed for specific detection of antagonistic properties of compounds by measuring the ligand-induced inhibition of beclometasone-activated GR. The GAL4/UAS reporter was premixed with a vector that constitutively expressed Renilla luciferase, which served as an internal positive control for transfection efficiency.

The complete culture medium for the assay was:
DMEM F-12 (1:1) MIXTURE (LONZA cat. N°: BE04-687F/U1) 500 mL
5 mL of 100 mM Sodium Pyruvate (LONZA cat. N°: BE12-115E)
25 mL of 7.5% Sodium Bicarbonate (LONZA cat. N° BE17-613E)
6.5 mL of 1 M Hepes (LONZA cat. N°: BE17-737E)
5 mL of 100× Penicillin/Streptomycin (LONZA cat. N° DE17-602E)
50 mL of Fetal Bovine Serum (Euroclone cat. N° ECS 0180L)
0.25 mL of 10 mg/mL Puromycin (InvivoGen cat.: ant-pr-1)
0.5 mL of 100 mg/mL Zeocin (InvivoGen cat.: ant-zn-1)

Cryo-preserved CHO-Gal4/GR cells were suspended in complete medium and 5000 cells/25µ1/well were seeded into the wells of 384-well polystyrene assay plates (Thermo Scientific, cat. # 4332) and cultured at 37° C., 5% CO$_2$ and 95% humidity. After 24 hours growth medium was carefully removed and replaced by 20 µl Opti-MEM (GIBCO, cat.# 31985062) as assay buffer. For testing compounds an 8-point half-log compound dilution curve was generated in 100% DMSO starting from a 2 mM stock and compounds were then diluted 1:50 in Opti-MEM. To test the compounds in the antagonist mode 10 µl of compounds were then added to the wells containing 20 µl Opti-MEM and incubated for 10 min. After this pre-incubation 10 µl of the reference agonist beclometasone (Sigma, cat. # Y0000351) at an EC50 of 2.5 nM were added resulting in a final assay concentration range from 10 µM to 0.003 µM in 0.5% DMSO in a total volume of 40 µl. Compounds were tested at 8 concentrations in quadruplicate data points. Cells were incubated for 6 hour with compounds and mifepristone as control compound (Sigma, cat. # M8046) at 37° C., 5% CO2 and 95% humidity. Finally, cells were lysed with 20 µl of Triton/Luciferin solution and the signal of the emitted luminescence was recorded at the FLIPR$^{TETRA}$ for 2 minutes.

The relative efficacy of a compound (% effect) was calculated based on the full effect of the antagonist mifepristone:
% effect=((compound min)/(max min))×−100
[min=Opti-MEM only, max=mifepristone]

To calculate IC$_{50}$, max, min and slope factor for each compound a concentration response curve was fitted by plotting % effect versus compound concentration using a 4 parameter logistic equation:

$$y=A+(B-A)/(1+((10C)/x)D)$$

[$A$=min $y$, $B$=max $y$, $C$=logIC$_{50}$, $D$=slope]

Table summarizing biological data:

| cmpd # | IC50 or EC50<br>A < 100 nM,<br>B = 100 nM-1 µM,<br>C = 1 µM-15 µM |
| --- | --- |
| 1 | A |
| 2 | A |
| 3 | A |
| 4 | A |
| 5 | A |
| 6 | A |
| 7 | A |
| 8 | A |
| 9 | B |
| 10 | B |
| 11 | B |
| 12 | B |
| 13 | B |
| 14 | B |
| 15 | B |
| 16 | B |
| 17 | B |
| 18 | B |
| 19 | B |
| 20 | B |
| 21 | B |
| 22 | B |
| 23 | C |
| 24 | C |
| 25 | C |
| 26 | C |
| 27 | A |
| 28 | A |
| 29 | A |
| 30 | A |

"n.a.": not active in the GR cell-based assays, neither in the agonistic nor in the antagonistic mode.
"n.d.": not determined.

PROPHETIC EXAMPLES

The prophetic examples summarized in the following table could be synthesized in analogy to the synthesis described above. The person skilled in the art would know how to select suitable intermediates in order to obtain any to the prophetic examples 31 to 36.

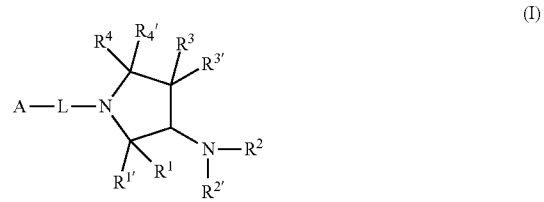

In the above tables, the example compounds wherein the substituents which are connected to the central pyrrolidone have a different relative orientation, e.g. phenyl moiety and methyl moiety up ("bold bond", ▲) and amide moiety down ("hashed bond", ⋯) or vice versa, are the "trans" diastereomer which is a racemic mixture of the two corresponding trans enantiomers.

The invention claimed is:
1. A compound according to general formula (I), wherein
R$^1$ represents —C$_{1-10}$-alkyl; —C$_{3-10}$-cycloalkyl; —C$_{1-6}$-alkylene-C$_{3-10}$-cycloalkyl; 3 to 7 membered heterocycloalkyl; —C$_{1-6}$-alkylene-(3 to 7 membered heterocycloalkyl); aryl; —C$_{1-6}$-alkylene-aryl; 5 or 6-membered heteroaryl; or —C$_{1-6}$-alkylene-(5 or 6-membered heteroaryl);
R$^{1'}$ represents H; —C$_{1-10}$-alkyl; or —C$_{3-10}$-cycloalkyl;
or R$^1$ and R$^{1'}$ together with the carbon atom to which they are bound form a C$_{3-10}$-cycloalkyl; or 3 to 7 membered heterocycloalkyl;
R$^2$ represents aryl; 5 or 6-membered heteroaryl; —C(=O)—C$_{1-10}$-alkyl; —C(=O)—O—C$_{1-10}$-alkyl; —C(=O)—C$_{3-10}$-cycloalkyl; —C(=O)—C$_{1-6}$-alkylene-C$_{3-10}$-cycloalkyl; —C(=O)—O—C$_{3-10}$-cycloalkyl; —C(=O)-(3 to 7 membered heterocycloalkyl); —C(=O)—C$_{1-6}$-alkylene-(3 to 7 membered heterocycloalkyl); —C(=O)—O-(3 to 7 membered heterocycloalkyl); —C(=O)-aryl; —C(=O)—C$_{1-6}$-alkylene-aryl; —C(=O)—O-aryl; —C(=O)-(5 or 6-membered heteroaryl); —C(=O)—C$_{1-6}$-alkylene-(5 or 6-membered heteroaryl); —C(=O)—O-(5 or 6-membered heteroaryl); —S(=O)$_{1-2}$—C$_{1-10}$-alkyl; —S(=O)$_{1-2}$—C$_{3-10}$-cycloalkyl; —S(=O)$_{1-2}$—C$_{1-6}$-alkylene-C$_{3-10}$-cycloalkyl); —S(=O)$_{1-2}$-(3 to 7 membered heterocycloalkyl); —S(=O)$_{1-2}$—C$_{1-6}$-alkylene-(3 to 7 membered heterocycloalkyl); —S(=O)$_{1-2}$-aryl; —S(=O)$_{1-2}$—C$_{1-6}$-alkylene-aryl; —S(=O)$_{1-2}$-(5 or 6-membered heteroaryl); or —S(=O)$_{1-2}$—C$_{1-6}$-alkylene-(5 or 6-membered heteroaryl);

R$^{2'}$ represents H;

R$^3$ and R$^{3'}$ independently from one another represent H; F; Cl; —C$_{1-10}$-alkyl; —C$_{3-6}$-cycloalkyl; —C$_{1-6}$-alkylene-C$_{3-6}$-cycloalkyl; 3 to 7 membered heterocycloalkyl; —C$_{1-6}$-alkylene-(3 to 7 membered heterocycloalkyl); —C$_{1-6}$-alkylene-aryl; or —C$_{1-6}$-alkylene-(5 or 6-membered heteroaryl);

or R$^3$ and R$^{3'}$ together with the carbon atom to which they are bound form a C$_{3-10}$-cycloalkyl; or 3 to 7 membered heterocycloalkyl;

R$^4$ and R$^{4'}$ independently from one another represent H; F; Cl; —C$_{1-10}$-alkyl; —C$_{3-6}$-cycloalkyl; —C$_{1-6}$-alkylene-C$_{3-6}$-cycloalkyl; 3 to 7 membered heterocycloalkyl; —C$_{1-6}$-alkylene-(3 to 7 membered heterocycloalkyl); —C$_{1-6}$-alkylene-aryl; or —C$_{1-6}$-alkylene-(5 or 6-membered heteroaryl);

L represents bond or —C$_{1-6}$-alkylene-;

A represents indolyl; indazolyl; benzisoxazolyl; benzisothiazolyl; benzotriazolyl; imidazopyridinyl; or benzoimidazolyl; in each case unsubstituted or mono- or disubstituted with R$^5$;

R$^5$ represents H; F; Cl; —C$_{1-10}$-alkyl; —C$_{1-10}$-alkenyl; —C$_{1-10}$-alkynyl; —C$_{3-6}$-cycloalkyl; —C$_{1-6}$-alkylene-C$_3$-6-cycloalkyl; 3 to 7 membered heterocycloalkyl; —C$_{1-6}$-alkylene-(3 to 7 membered heterocycloalkyl); aryl; —C$_{1-6}$-alkylene-aryl; 5 or 6-membered heteroaryl; —C$_{1-6}$-alkylene-(5 or 6-membered heteroaryl); —C(=O)—C$_{1-10}$-alkyl; —C(=O)—C$_{3-10}$-cycloalkyl; —C(=O)-(3 to 7 membered heterocycloalkyl); —O—C$_{1-10}$-alkyl; —O—C$_{3-6}$-cycloalkyl; —O-(3 to 7 membered heterocycloalkyl); —O-aryl; —O-(5 or 6-membered heteroaryl); —S(=O)$_{1-2}$—C$_{1-10}$-alkyl; —S(=O)$_{1-2}$—C$_{3-10}$-cycloalkyl; —S(=O)$_{1-2}$-(3 to 7 membered heterocycloalkyl); —S(=O)$_{1-2}$-aryl; or —S(=O)$_{1-2}$-(5 or 6-membered heteroaryl);

wherein —C$_{1-10}$-alkyl, —C$_{1-4}$-alkyl and —C$_{1-6}$-alkylene- in each case independently from one another is linear or branched, saturated or unsaturated;

wherein —C$_{1-10}$-alkyl, —C$_{1-4}$-alkyl, —C$_{1-6}$-alkylene-, —C$_{3-10}$-cycloalkyl and 3 to 7 membered heterocycloalkyl in each case independently from one another are unsubstituted or mono- or polysubstituted with one or more substituents selected from —F; —Cl; —Br; —I; —CN; —C$_{1-6}$-alkyl; —CF$_3$; —CF$_2$H; —CFH$_2$; —CF$_2$Cl; —CFCl$_2$; —C(=O)—C$_{1-6}$-alkyl; —C(=O)—OH; —C(=O)—O—C$_{1-6}$-alkyl; —C(=O)—NH$_2$; —C(=O)—NH(C$_{1-6}$-alkyl); —C(=O)—N(C$_{1-6}$-alkyl)$_2$; —OH; =O; —OCF$_3$; —OCF$_2$H; —OCFH$_2$; —OCF$_2$Cl; —OCFCl$_2$; —OC$_{1-6}$-alkyl; —O—C(=O)—C$_{1-6}$-alkyl; —O—C(=O)—O—C$_{1-6}$-alkyl; —O—(CO)—NH(C$_{1-6}$-alkyl); —O—C(=O)—N(C$_{1-6}$-alkyl)$_2$; —O—S(=O)$_2$—NH$_2$; —O—S(=O)$_2$—NH(C$_{1-6}$-alkyl); —O—S(=O)$_2$—N(C$_{1-6}$-alkyl)$_2$; —NH$_2$; —NH(C$_{1-6}$-alkyl); —N(C$_{1-6}$-alkyl)$_2$; —NH—C(=O)—C$_{1-6}$-alkyl; —NH—C(=O)—O—C$_{1-6}$-alkyl; —NH—C(=O)—NH$_2$; —NH—C(=O)—NH(C$_{1-6}$-alkyl); —NH—C(=O)—N(C$_{1-6}$-alkyl)$_2$; —N(C$_{1-6}$-alkyl)-C(=O)—C$_{1-6}$-alkyl; —N(C$_{1-6}$-alkyl)-C(=O)—O—C$_{1-6}$-alkyl; —N(C$_{1-6}$-alkyl)-C(=O)—NH$_2$; —N(C$_{1-6}$-alkyl)-C(=O)—NH(C$_{1-6}$-alkyl); —N(C$_{1-6}$-alkyl)-C(=O)—N(C$_{1-6}$-alkyl)$_2$; —NH—S(=O)$_2$OH; NH—S(=O)$_2$—C$_{1-6}$-alkyl; —NH—S(=O)$_2$—O—C$_{1-6}$-alkyl; —NH—S(=O)$_2$—NH$_2$; —NH—S(=O)$_2$—NH(C$_{1-6}$-alkyl); —NH—S(=O)$_2$N(C$_{1-6}$-alkyl)$_2$; —N(C$_{1-6}$-alkyl)-S(=O)$_2$—OH; —N(C$_{1-6}$-alkyl)-S(=O)$_2$—C$_{1-6}$-alkyl; —N(C$_{1-6}$-alkyl)-S(=O)$_2$—O—C$_{1-6}$-alkyl; —N(C$_{1-6}$-alkyl)-S(=O)$_2$—NH$_2$; —N(C$_{1-6}$-alkyl)-S(=O)$_2$—NH(C$_{1-6}$-alkyl); —(C$_{1-6}$-alkyl)-S(=O)$_2$—N(C$_{1-6}$-alkyl)$_2$; —SCF$_3$; —SCF$_2$H; —SCFH$_2$; —S—C$_{1-6}$-alkyl; —S(=O)—C$_{1-6}$-alkyl; —S(=O)$_2$—C$_{1-6}$-alkyl; —S(=O)$_2$—OH; —S(=O)$_2$—O—C$_{1-6}$-alkyl; —S(=O)$_2$—NH$_2$; —S(=O)$_2$—NH(C$_{1-6}$-alkyl); —S(=O)$_2$—N(C$_{1-6}$-alkyl)$_2$; —C$_{3-6}$-cycloalkyl; 3 to 6-membered heterocycloalkyl; phenyl; 5 or 6-membered heteroaryl; —O—C$_{3-6}$-cycloalkyl; —O-(3 to 6-membered heterocycloalkyl); —O-phenyl; —O-(5 or 6-membered heteroaryl); —C(=O)—C$_{3-6}$-cycloalkyl; —C(=O)-(3 to 6-membered heterocycloalkyl); —C(=O)-phenyl; —C(=O)-(5 or 6-membered heteroaryl); —S(=O)$_2$—(C$_{3-6}$-cycloalkyl); —S(=O)$_2$-(3 to 6-membered heterocycloalkyl); —S(=O)$_2$-phenyl or —S(=O)$_2$-(5 or 6-membered heteroaryl);

wherein aryl and 5 or 6-membered heteroaryl in each case independently from one another are unsubstituted or mono- or polysubstituted with one or more substituents selected from —F; —Cl; —Br; —I; —CN; —C$_{1-6}$-alkyl; —CF$_3$; —CF$_2$H; —CFH$_2$; —CF$_2$Cl; —CFCl$_2$; —C$_{1-4}$-alkylene-CF$_3$; —C$_{1-4}$-alkylene-CF$_2$H; —C$_{1-4}$-alkylene-CFH$_2$; —C(=O)—C$_{1-6}$-alkyl; —C(=O)—OH; —C(=O)—OC$_{1-6}$-alkyl; —C(=O)—NH(OH); —C(=O)—NH$_2$; —C(=O)—NH(C$_{1-6}$-alkyl); —C(=O)—N(C$_{1-6}$-alkyl)$_2$; —OH; =O; —OCF$_3$; —OCF$_2$H; —OCFH$_2$; —OCF$_2$Cl; —OCFCl$_2$; —OC$_{1-6}$-alkyl; —O—C$_{3-6}$-cycloalkyl; —O-(3 to 6-membered heterocycloalkyl); —O-aryl; —O-(5 or 6-membered heteroaryl); —NH$_2$; —NH(C$_{1-6}$-alkyl); —N(C$_{1-6}$-alkyl)$_2$; —NH—C(=O)—C$_{1-6}$-alkyl; —N(C$_{1-6}$-alkyl)-C(=O)—C$_{1-6}$-alkyl; —NH—C(=O)—NH$_2$; —NH—C(=O)—NH(C$_{1-6}$-alkyl); —NH—C(=O)—N(C$_{1-6}$-alkyl)$_2$; —N(C$_{1-6}$-alkyl)-C(=O)—NH(C$_{1-6}$-alkyl); —N(C$_{1-6}$-alkyl)-C(=O)—N(C$_{1-6}$-alkyl)$_2$; —NH—S(=O)$_2$—C$_{1-6}$-alkyl; —SCF$_3$; —S—C$_{1-6}$-alkyl; —S(=O)—C$_{1-6}$-alkyl; —S(=O)$_2$—C$_{1-6}$-alkyl; —S(=O)$_2$—NH$_2$; —S(=O)$_2$—NH(C$_{1-6}$-alkyl); —S(=O)$_2$—N(C$_{3-6}$-alkyl)$_2$; —C$_{3-6}$-cycloalkyl; —C$_{1-4}$-alkylene-C$_{3-6}$-cycloalkyl; —C$_{1-4}$-alkylene-(3 to 6-membered heterocycloalkyl); or phenyl;

in the form of the free compound or a physiologically acceptable salt thereof.

2. The compound according to claim 1; wherein

A represents phenyl or pyridinyl; wherein said phenyl and pyridinyl in each case independently from one another are unsubstituted or mono- or disubstituted with substituents selected from the group consisting of —F, —Cl, —Br, —CF$_3$, —CN, —C$_{1-10}$-alkyl, —O—C$_{1-10}$-alkyl, —O—C$_{3-10}$-cycloalkyl, —O-(3 to 7 membered heterocycloalkyl), —O-aryl or —O-(5 or 6-membered heteroaryl).

3. The compound according to claim 1, wherein
R$^1$ represents —C$_{1-10}$-alkyl; —C$_{3-10}$-cycloalkyl; —C$_{1-6}$-alkylene-C$_{3-10}$-cycloalkyl; aryl; or 5 or 6-membered heteroaryl; and/or
R$^{1'}$ represents H; CH$_3$; or cyclopropyl;
or R$^1$ and R$^{1'}$ together with the carbon atom to which they are bound form a C$_{3-10}$-cycloalkyl.

4. The compound according to claim 1, wherein
R$^2$ represents 5 or 6-membered heteroaryl; —C(=O)—C$_{1-10}$-alkyl; —C(=O)—O—C$_{1-10}$-alkyl; —C(=O)—C$_{3-10}$-cycloalkyl; —C(=O)-aryl; —C(=O)-(5 or 6-membered heteroaryl); —S(=O)$_2$—C$_{1-10}$-alkyl; —S(=O)$_2$—C$_{3-10}$-cycloalkyl; and/or
R$^{2'}$ represents H;
or R$^2$ and R$^{2'}$ together with the carbon atom to which they are bound form a 3 to 7 membered heterocycloalkyl.

5. The compound according to claim 1, wherein
R$^3$ represents H or —C$_{3-10}$-alkyl; and/or
R$^{3'}$ represents H or —C$_{1-10}$-alkyl.

6. The compound according to claim 1, wherein
R$^4$ represents H or —C$_{1-10}$-alkyl; and/or
R$^{4'}$ represents H or —C$_{3-10}$-alkyl.

7. The compound according to claim 1, wherein
R$^5$ represents H; F; Cl; —C$_{3-10}$-alkyl; —C(=O)—C$_{3-10}$-alkyl; —O—C$_{3-10}$-alkyl; —S(=O)$_{1-2}$—C$_{1-10}$-alkyl; —C$_{3-6}$-cycloalkyl; 3 to 7 membered heterocycloalkyl; aryl; —O-aryl; 5 or 6-membered heteroaryl; or —S(=O)$_{1-2}$—C$_{1-10}$-alkyl.

8. The compound according to claim 1, wherein
R$^2$ represents
5 or 6-membered heteroaryl, wherein said 5- to 6-membered heteroaryl is selected from the group consisting of thiazolyl, pyrimidinyl; pyrazolyl, oxazolyl, oxadiazolyl, isoxazolyl, isothiazolyl, wherein in each case said 5- to 6-membered heteroaryl is unsubstituted or mono- or disubstituted with substituents selected from the group consisting of —F, —Cl, —Br, —CH$_3$, —CF$_3$, —CN, =O, and —OCH$_3$;
—C(=O)—C$_{1-10}$-alkyl, unsubstituted or mono- or disubstituted with substituents selected from the group consisting of —F, —Cl, and —Br;
—C(=O)—O—C$_{1-10}$-alkyl, wherein said —C$_{1-10}$-alkyl is unsubstituted and is selected from the group consisting of methyl, ethyl, n-propyl, 2-propyl, n-butyl, 2-butyl, and tert-butyl;
—C(=O)-(5- to 6-membered heteroaryl), wherein said 5- to 6-membered heteroaryl is selected from the group consisting of thiazolyl, pyrazolyl, oxazolyl and 1-oxa-2,4-diazolyl, 1,2,5-oxadiazolyl, isoxazolyl, isothiazolyl, wherein in each case said 5- to 6-membered heteroaryl is unsubstituted or mono- or disubstituted with substituents selected from the group consisting of —F, —Cl, —Br, —CH$_3$, —CF$_3$, —CN, =O, and —OCH$_3$; or
—S(=O)$_2$-cyclopropyl, unsubstituted.

9. The compound according to claim 1, which is selected from the group consisting of:

1 N-[rac-(2S,3R)-2-(2,3-Dihydro-[1,4]benzodioxin-6-yl)-1-(1H-indol-4-yl-methyl)-pyrrolidin-3-yl]-cyclopropanesulfonic acid amide;

2 2,2-Difluoro-N-[rac-(2R,3 S)-2-phenyl-1-(1-pyridin-4-yl-1H-indazol-5-yl)-pyrrolidin-3-yl]-propionamide;

3 N-[rac-(2S,3R)-2-Cyclopropyl-1-[1-(4-fluorophenyl)-1H-indazol-5-yl]-pyrrolidin-3-yl]-2,2-difluoro-propionamide;

5 N-[rac-(2R,3S)-2-(2,3-Dihydro-[1,4]benzodioxin-6-yl)-1-[(5-fluoro-1H-indol-7-yl)-methyl]-pyrrolidin-3-yl]-cyclopropanesulfonic acid amide;

8 N-[(2R,3S)-2-Cyclopropyl-1-[1-(4-fluorophenyl)-1H-indazol-5-yl]-pyrrolidin-3-yl]-2,2-difluoro-propionamide;

9 N-[rac-(2R,3R)-2-(Cyclopropyl-methyl)-1-[1-(4-fluorophenyl)-1H-indazol-5-yl]-pyrrolidin-3-yl]-2,2-difluoro-propionamide;

10 N-[rac-(2R,3S)-2-(2,3-Dihydro-[1,4]benzodioxin-6-yl)-1-(1H-indazol-4-yl-methyl)-pyrrolidin-3-yl]-cyclopropanesulfonic acid amide;

11 N-[rac-(2R,3S)-2-Phenyl-1-(1-pyridin-4-yl-1H-indazol-5-yl)-pyrrolidin-3-yl]-cyclopropanecarboxylic acid amide;

12 5-Methyl-N-[rac-(2R,3S)-1-[1-(1-methyl-6-oxo-1H-pyridin-3-yl)-1H-indazol-5-yl]-2-phenyl-pyrrolidin-3-yl]-[1,2,4]oxadiazole-3-calboxylic acid amide;

13 2,2-Difluoro-N-[rac-(2R,3 S)-1-[1-(4-fluorophenyl)-1H-indazol-5-yl]-2-methyl-pyrrolidin-3-yl]-propionamide;

14 N-[rac-(2R,3S)-2-(2,3-Dihydro-[1,4]benzodioxin-6-yl)-1-[(1-methyl-1H-indol-4-yl)-methyl]-pyrrolidin-3-yl]-cyclopropanecarboxylic acid amide;

15 N-[rac-(2R,3S)-2-(2,3-Dihydro-[1,4]benzodioxin-6-yl)-1-[(1-methylsulfonyl-1H-indol-4-yl)-methylp]-pyrrolidin-3-yl]cyclopropanesulfonic acid amide;

16 2,2-Difluoro-N-[rac-(2R,3R)-1-[1-(4-fluorophenyl)-1H-indazol-5-yl]-2-(1-methyl-1H-pyrazol-4-yl)-pyrrolidin-3-yl]-propionamide;

17 2,2-Difluoro-N-[rac-(2R,3 S)-1-[1-(4-fluorophenyl)-1H-indazol-5-yl]-2-isopropyl-pyrrolidin-3-yl]-propionamide;

18 N-[rac-(2R,3S)-1-[1-(1-Methyl-6-oxo-1H-pyridin-3-yl)-1H-indazol-5-yl]-2-phenyl-pyrrolidin-3-yl]-cyclopropanesulfonic acid amide;

19 N-[rac-(2R,3R)-2-(Cyclopropyl-methyl)-1-[1-(4-fluorophenyl)-1H-indazol-5-yl]-pyrrolidin-3-yl]-carbamic acid tert-butyl ester;

21 N-[rac-(2R,3R)-2-Cyclobutyl-1-[1-(4-fluorophenyl)-1H-indazol-5-yl]-pyrrolidin-3-yl]-carbamic acid tert-butyl ester;

22 N-[rac-(2R,3S)-1-[(1-Acetyl-1H-indol-4-yl)-methyl]-2-(2,3-dihydro-[1,4]benzodioxin-6-yl)-pyrrolidin-3-yl]-cyclopropanesulfonic acid amide;

23 [rac-(2R,3 S)-2-Cyclopropyl-1-[1-(4-fluorophenyl)-1H-indazol-5-yl]-pyrrolodin-3-yl]-thiazol-2-yl-amine;

24 [rac-(2R,3 S)-2-Cyclopropyl-1-[1-(4-fluorophenyl)-1H-indazol-5-yl]-pyrrolidin-3-yl]-pyrimidin-2-yl-amine;

25 N-[rac-(2R,3R)-1-[1-(4-Fluorophenyl)-1H-indazol-5-yl]-2-(1-methyl-1H-pyrazol-4-yl)-pyrrolidin-3-yl]-carbamic acid tert-butyl ester;

26 1-Methyl-N-[rac-(2R,3S)-1-[1-(1-methyl-6-oxo-1H-pyridin-3-yl)-1H-indazol-5-yl]-2-phenyl-pyrrolidin-3-yl]-1H-pyrazole-3-carboxylic acid amide;

27 2,2-Difluoro-N-[5-[1-(4-fluorophenyl)-1H-indazol-5-yl]-5-azaspiro[3.4]octan-8-yl]-propionamide;

28 N-((2R,3S)-1-(1-(4-fluorophenyl)-1H-indazol-5-yl)-2-phenylpyrrolidin-3-yl)cyclopropanecarboxamide;

29 N-((2R,3S)-1-(1-(4-fluorophenyl)-1H-indazol-5-yl)-2-phenylpyrrolidin-3-yl)methanesulfonamide;

30 2,2-difluoro-N-((2R,3 S)-1-(1-(4-fluorophenyl)-1H-indazol-5-yl)-2-phenylpy rrolidin-3-yl)propanamid;

31 2,2-difluoro-N-[rac-((2R,3 S)-1-(1-(4-fluorophenyl)-1H-indazol-5-yl)-5,5-dimethyl-2-phenylpyrrolidin-3-yl)]propanamide;

32 N-[rac-((2R,3S)-1-(1-(4-fluorophenyl)-1H-indazol-5-yl)-5,5-dimethyl-2-phenylpyrrolidin-3-yl)]cyclopropanecarboxamide;

33 2,2-difluoro-N-[rac-((2R,3S,5S)-1-(1-(4-fluorophenyl)-1H-indazol-5-yl)-5-methyl-2-phenylpyrrolidin-3-yl)]propanamide;

34 N-[rac-((2R,3S,5S)-1-(1-(4-fluorophenyl)-1H-indazol-5-yl)-5-methyl-2-phenylpyrrolidin-3-yl)]cyclopropanecarboxamide;

35 2,2-difluoro-N-[rac-((2R,3S,5R)-1-(1-(4-fluorophenyl)-1H-indazol-5-yl)-5-methyl-2-phenylpyrrolidin-3-yl)]propanamide; and 36 N-[rac-((2R,3S,5R)-1-(1-(4-fluorophenyl)-1H-indazol-5-yl)-5-methyl-2-phenylpyrrolidin-3-yl)]cyclopropanecarboxamide;

in the form of the free compound or a physiologically acceptable salt thereof.

10. A pharmaceutical dosage form comprising a compound according to claim 1.

11. A method for the treatment and/or prophylaxis of pain and/or inflammation, said method comprising administering to a patient in need thereof an effective amount therefor of a compound according to claim 1.

12. The method according to claim 11, wherein the pain is inflammatory pain.

* * * * *